(12) United States Patent
Ghawi et al.

(10) Patent No.: US 9,017,732 B1
(45) Date of Patent: Apr. 28, 2015

(54) ANTIBACTERIAL THERAPY WITH A WHOLE, LEECH SALIVA EXTRACT

(71) Applicant: Biopep Solutions, Inc., Richmond (CA)

(72) Inventors: Abbas Mohammad Ghawi, Selangor (MY); Ahmed Merzouk, Richmond (CA); Abdualrahman Abdualkader, Pahang (MY); Mohamed Alaama, Pahang (MY)

(73) Assignee: Biopep Solutions, Inc., Richmond, BC (CA)

( * ) Notice: Subject to any disclaimer, the term of this patent is extended or adjusted under 35 U.S.C. 154(b) by 0 days.

(21) Appl. No.: 14/563,829

(22) Filed: Dec. 8, 2014

Related U.S. Application Data

(63) Continuation of application No. 14/282,893, filed on May 20, 2014, which is a continuation of application No. 13/624,860, filed on Sep. 21, 2012, now Pat. No. 8,784,896.

(60) Provisional application No. 61/701,735, filed on Sep. 17, 2012.

(51) Int. Cl.
    *A61K 35/37*     (2006.01)
    *A61K 38/00*     (2006.01)
    *A01N 63/00*     (2006.01)
    *A61K 35/62*     (2006.01)

(52) U.S. Cl.
    CPC .............. *A61K 35/62* (2013.01); *A01N 63/00* (2013.01)

(58) Field of Classification Search
    None
    See application file for complete search history.

(56) References Cited

U.S. PATENT DOCUMENTS

| | | | |
|---|---|---|---|
| 4,588,587 | A | 5/1986 | Gasic |
| 5,246,715 | A | 9/1993 | Orevi et al. |
| 5,393,873 | A | 2/1995 | Schmied et al. |
| 5,447,911 | A | 9/1995 | Cardin et al. |
| 5,455,181 | A | 10/1995 | Strube et al. |
| 5,472,942 | A | 12/1995 | Sawyer et al. |
| 5,866,120 | A | 2/1999 | Karageozian et al. |
| 6,551,590 | B2 | 4/2003 | Karageozian et al. |
| 6,572,855 | B1 | 6/2003 | Johnsson et al. |
| 6,610,292 | B2 | 8/2003 | Karageozian et al. |
| 6,863,886 | B2 | 3/2005 | Karageozian et al. |
| 7,049,124 | B1 | 5/2006 | Kordowicz et al. |
| 8,501,241 | B1 | 8/2013 | Ghawi et al. |
| 8,685,462 | B1 | 4/2014 | Merzouk et al. |
| 8,784,896 | B2 | 7/2014 | Ghawi et al. |
| 8,790,711 | B2 | 7/2014 | Ghawi et al. |
| 2003/0021786 | A1 | 1/2003 | Gevas et al. |
| 2011/0070184 | A1 | 3/2011 | Bernhagen et al. |

FOREIGN PATENT DOCUMENTS

| | | |
|---|---|---|
| CN | 102258771 A | 11/2011 |
| EP | 0 503 829 | 9/1992 |
| EP | 0 875 564 | 5/1997 |
| IL | 90573 | 7/1994 |
| WO | WO 87/00860 | 2/1987 |
| WO | WO 93/11239 | 6/1993 |
| WO | WO 94/09039 | 4/1994 |
| WO | WO 94/23735 | 10/1994 |
| WO | WO 94/26777 | 11/1994 |
| WO | WO 95/04750 | 2/1995 |
| WO | WO 00/77221 | 12/2000 |
| WO | WO 2009/018640 | 2/2009 |
| WO | WO 2011/045427 | 4/2011 |
| WO | PCT/US2013/60221 | 5/2013 |
| ZA | 904622 | 6/1990 |

OTHER PUBLICATIONS

U.S. Appl. No. 14/282,865, filed Sep. 17, 2012, Ghawi et al.
U.S. Appl. No. 14/282,893, filed Sep. 17, 2012, Ghawi et al.
U.S. Appl. No. 14/502,388, filed Sep. 17, 2012, Ghawi et al.
Abdualkader, A.M., et al. The anticoagulant activity of malaysian leech saliva extract. In: the 25th scientific meeting of malaysian society of pharmacology and physiology. University Putra Malaysia. UPM (2011).
Abdualkader, A., et al. Some biological activities of malaysian leech saliva extract. IIUM Engineering Journal 12: 1-9 (2011).
Abdualkader, A.M., et al. Characterization and optimization of lyophilization and storage conditions of leech saliva extract from the tropical leech hirudinaria manillensis. Pak J Pharm Sci. 26(3): 525-536 (Jul. 2013).
Abeeleh, M. A., et al. Induction of diabetes mellitus in rats using intraperitoneal streptozotocin: a comparison between two strains of rats. European Journal of Scientific Research 32: 398-402 (2009).
Alaama, M., et al. Isolation and analytical characterization of local malaysian leech saliva extracts. IIUM Engineering Journal 12(4): 51-59 (2011).
Althunibat, O.Y., et al. In vitro antioxidant and antiproliferative activities of three malaysian sea cucumber species. European Journal of Scientific Research 37: 376-387 (2009).

(Continued)

*Primary Examiner* — Qiuwen Mi
(74) *Attorney, Agent, or Firm* — Brian S. Boyer; Syndicated Law, PC

(57) ABSTRACT

Methods are provided for isolating and using a whole-saliva leech extract. The methods can include feeding a phagostimulatory agent to a leech; inducing a regurgitation in the leech, the inducing including placing the leech in an environment having a temperature of less than about 0° C.; and, collecting an unrefined, whole saliva in the regurgitation of the cooled leech. The methods can include revitalizing the leech by warming it at a temperature ranging from about 5° C. to about 40° C. Stable, lyophilized, whole-saliva extracts of a leech are also provided, the extract having a stable activity when stored for use at a temperature below about −20° C., the extract maintaining at least 70% of the activity for at least 6 months. The extracts can be used to treat solid tumors, treat liquid tumors, treat diabetes, treat a viral disease, treat a parasitic disease, treat an antibacterial disease, or serve as an antioxidant.

22 Claims, 23 Drawing Sheets

(56) References Cited

OTHER PUBLICATIONS

Arolas, J.L., et al. NMR structural characterization and computational predictions of the major intermediate in oxidative folding of leech carboxypeptidase inhibitor. Structure 13: 1193-1202 (Aug. 2005).
Arolas, J.L., et al. Study of a major intermediate in the oxidative folding of leech carboxypeptidase inhibitor: contribution of the fourth disulfide bond. J. Mol. Biol. 205-352 : 961-975 (2005).
Arolas, J.L., et al. Designing out disulfide bonds of leech carboxypeptidase inhibitor: implications for its folding stability and function. J. Mol. Biol. 392: 529-546 (2009).
Ascenzi, P., et al. Proteinase inhibitors from the euroean medicinal leech hirudo medicinalis: structural, functional and biomedical aspects. Molec. Aspects Med 16: 215-313 (1995).
ATCC animal cell culture guide: tips and techniques for continuous cell lines. Manassas, VA, 40 pages (Jan. 2012).
Bagdy, D., et al. Large scale preparation of hirudin. Thrombosis Research 2(3): 229-238 (1973).
Bagdy, D., et al. Hirudin, Methods in Enzymology, in L. Laszlo (Ed.) Academic Press, 45: 669-678 (1976).
Bambace, N.M., et al. The platelet contribution to cancer progression. J Thromb Haemost 9(2): 237-249 (2011).
Barnes, C.S., et al. Production and characterization of saratin, an inhibitor of von willebrand factor-dependent platelet adhesion to collagen, semin. Thromb. Hemost 27(4): 337-347 (2001).
Baskova, I.P., et al. Inhibition of plasma kallikrein. Kininase and kinin-link activities of preparations from the medicinal leeches. Thromb Res 67(6): 721-730 (1992).
Baskova, I.P., et al. Proteinase inhibitors from the medicinal leech hirudo medicinalis. Biochemistry (Mosc) 66(7): 703-714 (2001).
Baskova, I.P., et al. Seperation of monomerizing and lysozyme activities of destabilase from medicinal leech salivary gland secretion. Biochemistry (Mosc) 66(12): 1368-1373 (2001).
Baskova, I.P., et al. Protein profiling of the medicinal leech salivary gland secretion by proteomic analytical methods. Biochemistry (Mosc) 69(7): 770-775 (2004).
Baskova, I.P., et al. Proteomic analysis methods for characterization of proteins from the salivary gland secretions of the medicinal leech during different seasons. Biochemistry (Mosc) 72(2): 219-225 (2007).
Baskova, I.P., et al. Proteins and peptides of the salivary gland secretion of medicinal leeches Hirudo Verbena, H. Medicinalis, and H. Orientalis. Biochemistry (Mosc) 73(3): pp. 315-320 (2008).
Baskova, I.P., et al. Purification of hirudin by the method of isoelectric focussing, article in russian, abstract, biokhimiya 41(5): 939-941(1976).
Baskova, I.P., et al. Hirudin from leech heads and whole leeches and "pseudo-hirudin" from leech bodies. Thrombosis Research 30(5): 459-467 (1983).
Baskova, I.P., et al. Lipase and cholesterol-esterase activity in the salivary gland secretions of the medical leech hirudo medicinalis. article in Russian (abstract). Biokhimiia 49(4), pp. 676-678 (1984).
Baskova, I.P., et al. Destabilase: An enzyme of medicinal leech salivary gland secretion hydrolyzes the isopeptide bonds in stabilized fibrin. Biokhimiia 50(3): 424-431 (1985).
Baskova, I.P., et al. Antithrombin, antitrypsin and antichymotrypsin activities of the salivary gland secretion and intestinal chyme of medicinal leeches, antichymotrypsin activity of partially purified preparations of hirudin and sseudohirudin. Folia Haematologica 111(6): 831-837 (1984).
Basu, S., et al. A leech in the large bowel, [Case Reports]. Journal of the Royal Society of Medicine 97(2): 83 (2004).
Beckman, K.B., et al. The free radical theory of aging matures. Physiol Rev April 78(2): 547-581 (1998).
Bjelakovic, G., et al. Mortality in randomized trials of antioxidant supplements for primary and secondary prevention. (Abstract) JAMA 297: 842-857 (2007).
Blankenship, D.T., et al. Amino acid sequence of ghilanten: anticoagulant-antimetastatic principle of the south american leech Heamenteria Ghilianii. Biochemical and biophysical research communications 166(3): 1384-1389 (Feb. 14, 1990).
Blois, MS. Antioxidant determinations by the use of a stable free radical. Nature 181: 1199-1200 (1958).
Bondet, V, et al. Kinetics and mechanisms of antioxidant activity using the dpph free radical method, LWT. Food Science and Technology 30: 609-615 (1997).
Booth, D. A.,et al. Hunger elicited in the rat by a single injection of bovine crystalline insulin. Physiology & Behavior 3: 439-446 (1968).
Bösenberg, L.H.,et al. The mechanism of action of oral antidiabetic drugs: A review of recent literature. JEMDSA 13: 80-88 (2008).
Brankamp, R.G., et al. Studies on the anticoagulant antimetastatic and heparin-binding properties of ghilanten-related inhibitors, blood coagul. Fibrinolysis 2(1): 161-166 (1991).
Brankamp, R.G., et al. Ghilantens: Anticoagulant-Antimetastatic proteins from the south american leech, Haementeria Ghilianii. The Journal of Laboratory and Clinical Medicine 115(1): 89-97 (Jan. 1990).
Brewer, M.S. Natural Antioxidants: Sources, compounds, mechanisms of action, and potentional applications. Comprehensive Reviews in Food Science and Food Safety10: 221-247 (2011).
Budzynski, A. Z., et al. Anticoagulant and fibrinolytic properties of salivary proteins from the leech Haementeria Ghilianii. Proc soc exp biol med 168: 266-275 (1981).
CCME: Canadian water quality guidelines for the protection of aquatic life, summary table in canadian environmental quality guidelines. Canadian council of ministers of the environment, Winnipeg (1999).
Chang, J-Y. The functional domain of hirudin, a thrombin-specific inhibitor. FEBS 164(2): 307-313 (Dec. 1983).
Chopin, V., et al. Amino-acid-sequence determination and biological activity of cytin, a naturally occurring specific chymotrypsin inhibitor from the leech theromyzon tessulatum. European Journal of Biochemistry/FEBS 249(3): 733-738 (1997).
Chopin, V., et al. Amino-acid-sequence determination and biological activity of therin, a naturally occuring specific trypsin inhibitor from the leech thermyzon tessulatum. Eur J Biochem 254: 656-570 (1998).
Chopin, V., et al. Amino-acid-sequence determination and biological activity of tessulin, a naturally occurring trypsin-chymotrypsin inhibitor isolated from the leech theromyzon tessulatum. Eur J Biochem 258: 662-668 (1998).
Chopin, V., et al. Therostasin, a novel clotting factor xa inhibitor from the rhynchobdellid leech, theromyzon tessulatum. J. Biol. Chem. 275(42): 32701-32707 (2000).
Chudzinski-Tavassi, A.M., et al. Fibrino (geno) lytic properties of purified hementerin, a metalloproteinase from the leech haementeria depressa. Thromb Haemost 80(1): 155-160 (1998).
Clynen, E., et al. A review of the most important classes of serine protease inhibitors in insects and leeches. Medicinal Chemistry Reviews 2(3): 197-2006 (2005).
Collins A.R. Antioxidant intervention as a route to cancer prevention. Eur J Cancer 41: 1923-1930 (2005).
Condra, C., et al. Isolation and structural characterization of a potent inhibitor of coagulation factor xa from the leech haementeria ghilianii. Thrombosis and Haemostasis 61(3): 437-441 (1989).
Connolly, T.M., et al. An inhibitor of collagen-stimulated platelet activation from the salivary glands of the haementeria officinalis leech i. identification, isolation, and characterization. The Journal of Biological Chemistry 267(10): 6893-6898 (1992).
Cornett P.A., et al. Cancer, current medical diagnosis and treatment. The McGraw-Hill companies USA 29: 1450-1511 (2010).
Corral-Rodriguez, M.A., et al. Leech-derived thrombin inhibitors: From structures to mechanisms to clinical applications. J Med Chem 53: 3847-3861 (2010).
Cruz, C.P., et al. Saratin, an inhibitor of von willebrand factor-dependant platelet adhesion, decreases platelet aggregation and intimal hyperplasia in a rat carotid endarterectomy model. J. Vasc. Surg. 34(4): 724-729 (2001).
de Eguileor, M., et al. Hirudo Medincinalis: A new model for testing activators and inhibitors of angiogenesis. Angiogenesis (4) 99: 299-312 (2001).

(56) References Cited

OTHER PUBLICATIONS di Marco, S. et al. Recombinant Hirustasin: Production in yeast, crystallization, and interaction with serine proteases. Protein Science 6: 109-118 (1997).

Deckmyn, H., et al. Calin from Hirudo Medincinalis, an inhibitor of platelet adhesion to collagen, prevents platelet-rich thrombosis in hamsters. Blood 85(3): 712-719 (Feb. 1995).

Dickinson, M.H., et al. Feeding behavior of the medicinal leech, hirudo medicinalis I. Journal of comparative physiology 154(4): 449-455 (1984).

Dodt, J., et al. The complete amino acid sequence of hirudin, a thrombin specific inhibitor: Application of colour carboxymethylation. FEBS 165(2): 180-184 (Jan. 1984).

Dodt, J., et al. The complete covalent structure of hirudin, localization of the disulfide bonds. Biological Chemistry Hoppe-Seyler 366(4): 379-385 (1985).

Dvorak, Z., et al. Evaluation of in vitro cytotoxicity of 6-benzylaminopurine carboplatin derivatives against human cancer cell lines and primary human hepatocytes. Toxicol in vitro 25: 652-656 (2011).

Eaton, A. D., et al. Standard methods for the examination of water & wastewater. American public health association (2005).

Electricwala, A., et al. Isolation of thrombin inhibitor from the leech hirudinaria manillensis. Blood Coagul Fibrinolysis 2(1): 83-89 (1991).

Electricwala, A., et al. Biochemical characterisation of a pancreatic elastase inhibitor from the leech Hirudinaria Manillensis. J Enzyme Inhib. 6(4): 293-302 (1992).

Electricwala, A., et al. The complete amino acid sequence of a hirudin variant from the leech hirudinaria manillensis. J Protein Chem. 12(3): 365-370 (1993).

Elliott, E.J. Chemosensory stimuli in feeding behavior of the leech hirudo medicinalis. Journal of comparative physiology 159(3): 391-401 (1986).

Evans, B.D., et al. Identification of RFamide neuropeptides in the medicinal leech. Peptides 12(5): 897-908 (1991).

Failloux, A. B., et al. Oral infection of aedes polynesiensis by wuchereria bancrofti by using parafilm membrane feeding. Journal of the american mosquito control association 7(4): 660-662 (1991).

Fairbanks, G, et al. Electrophoretic analysis of the major polypeptides of the human erythrocyte membrane. Biochemistry 10(13): 2606-2617 (1971).

Faria, F, et al. A new factor xa inhibitor (lefaxin) from the haementeria depressa leech. Thromb Haemost 82: 1469-1473 (1999).

Fink, E., et al. The primary structure of Bdellin B-3 from the leech Hirudo Medicinalis. Bdellin B-3 is a compact proteinase inhibitor of a "non-classical" Kazal type, it is present in the leech in a high molecular mass form. Biological chemistry Hoppe-Seyler 367(12): 1235-1242 (1986).

Finney, S., et al. Tridegin, a new peptidic inhibitor of factor xiiia, from the blood-sucking leech Haementeria Ghilianii. Biochem J. 324: 797-805 (1997).

Galun, R., et al. Chemical specificity of the feeding response in hirudo medicinalis. Comp. Biochem. Physiol. 17(1): 69-73 (1966).

Gasic, G.J., et al. Inhibition of lung tumor colonization by leech salivary gland extracts from Haementeria Ghilianii. Cancer Res. 43(4): 1633-1636 (Apr. 1983).

Gasic, GJ, et al. Leech salivary gland extract from haementeria officinalis, a potent inhibitor of cyclophosphamide- and radiation-induced artifical metastasis enhancement. Cancer Res. 44: 5670-5676 (1984).

Ghawi, A.M., et al. Free radial scavenging activity of the medicinal malaysian leech saliva extract, Hirudinaria Manillensis. J Bioequiv Availab S14: 1-4 (2012).

Ghawi, A.M., et al. Season Variant and starvation period influence on the antithrombotic activity of leech saliva extract from the medicinal Malaysian leech, Hirudinaria Manillensis. J Bioequiv Availab S14: 1-5 (2012).

Gong, G., et al. Anti-thrombosis effect of diosgenin extract from dioscorea zingiberensis C.H. Wright in vitro and in vivo. Phytomedicine 18(6): 458-463 (2010).

Govedich, F. R., et al. All about leeches (Mar. 14, 2005) [online] URL: http://www.invertebrate.us/leech/ (Mar. 14, 2005).

Govedich, F. R., et al. Placobdelloides stellapapillosa sp. N. (Glossiphoniidae) found feeding on crocodiles and turtles. Hydrobiologia 474: 253-256(2005).

Govedich, F. R., et al. Annelida: Clitellata, Hirudinea, Euhirudinea, freshwater invertebrate of Malaysia and Borneo, in C. Y. a. Y. H. Sen (Ed.), Academy of sciences Malaysia publishing pp. 175-190 (2004).

Green, P.A., et al. Medicinal leech use in microsurgery. J Hand Surg Am 35(6): 1019-1021 (2010).

Griessbach, U., et al. Assay of hirudin in plasma using a chromogenic thrombin substrate. Thromb Res 37(2): 347-350 (1985).

Gronwald, W., et al. Structure of the leech protein saratin and characterization of it's binding to collagen. J Mol Biol. 381(4): 913-927 (2008).

Haripyaree, A., et al. Evaluation of antioxidant properties of some wild edible fruit extracts by cell free assays. Electronica journal of environmental agriculture and food chemistry 9(2): 345-350 (2010).

Harsfalvi, J., et al. Calin from hirudo medincinalis, an inhibitor of von willebrand factor binding to collagen under static and flow conditions. Blood 85(3): 705-711 (1995).

Haycraft, J.B. On the action of a secretion obtained from the medicinal leech on the coagulation of the blood. Proceedings of the Royal Society of London. The Royal Society vol. 36: 478-487(1883-1884).

Heim, K., et al. C-terminal proteolytic degradation of recombinant desulfato-hirudin and it's mutants in the yeast sccharomyces cerevisiae. Eur J Biochem 226(2): 341-353 (1994).

Hercberg, S., et al. The potential role of antioxidant vitamins in preventing cardiovascular diseases and cancers. Nutrition 14: 513-520 (1998).

Hernandez-Ledesma, B., et al. Preparation of antioxidant enzymatic hydrolysates from α-lactalbumin and β-lactoglobulin, identification of active peptides by HPLC-MS/MS. J Agric food chem 53: 588-593 (2005).

Hokama, Y., et al. Maintenance of adult and nymphal ornithodoros coriaceus (acari: argasidae) by artificial feeding through a parafilm membrane. Journal of Medical Entomology 24(3): 319-323 (1987).

Hong, S.J., et al. Purification of granulin-like polypeptide from the blood-sucking leech, *Hirudo nipponia*. Protein Expression and Purification 16(2): 340-346 (1999).

Hovingh, P., et al. Hyaluronidase activity in leeches (Hirudinea). Comp Biochem Physiol 124(3): 319-326 (1999).

Hsu, HF, et al. Typhonium blumei extract inhibits proliferation of human lung adenocarcinoma A549 cells via induction of cell cycle arrest and apoptosis. J Ethnopharmacol 135: 492-500 (2011).

Iwanaga, S., et al. Identification and characterization of novel salivary thrombin inhibitors from the ixodidae tick, *Haemaphysalis longicornis*. European journal of biochemistry/FEBS 270(9): 1926-1934 (2003).

Iyer, L., et al. Alteration of pharmacokinetics and pharmacodynamics of recombinant hirudin (rHV2-Lys 47) after repeated intravenous administration in dogs. Thromb Res 69(1): 59-70 (1993).

Jenkins, A.J.,et al. Diabetes and oxidant stress, atherosclerosis and oxidant stress: A New prospective. Holtzman, J. L. (ed.), New York: Springer science+business media, LLC. 7: 123-158 (2008).

Jiang, L., et al. Comparison of protein precipitation methods for sample preparation prior to proteomic analysis. Journal of Chromatography 1023(2): 317-320 (2004).

Johansen et al. Oxidative stress and the use of antioxidants in diabetes: Linking basic science to clinical practice. Cardiovascular Diabetology (4)5: (2005).

Jung, H, II, et al. Isolation and characterization of guamerin, a new human leukocyte elastase inhibitor from *Hirudo nipponia*. J Biol Chem 270(23): 13879-13884 (1995).

Jutisz, M., et al. Purification of hirudin, article in french. (Abstract) Bull soc chim biol 45: 55-67 (1963).

Kasicka, V. Recent advances in CE and CEC of peptides (2007-2009). Electrophoresis 31: 122-146 (2010).

(56) References Cited

OTHER PUBLICATIONS

Kelen, E. M., et al. Fibrinogenolytic substance (Hementerin) of Brazilian blood-sucking leeches (Haementeria lutzi Pinto 1920). Haemostasis 4(1): 51-64 (1975).
Keli, So., et al. Dietary flavonoids, antioxidant vitamins, and indicence of stroke: The zutphen study. Arch Intern Med 156: 637-642 (1996).
Kheng, L.C., et al. Heavy metals in some Malaysian mosses. Pertanika 6(3): 48-540 (1983).
King. M. W. Blood coagulation, the medical biochemistry p. (1996), [online] URL: http://themedicalbiochemistrypage.org/blood-coagulation.html. [retreived Dec. 21, 2012].
Knobloch, K. Leeches in microsurgery—an evidence-based approach. toxins and hemostasis, netherlands. Springer Science pp. 735-745 (2011).
Koh, C. Y., et al. Molecular diversity of anticoagulants from haematophagous animals. Thromb Haemost 102(3): 437-453 (2009).
Kraemer, B.A., et al. Use of leeches in plastic and reconstructive surgery: A review. J Reconstr Microsurg 4(5): 381-386 (1988).
Kumar, G.P.S., et al. Anti-diabtic activity of fruits of terminalia chebula on streptozotocin induced diabetic rats. Journal of health science 52: 283-291 (2006).
Kuriyama, S. Interpreting the history of bloodletting. J Hist med allied sci 50(1): 11-46 (1995).
Langner, K. F. A., et al. Collection and analysis of salivary proteins from the biting midge *Culicoides nubeculosus* (diptera: ceratopogonidae). J med entomol 44(2): 238-248 (2007).
Latif, F.A. Isolation of antithrombin protein from local leeches (Hirudinoria Manillensis), Universiti Teknologi Malaysia website [online] URL: http://eprints.utm.my/4825/ [retrieved on Feb. 2, 2010].
Laurent, V. et al. Isolation of a renin-like enzyme from the leech theromyzon tessulatum. Peptides 16(8): 1351-1358 (1995).
Ledizet, M., et al. Discovery and pre-clinical development of antithrombotics from hematophagous invertebrates. Curr med chem cardiovascular hematol agents 3(1): 1-10 (2005).
Lent, C., et al. Serotonin integrates the feeding behavior of the medicinal leech, journal of comparative physiology A. Physiology 154(4): 457-471 (1984).
Lent, C. M. Serotonergic modulation of the feeding behavior of the medicinal leech. Brain research bulletin 14(6): 643-655 (1985).
Lent, C., et al. On the termination of ingestive behaviour by the medicinal leech. The journal of experimental biology 131: 1-15 (1987).
Lent, C., et al. Ingestive behaviour and physiology of the medicinal leech. The journal of experimental biology 137: 513-527 (1988).
Lenzen, S. The mechanisms of alloxan- and streptozotocin-induced diabetes. Diabetologia 51: 216-226 (2008).
Letelier, M.E, et al. DPPH and oxygen free radicals as pro-oxidant of biomolecules. Toxicol In vitro 22: 279-286. (2008).
Liu, G., et al. Systematic study of the substituted active c-terminus of hirudin. J pept res 54(6): 480-490 (1999).
Liu, R., et al. Purification and identification of three novel antioxidant peptides from cornu bubali (water buffalo horn). Peptides 31: 786-793 (2010).
Lombardi, A ., et al. Rational design of true hirudin mimetics: Synthesis and characterization of multisite-directed α-directed α-thrombin inhibitors. J Med Chem 39(10): 2008-2017 (1996).
Lu, W-Y., et al. Deciphering the role of the electrostatic interactions involving Gly70 in Eglin C by total chemical protein synthesis. Biochemistry 39(13): 3575-3584 (2000).
Madubunyi, I., et al. In vitro antioxidant and in vivo antidiabetic potential of the methanol extract of ficus glumosa del (Moraceae) stem bark in alloxan-induced diabetic mice. Comparative clinical pathology pp. 1-6 (2010).
Malinconico, S.M., et al. Hementin: Anticoagulant protease from the salivary gland of the leech Haementeria Ghilianii. The journal of laboratory and clinical medicine103(1): 44-58 (1984).

Mao, S.J.T., et al. Interaction of hirudin with thrombin: identification of a minimal binding domain of hirudin that inhibits clotting activity. Biochemistry 27(21): 8170-8173 (1988).
Mao, S.J.T., et al. Rapid purification and revised amino-terminal sequence of hirudin: A specific thrombin inhibitor of the bloodsucking leech. Anal biochem 161: 514-518 (1987).
Maraganore, J.M, et al. Design and characterization of hirulogs: A novel class of bivalent peptide inhibitors of thrombin. Biochemistry 29(30): 7095-7101 (1990).
Markwardt, F. Die isolierung und chemische charakterisierung des hirudins, hoppe-seyler's zeitschrift für physiologische chemie (article in German). Jahresband 308: 147-156 (1957).
Markwardt, F., et al. Die reaktion zwischen hirudin und thrombin, hoppe-seyler's zeitschrift für physiologische chemie (article in German) 312(1-3): 85-98 (1958).
Markwardt, F., et al. Hirudin as an inhibitor of thrombin. Methods Enzymol 19: 924-932 (1970).
Markwardt, F., et al. The antithrombotic effect of synthetic thrombin inhibitors. Thrombosis research 1(3): 243-251 (1972).
Markwardt, F., et al. Studies on antithrombotic effects of recombinant hirudin. Thromb res 54(5): 377-388 (1989).
Markwardt, F. The development of hirudin as an antithrombotic drug. Thromb res 74(1): 1-23 (1994).
Markwardt, F. Historical prespective of the development of thrombin inhibitors. Pathophysiol haemost thromb 32(3): 15-22 (2002).
Mazur, P.,et al. Ornatins: Potent Glycoprotein IIb-IIIs antagonists and platelet aggregation inhibitors from the leech placobdella ornata. European journal of biochemistry 202(3): 1073-1082 (1991).
McCormick, R.M., et al. Capillary zone electrophoretic separation of peptides and proteins using low ph buffers in modified silica capillaries. Anal chem 60(21): 2322-2328 (1988).
McPhalen, C.A., et al. Structural comparison of two serine proteinase-protein inhibitor complexes: Eglin-C-subtilisin carlsberg and CI-2-subtilisin novo. Biochemistry 27(17):6582-6598 (1988).
Mendis, E, et al. Investigation of jumbo squid (*Dosidicus gigas*) skin gelatin peptides for their in vitro antioxidant effects. Life sci 77: 2166-2178 (2005).
Merzouk, A., et al. Anticancer effects of medical Malaysian leech saliva extract (LSE). Pharma anal acta. 15: 1-5 (2012).
Michalsen, A., et al. Medicinal leech therapy. Stuttgart (2007).
Mittl, P.R.E., et al. A new structural class of serine protease inhibitors revealed by the structure of the Hirustasin-Kallikrein complex. Structure 5(2): 253-264 (1997).
Mittler, T. E., et al. Differences in the probing responses of *Myzus persicae* (Sulzer) elicited by different feeding solutions behind a parafilm membrane. Entomologia experimentalis et applicata 8(2) (1965).
Montes, C., et al. Maintenance of a laboratory colony of *Cimex lectularius* (Hemiptera: Cimicidae) using an artificial feeding technique. Journal of medical entomology 39(4): 675- 679 (2002).
Moore, J. P. Leeches (Hirudinea) principally from the malay peninsula, with descriptions of new species. Bulliten of the Raffles Museum 14: 64-80 (1938).
Moser, M., et al. Bdellastasin, a serine protease inhibitor of the antistasin family from the medical leech (*Hirudo medicinalis*) primary structure, expression in yeast, and characterisation of native and recombinant inhibitor. European journal of biochemistry 253(1): 212-220 (1998).
Munro, R., et al. Calin—a platelet adhesion inhibitor from the saliva of the medicinal leech. Blood coagulation & fibrinolysis 2(1): 179-184 (1991).
Munshi, Y., et al. Leeching in the history—A review. Pakistan journal of biological sciences 11(13): 1650-1653 (2008).
Murty, V.L.N., et al. Lipid composition of squirrel monkey (*Saimiri sciureus*) saliva. Comp biochem physiol B 81(4): 823-826 (1985).
Muszbek, L., et al. Kinetic determination of blood coagulation factor xiii in plasma. Clin chem 31(1): 35-40 (1985).
Neumann, M., et al. Heavy metal ions inhibit Molybdoenzyme activity by binding to the dithiolene moiety of Molybdopterin in *Escherichia coli*. The FEBS Journal 275(22): 5678-5689 (2008).
Nobili, S., et al. Natural compounds for cancer treatment and prevention. Pharmacol res 59: 365-378 (2009).

(56) References Cited

OTHER PUBLICATIONS

Nowak, G. Pharmacology of recombinant Hirudin. Semin thromb hemost 28(5): 415-424 (2002).

Nutt, E., et al. The amino acid sequence of antistasin, a potent inhibitor of factor Xa reveals a repeated internal structure. The journal of biological chemistry 263(21): 10162-10167 (1988).

www.nsf.gov, Counting cells with hemocytometer. National science foundation, October, 2 pages (2006).

Orevi, M., et al. A potent inhibitor of platelet activating factor from the saliva of the leech *Hirudo medicinalis*. Prostaglandinis 43(5): 483-495 (1992).

Pantoja-Uceda, D., et al. Deciphering the structural basis that guides the oxidative folding of leech-derived tryptase inhibitor. J biol chem 284(51): 35612-35620 (2009).

Phillips, A.J., et al. Poly-paraphyly of Hirudinidae: Many lineages of medicinal leeches. BMC evolutionary biology 9(246) 11 pages (2009).

Pohlig, G., et al. Purificiation, characterization and biological evaluation of recombinant leech-derived Tryptase Inhibitor (rLDTI) expressed at high level in the yeast *Saccharomyces cerevisiae*. Eur J Biochem 241(2): 619-626 (1996).

Porshinsky, B.,et al. Clinical uses of the medicinal leech: A practical review. Journal of postgraduate medicine 57(1): 65-71 (2011).

Promega, celltiter-glo luminescent cell viability assay technical bulletin. Promega 13 pages (2009).

Puertas, J-M., et al. Engineering an efficent secretion of leech carboxypeptidase inhibitor in *Escherichia coli*. Microb Cell Fact 8(57) 6 pages (2009).

Rabinowitz, J.L. Salivary lipid profiles of the leech (*Hirudo medincinalis*). Lipids 31(8): 887-888 (1996).

Rados, C. Beyond bloodletting: FDA gives leeches a medical makeover. FDA Consumer 38(5): 9 (2004).

Rao J., et al. Use of Hirudo Medicinails by maxillofacial surgical units in the United Kingdom: Current views and practice. Br J Oral Maxillofac surg 41: 54-55 (2003).

Ratnam, D.V., et al. Role of antioxidants in prophylaxis and therapy: A pharmaceutical perspective. J control release 113: 189-207 (2006).

Reverter, D., et al. A Carboxypeptidase inhibitor from the medical leech *Hirudo medicinalis*, isolation, sequence analysis, cDNA cloning, recombinant expression, and characterization. The journal of biological chemistry 273(49): 32927-32933 (1998).

Reverter, D., et al. Structure of a novel leech carboxypeptidase inhibitor determinied free in solution and in complex with human carboxypeptidase A2. Nat struct biol 7(4): 322-328 (2000).

Rhiouani, H., et al. Acute and sub-chronic toxicity of an aqueous extract of the leaves of *Herniaria glabra* in rodents. Journal of ethnopharmacology 118: 378-386 (2008).

Ribeiro, J.M., et al. Purification and characterization of prolixin S (Nitrophorin 2), the salivary anticoagulant of the blood-sucking bug *Rhodnius prolixus*. The biochemical journal 308 (1): 243-249 (1995).

Rigbi, M., et al. The saliva of the medicinal leech *Hirudo medinicalis*—I. Biochemical characterization of the high molecular weight fraction. Comp biochem physiol B 87B(3): 567-573 (1987).

Rigbi, M.,et al. The saliva of the medicinal leech *Hirudo medicinalis*—II. Inhibition of platelet aggregation and of leukocyte activity and examination of reputed anaesthetic effects. Comparative biochemistry and physiology part C: Comparative pharmacology 88(1): 95-98 (1987).

Rigbi, M.,et al. A specific nhibitor of bovine Factor Xa in the saliva of the medicinal leech Hirudo Medicinalis. Paper presented at the 14th International Congress of Biochemistry Prague (Jul. 10-15 1988).

Righetti, P.G., et al. Capillary electrophoresis of peptides and proteins in acidic, isoelectric buffers: recent developments. J Biochem Biophys Methods 40: 1-15 (1999).

Salzet, M. Anticoagulats and inhibitors of platelet aggregation derived from leeches. FEBS Letters 492: 187-192 (2001).

Salzet, M, et al. Theromin, a novel leech thrombin inhibitor. J Biol Chem 275(40): 30774-30780 (2000).

Salzet, M. Leech thrombin inhibitors. Curr pharm des 8(7): 493-503 (2002).

Sampath, Kumar NS, et al. Purification and biochemical characterization of antioxidant peptide from horse mackerel (*Magalaspis cordyla*) viscera protein. Peptides 32: 1496-1501 (2011).

Sanja, S.D., et al. Characterization and evaluation of antioxidant activity of portucla oleracea. International journal of pharmacy and pharmaceutical science 1(1): 74-83 (2009).

Sawyer, R.T., et al. Growth and reproduction of the giant Glossiphoniid leech *Haementeria ghilianii*. Biol Bull 160: 322-331(1981).

Sawyer, R. T. Leech biology and behavior: vol. II: Feeding Biology. Ecology, and systematics (1986).

Scacheri, E.,et al. Novel hirudin variants from the leech *Hirudinaria manillensis*. European journal of biochemistry 214(1): 295-304 (1993).

Schagger, H. Tricine-SDS-Page. Nature Protocols 1: 16-22 (2006).

Seemüller, U., et al. Structure of the elastase-cathepsin G inhibitor of the leech *Hirudo medicinalis*. Hoppe-Seyler's Zeitschrift fur Physiologische Chemie 361(12): 1841-1846 (1980).

Seemüller, U., et al. Isolation and characterisation of a low molecular weight inhibitor (of chymotrypsin and human granulocytic elastase and cathepsin G) from leeches. Hoppe-Seyler's Zeitschrift fur physiologische Chemie 358(9): 1105-1107 (1977).

Seong, L. Y., et al. Antithrombin protein from *Hirudinaria manillensis*: Preliminary studies on isolation, sequence of the antithrombin protein and cloning of the desired gene. Universiti Teknologi Malaysia. Johor Bahur, Malaysia pp. 392-397(1997).

Seymour, J.L., et al. Decorsin, a potent glycoprotein iib-iiia antagonist and platelet aggregation inhibitor from the leech Macrobdella Decora. The Journal of Biological Chemistry 265(17): 0143-10147 (1990).

Shimoyama T., et al. Effects of different combinations of gefitinib and innotecan in lung cancer cell lines expressing wild or eeletional EGFR. Lung cancer 2006 53: 13-21 (2006).

Shionoya, T. Studies in experimental extracorporeal thrombosis III. Effects of certain anticoagulants (Heparin and Hirudin) on Extracorporeal thrombosis and on the mechanism of thrombus formation. J exp med 46(6): 19-28 (1927).

Sies, H. Oxidative stress: Oxidants and antioxidants. Exp Physiol 82: 291-295 (1997).

Slomiany, B.L, et al. Role of associated and covalently bound lipids in salivary mucin Hydrophobicity: Effect of proteolysis and disulfide bridge reduction. Biochem biophys res commun 151(3): 1046-1053 (1988).

Slomiany, B.L., et al. Salivary lipids in health and disease. Prog lipid res 24: 311-324 (1985).

Smith, P.K., et al. Measurement of protein using bicinchoninic acid. Anal biochem 150(10): 76-85 (1985).

Sohn, J.H., et al. Current status of the anticoagulant hirudin: Its biotechnological production and clinical practice. Appl microbiol biotechnol 54: 606-613 (2001).

Sollner, C., et al. Isolation and characterization of Hirustasin, an antistasin-type serine-proteinase inhibitor from the medical leech *Hirudo medicinalis*. Eur j biochem 219: 937-943 (1994).

Sommerhoff, C.P.,et al. A Kazal-Type inhibitor of human mast cell tryptase: isolation from the medical leech *Hirudo medicinalis*, characterization, and sequence analysis. Biological chemistry Hoppe-Seyler 375(10): 685-694 (1994).

Srivastava, A. ,et al. A brief review on applications of leech therapy. Archives of applied science research 2: 271-274 (2010).

Steiner, V., et al. Isolation and purification of novel Hirudins from the leech *Hirudinaria manillensis* by high-performance liquid chromatography. J chromatogr 530(2): 273-282 (1990).

Steiner, V., et al. Primary structure and function of novel O-Glycosylated Hirudins from the leech *Hirudinaria manillensis*. Biochemistry 31(8): 2294-2298 (1992).

Stenn, K.S., et al. Mechanism of bovine prothrombin activation by an insoluble preparation of bovine factor $X_a$ (Thrombokinase). Biochemistry 11(24): 4502-4515 (1972).

Stone, S.R., et al. Kinetics of the Inhibition of Thrombin by Hirudin. Biochemistry 25: 4622-4628 (1986).

Strube, K. H., et al. Isolation, sequence analysis, and cloning of haemadin. An anticoagulant peptide from the Indian leech. The Journal of biological chemistry 268(12): 8590-8595 (1993).

(56) References Cited

OTHER PUBLICATIONS

Susanto, S. Leeches used to treat diabetes patients. [Online]. Indonesia: The Jakarta Post, Bantul. (2008). Available: http://www.thejakartapost.com/news/2008/04/30/leeches-used-treat-diabetes-patients.html [Accessed Oct. 9, 2011].

Svendsen, L., et al. Synthetic chromogenic substrates for determination of trypsin, Thrombin and thrombin-like enzymes. Thromb Res 1: 267-278 (1972).

Swadesh, J.K., et al. Purification and characterization of hementin, a fibrinogenolytic protease from the leech *Haementeria ghilianii*. J Chromatogr 502(2): 359-369 (1990).

Swank, R.T., et al. Molecular weight analysis of oligopeptides by electrophoresis in polyacrylamide gel with sodium dodecyl sulfate. Anal Biochem 39(2): (1971).

Szewczuk, Z., et al. Conformationally restricted thrombin inhibitors resistant to proteolytic digestion. Biochemistry 31: 9132-9140 (1992).

Szyperski, T. Transient hydrogen bonds identified on the surface of the NMR solution structure of Hirudin. Biochemistry 33: 9303-9310 (1994).

Takahashi, S., et al. Comparison of the blood coagulation profiles of ferrets and rats. J vet med sci 73(7): 953-968 (2011).

Tasiemski, A., et al. Molecular characterization of two novel antibacterial peptides indudible upon bacterial challenge in an annelid, the leech Theromyzon Tessulatum. J biol chem 279(30): 30973-30982 (2004).

Teh, J.C., et al. Performance of selected chemical compounds in eliciting feeding of asian buffalo leech, *Hirudinaria manillensis*. Journal of fisheries and aquatic science 6(7): 846-851 (2011).

Topol, E.J. Novel antithrombotic approaches to coronary artery disease. Am J cardiol 75(6): 27B-33B (1995).

Tuszynski, G.P., et al. Isolation and characterization of antistasin, an inhibitor of metastasis and coagulation. The journal of biological chemistry 262(20): 9718-9723 (1987).

Tymiak, A.A., et al. A simple and rapid screen for inhibitors of factor XIIIa. J Antibiot (Tokyo) 46(1): 204-206 (1993).

Uson, I., et al. The 1.2 a crystal structure of Hirustasin reveals the intrinsic flexibility of a family of highly disulphide-bridged inhibitors. Structure 7(1): 55-63 (1999).

Waksman, S.A., et al. Actinomyces antibioticus, a new soil organism antagonistic to pathogenic and non-pathogenic bacteria. J Bacteriol 42: 231-249 (1941).

Wallis, R.B. Hirudins: from leeches to man. Semin thromb hemost 22(2): 185-196 (1996).

Walsmann, P. Isolation and characterization of Hirudin from *Hirudo medincinalis*. Semin thromb hemost 17(2): 83-87 (1991).

Waxman, L., et al. Tick anticoagulant peptide (TAP) is a novel inhibitor of blood coagulation factor Xa. Science 248(4955): 593-596 (1990).

Weber, K., et al. The reliability of molecular weight determination by dodecyl sulfate-polyacrylamide gel electrophoresis. J biol chem 244(16): 4406-4412 (1969).

Whitaker, I.S., et al. *Hirudo medicinalis* and the plastic surgeon. British journal of plastic surgery 57: 348-353 (2004).

Whitaker, I.S., et al. Historical articale: *Hirudo medicinalis*: Ancient origins of, and trends in the use of medicinal leeches throughout history. Br J oral maxillofac surg 42: 133-137 (2004).

Whitaker, I.S., et al. By what mechanism do leeches help to salvage ischaemic tissue? A review. Br J oral maxillofac surg 43: 155-160 (2005).

Wilson, R.J., et al. An increase in activity of serotonergic retzius neurones may not be necessary for the consummatory phase of feeding in the leech *Hirudo medicinalis*. The journal of experimental biology 199(6): 1405-1414 (1996).

Yanes, O., et al. Functional screening of serine protease inhibitors in the medical leech *Hirudo medicinalis* monitored by intensity fading MALDI-TOF MS. Mol cell proteomics 4(10): 1602-1613 (2005).

Yanqin, L., et al. Coelomic fluid of the earthworm *Eisenia fetida* induces apoptosis of HeLa cells in vitro. Eur j soil biol 43: S143-S148 (2007).

Yuki, H., et al. Purification and characterization of leech hyaluronic acid-endo-beta-glucuronidase. The Journal of biological chemistry 238: 1877-1879 (1963).

Zaidi, S.M., et al. A systematice overview of the medicinal importance of sanguivoruous leeches. Altern med rev 16(1): 59-65 (Mar. 2011).

Zellner, M., et al. Quantitative validation of different protein precipitation methods in proteome analysis of blood platelets. Electrophoresis 26(12): 2481-2489 (2005).

Zhu, K., et al. Isolation and characterization of americanin, a specific inhibitor of thrombin from the salivary glands of the lone star tick *Amblyomma americanum*. Experimental parasitology 87: 30-38 (1997).

Zipser, B., et al. Structural analysis of leech galactocerebrosides using 1D and 2D NMR spectroscopy, gas chromatography—mass spectrometry, and FAB massspectrometry. Carbohydro Res 308(1-2): 47-55 (1998).

Zipser, B., et al. Cholestrol and its derivatives are the principal steroids isolated from the leech species *Hirudo medicinalis*. Comp biochem physiol C pharmacol toxicol endocrinol 120(2): 269-282 (1998).

Zoli W., et al. In vitro preclinical models for a rational design of chemotherapy combinations in human tumors. Crit rev oncol hermatol 37: 69-82 (2001).

Zokai, K., et al. Effect of Thrombin inhibitors and a glycoprotein IIb/IIIa receptor antagonist in an ex vivo human experimental Thrombosis model. Semin thromb hemost 27(5): 531-536 (2001).

Zulhisyam A.K., et al. Optimization of growth conditions of Hirudinea sp. Australian journal of basic and applied sciences 5(3): 268-275 (2011).

ANTIBACTERIAL THERAPY WITH A WHOLE, LEECH SALIVA EXTRACT

CROSS-REFERENCE TO RELATED APPLICATIONS

This application is a continuation of U.S. application Ser. No. 14/282,893, filed May 20, 2014, which is a continuation of U.S. application Ser. No. 13/624,860, filed Sep. 21, 2012, now U.S. Pat. No. 8,784,896, which claims the benefit of U.S. Provisional Application No. 61/701,735, filed on Sep. 17, 2012, each of which is hereby incorporated by reference in its entirety.

BACKGROUND

1. Field of the Invention

The teachings provided herein are generally directed to methods of isolating and using a whole-saliva leech extract in the treatment of a subject.

2. Description of the Related Art

The history of humans using leeches goes back several thousands of years, and practically all human civilizations described the use of leeches to treat different diseases. Unfortunately, due at least to a lack of understanding of the chemistries and mechanisms associated with such uses, the current state-of-the-art has not been able to successfully commercialize the use of leech saliva extracts in treating disease.

There have been attempts at sacrificing leeches to extract active compounds from the whole body of leeches, from the heads of leeches, or from their salivary glands. Much research has been directed to identifying proteins from leech saliva extracts. None of these efforts, however, have been able to reproduce the effect of using a whole, live leech, with the exception of, perhaps, the isolation and use of hirudin as an anticoagulant.

There have been attempts at not sacrificing leeches but, rather, extracting a much diluted saliva solution from a live leech. Unfortunately, these efforts have been faced with two major problems: (i) the saliva removal requires a manual squeezing of the leech and, as such, is not easily scalable; and (ii) the saliva remains dilute, which can only be used fresh, and any lyophilization attempts will reduce or completely abolish the therapeutic activity of the leech saliva extract. As such, a dose-dependent treatment, or a treatment at elevated concentrations, is not available for testing.

One of skill will appreciate (i) a method of isolating an active, refined leech saliva extract (LSE) that can be successfully stored for months, or even years; (ii) a method of re-using leeches to produce the LSE; (iii) a method of commercializing the isolation and re-use of the leeches to a scalable amount that is practical for commercialization; (iv) a method of treating a solid tumor with the LSE; (v) a method of treating a liquid tumor with the LSE; (vi) a method of treating diabetes with the LSE; (vii) a method of treating a virus with the LSE; (viii) a method of treating a parasitic disease with the LSE; (ix) a method of using the LSE as an antioxidant; and (x) a method of using the LSE as an antibacterial.

SUMMARY

The teachings provided herein are generally directed to methods of isolating and using a whole-saliva leech extract in the treatment of a subject. Pharmaceutical formulations comprising the leech extracts and a pharmaceutically acceptable carrier are provided.

The teachings include a method of removing a whole saliva from a leech. In these embodiments, the methods can include feeding a phagostimulatory agent to a leech; inducing a regurgitation in the leech, the inducing including placing the leech in an environment having a temperature of less than about 0° C.; and, collecting an unrefined, whole saliva in the regurgitation of the cooled leech.

The teachings include a method of creating a lyophilized, whole saliva extract of a leech having an improved stability. In these embodiments, the method can include feeding a phagostimulatory agent to a leech; inducing regurgitation in the leech, the inducing including placing the leech in an environment having a temperature ranging from about −5° C. to about 15° C.; collecting an unrefined, whole saliva in the regurgitation of the cooled leech; removing solid components from the unrefined, whole saliva to create a refined, whole saliva; and, lyophilizing separate volumes of the refined, whole saliva extract, the volumes not exceeding about 2 ml each.

In some embodiments, the collecting includes squeezing the leech to increase the amount of unrefined, whole saliva collected. In some embodiments, the methods further comprise revitalizing the leech by warming the leech in a water bath having a temperature ranging from about 5° C. to about 40° C. In some embodiments, the methods further comprise creating a refined, whole-saliva extract; the creating including removing solid components from the unrefined, whole saliva. In some embodiments, the methods further comprise lyophilizing separate volumes of the refined, whole saliva extract, the volumes not exceeding about 2 ml each. And, in some embodiments, the leech is *Hirudinaria manillensis*.

The teachings include a stable, lyophilized, whole-saliva extract of a leech. In these embodiments, the extract comprises a refined, whole-saliva extract of a leech lyophilized in volumes not exceeding about 2 ml each, the extract refined by removing solid components from an unrefined, whole saliva to create the refined, whole saliva; wherein, the extract has a stable activity when stored for use at a temperature below about −20° C., the extract maintaining at least 70% of the activity for at least 6 months. And, the leech can be *Hirudinaria manillensis*.

Methods of treating a subject by administering an effect amount of the leech extracts are provided. In some embodiments, the method includes treating a solid tumor, treating a liquid tumor, treating diabetes, treating a viral disease, treating a parasitic disease, treating a bacterial disease, or administering an anti-oxidant therapy. It should be appreciated that each of the treatments also relate to other conditions that may be desirable to treat in the subject.

DETAILED DESCRIPTION

Figure 1:
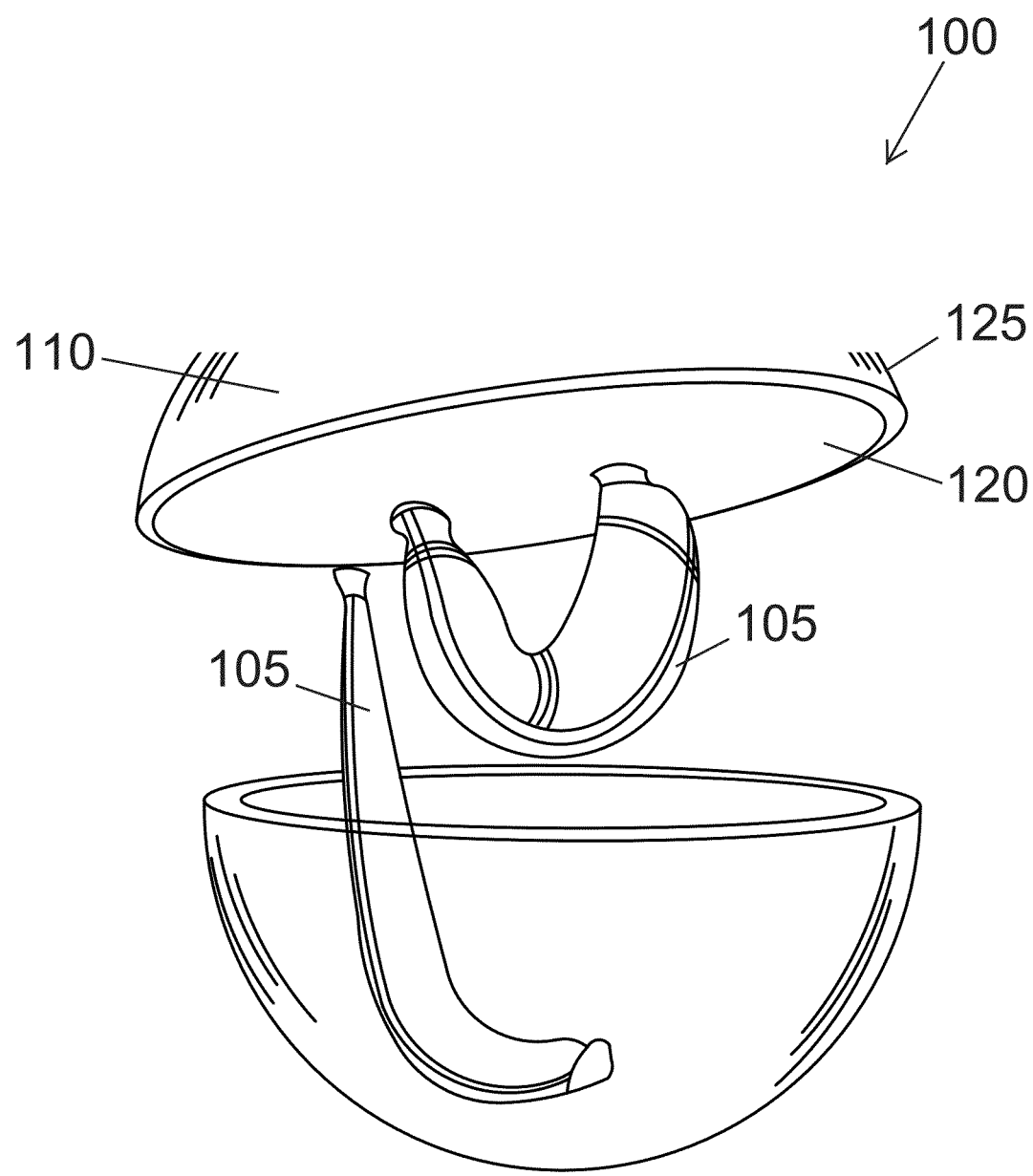
FIG. 1 illustrates a method of feeding a phagostimulatory agent to a leech using a membrane, according to some embodiments.

The teachings provided herein are generally directed to methods of isolating and using a whole-saliva leech extract in the treatment of a subject. Pharmaceutical formulations comprising the leech extracts and a pharmaceutically acceptable carrier are provided.

It should be appreciated that the term "extract" can be used to refer to a powder form of the compounds of interest, a liquid form of the compounds of interest, or any one or any combination of the compounds of interest in powder or liquid form. One of skill will appreciate that the term "extract" can be used to refer to the compounds of interest before, during, or after their removal from the leech. In some embodiments, the compounds of interest can be synthesized chemically using standard methods known to one of skill, such that they can be synthesized and used alone, or in any combination, by those of skill without use of the extraction methods taught herein. The compositions provided herein can be referred to as extracts, compositions, compounds, agents, active agents, bioactive agents, supplements, drugs, and the like. In some embodiments, the terms "LSE," "extract," "LSE composition," "composition," "compound," "agent," "active", "active agent", "bioactive agent," "supplement," and "drug" can be used interchangeably and, it should be appreciated that, a "formulation" can comprise any one or any combination of these. Likewise, in some embodiments, the composition can also be in a liquid or dry form, where a dry form can be a powder form in some embodiments, and a liquid form can include an aqueous or non-aqueous component. Moreover, the terms "activity" or "bioactivity" can refer to the function of the compound in vitro, in an assay for example, or in vivo when administered to a subject.

It should be appreciated that the leech extracts can be isolated or purified. In some embodiments, the terms "isolated" and "purified" can be used interchangeably. In some embodiments, the term "isolated" can be used to refer to the extract being removed from the natural chemical environment of the leech, such that the extract is not in the form in which it exists in nature. It should be appreciated that the term "purified" can be used to refer to an extract from a *Hirudinaria manillensis* leech, in some embodiments, such that the compounds of interest are isolated from the remainder of the leech in a form that can be administered to a subject, such as a soluble form, or a form that can go into aqueous solution. As such, one of skill will appreciate that the compounds of interest can sometimes be accompanied by other components that are carried along with the extract. For example, such other components can include any one or any combination of proteins found to be active in the leech. In some embodiments, the term "purified" can be used to refer to an extract consisting of, or consisting essentially of, any one or any combination of the compounds of interest. In some embodiments, the extract includes a phagostimulatory solution or a component from the phagostimulatory solution. In some embodiments, an extract "consists essentially of" any one or any combination of the compounds of interest, where the presence of any other component from the leech or extraction procedure has a negligible effect on the activity of the compounds of interest. The term "negligible effect" can be used to mean that the activity does not increase or decrease more than about 10% when compared to any one or any combination of the compounds of interest, respectively, without the other components. In some embodiments, the term "negligible effect" can be used to refer to a change of less that 10%, less than 9%, less than 8%, less than 7%, less than 6%, less than 5%, less than 4%, and less than 3%. In some embodiments, the term "negligible effect" can be used to refer to a change ranging from about 3% to about 10%, in increments of 1%. For example, the activity of the compounds of interest can be enhanced by an amount ranging from about 10% to about 300%, from about 20% to about 200%, from about 25% to about 250%, from about 30% to about 300%, from about 35% to about 275%, from about 40% to about 225%, from about 15% to about 100%, or any range therein in increments of 1%.

Methods of removing a whole saliva from a leech are provided. In these embodiments, the methods can include feeding a phagostimulatory agent to a leech; inducing a regurgitation in the leech, the inducing including placing the leech in an environment having a temperature of less than about 0° C.; and, collecting an unrefined, whole saliva in the regurgitation of the cooled leech.

One of skill will appreciate that any leech having a therapeutic saliva can be used in the teachings provided herein. In some embodiments, the leech can belong to the family of hirudinidae, to the sub-family hirudinariiae, or it can belong to a genus selected from the group consisting of *hirudo; hirudinaria; aliolimantis; limantis; asiaticobdella; goddardobdella; limnobdella; macrobdella; oxyptychus; philobdella.* In some embodiments, the leech can be selected from a species selected from the group consisting of *hirudo medicinalis; hirudo troctina, hirudo nipponia; hirudo orientalis; hirudo verbana; hirudinaria manillensis; hirudinaria javanica; aliolimantis africana; aliolimantis michaelseni; aliolimantis oligodonta; aliolimantis buntonesis; limantis nilotica; limantis* cf. *nilotica; limantis paluda; asiaticobdella fenestrata; goddardobdella elegans; limnobdella mexicana; macrobdella decora; macrobdella diploteria; macrobdella diletra; oxyptychus brasiliensis; oxyptychus striatus; philobdella floridana; philobdella gracilis.*

In some embodiments, the leech can belong to the family of haemadipsidae, or it can belong to a genus selected from the group consisting of *chtonobdella; haemadipsa; idiobdella; malagdbdella; nesophilaemon.* In these embodiments, the leech can be selected from a species selected from the group consisting of *chtonobdella bilineata; chtonobdella whitmani; haemadipsa interrupta; haemadipsa sylvestris; haemadipsa sumatrana; idiobdella seychellensis; malagdbdella fallax; nesophilaemon skottsbergi.*

In some embodiments, the leech can belong to the family of xerobdellidae, or it can belong to a genus selected from the group consisting of *diestecostoma; mesobdella; xerobdella.* In these embodiments, the leech can be selected from a species selected from the group consisting of *diestecostoma magna; diestecostoma mexicana; diestecostoma trujillensis; mesobdella gemmata; xerobdella lecomtei.*

In some embodiments, the leech can belong to the family of haemopidae, or it can belong to a genus selected from the group consisting of *haemopis; whitmania.* In these embodiments, the leech can be selected from a species selected from the group consisting of *haemopis grandis; haemopis kingi; haemopis sanguisuga; haemopis terrestris; whitmania laevis.*

In some embodiments, the leech can belong to the family of semiscolecidae, or it can belong to a genus selected from the group consisting of *patagoniobdella; semiscolex.* In these embodiments, the leech can be selected from a species selected from the group consisting of *patagoniobdella fraternal; patagoniobdella variabilis; semiscolex intermedius; semiscolex lamothei; semiscolex similis.*

In some embodiments, the leech can belong to the family of americobdellidae, or it can belong to a genus selected from the group consisting of *americobdella.* In these embodiments, the leech can be selected from a species selected from the group consisting of *americobdella valdiviana.*

In some embodiments, the leech can belong to the family of cylicobdellidae, or it can belong to a genus selected from the group consisting of *cylicobdella.* In these embodiments, the leech can be selected from a species selected from the group consisting of *cylicobdella coccinea.*

In some embodiments, the leech can belong to the family of erpobdellidae. In these embodiments, the leech can be selected from a species selected from the group consisting of *erpobdella mentezuma.*

The leeches can be classified according to Table 1, in some embodiments.

TABLE 1

| Family | Sub family | Genus | Species |
|---|---|---|---|
| Hirudinidae | Hirudinariinae | Hirudo | Hirudo medicinalis |
| | | | Hirudo nipponia |
| | | | Hirudo orientalis |
| | | | Hirudo troctina |
| | | | Hirudo verbana |
| | | Aliolimantis | Aliolimantis Africana |
| | | | Aliomantis michaelseni |
| | | | Aliomantis oligodonta |
| | | | Aliomantis buntonesis |
| | | Asiaticobdella | Asiaticobdella fenestrate |
| | | Goddardobdella | Goddardobdella elegans |
| | | Hirudinaria | Hirudinaria javanica |
| | | | Hirudinaria manillensis |
| | | Limantis | Limantis nilotica |
| | | | Limantis cf. nilotica |
| | | | Limantis paluda |
| | | Limnobdella | Limnobdella mexicana |
| | | Macrobdella | Macrobdella decora |
| | | | Macrobdella diploteria |
| | | | Macrobdella diletra |
| | | Oxyptychus | Oxyptychus brasiliensis |
| | | | Oxyptychus striatus |
| | | Philobdella | Philobdella floridana |
| | | | Philobdella gracilis |
| Haemadipsidae | Not applicable | Chtonobdella | Chtonobdella bilineata |
| | | | Chtonobdella whitmani |
| | | Haemadipsa | Haemadipsa interrupta |
| | | | Haemadipsa sylvestris |
| | | | Haemadipsa sumatrana |
| | | Idiobdella | Idiobdella seychellensis |
| | | Malagadbdella | Malagadbdella fallax |
| | | Nesophilaemon | Nesophilaemon skottsbergi |
| Xerobdellidae | Not applicable | Diestecostoma | Diestecostoma magna |
| | | | Diestecostoma Mexicana |
| | | | Diestecostoma trujillensis |
| | | Mesobdella | Mesobdella gemmata |
| | | Xerobdella | Xerobdella lecomtei |
| Haemopidae | Not applicable | Haemopis | haemopis grandis |
| | | | Haemopis kingi |
| | | | Haemopis sanguisuga |
| | | | Haemopis terrestris |
| | | Whitmania | Whitmania laevis |
| Semiscolecidae | Not applicable | Patagoniobdella | Patagoniobdella fraternal |
| | | | Patagoniobdella variabilis |
| | | Semiscolex | Semiscolex intermedius |
| | | | Semiscolex lamothei |
| | | | Semiscolex similis |
| Americobdellidae | Not applicable | Americobdella | Americobdella valdiviana |
| Cylicobdellidae | Not applicable | Cylicobdella | Cylicobdella coccinea |
| Erpobdellidae | Not applicable | Erpobdella | Erpobdella montezuma |

Any phagostimulatory agent known to one of skill can be used. In some embodiments, the phagostimulatory agent can include a protein, a polypeptide, an oligopeptide, or an amino acid. In some embodiments, the amino acid is an L-amino acid selected from the group consisting of arginine, alanine, leucine, aspartic acid, serine, threonine, isoleucine, histidine, lysine, tryptophan, glycine, phenylalanine, tyrosine, valine, glutamic acid, asparagine, glutamine, cysteine, methionine, and proline. In some embodiments, the phagostimulatory agent is arginine. In some embodiments, the phagostimulatory agent is glycine. In some embodiments, the phagostimulatory agent is proline. In some embodiments, the phagostimulatory agent is a sugar. In some embodiments, the phagostimulatory agent is a sugar selected from the group consisting of fructose, glucose, sucrose, maltose, raffinose, trehalose, robose, and galactose. In some embodiments, the phagostimulatory agent is corn oil. In some embodiments, the phagostimulatory agent comprises any one or any combination of amino acids and/or sugars taught herein. Any suitable solvent for carrying the phagostimulatory can be used, polar or non-polar, as long as the solvent does not substantially affect the activity or stability of the leech saliva extract.

The temperature of the leech that induces the regurgitation can range from about −5° C. to about 15° C., from about −4° C. to about 14° C., from about −3° C. to about 13° C., from about −2° C. to about 12° C., from about −1° C. to about 11° C., from about 0° C. to about 10° C., from about −2° C. to about 2° C., from about −3° C. to about 3° C., from about −4° C. to about 4° C., from about −5° C. to about 5° C., or any temperature or range of temperatures therein in increments of 1° C. The temperature can be established using any method known to one of skill. In some embodiments, the temperature is established to 0° C. or about 0° C. using an ice water bath. In some embodiments, a salt water bath can be used to lower the temperature below 0° C., and in some embodiments, other liquids can be used to obtain other temperatures. Any method of cooling know to one of skill can be used to induce the leeches to vomit. The rate of freezing can be 0.1 to 2° C. per minute and, in some embodiments, 1° C. to 1.5° C. per minute. The time at the cool temperature can vary and can be, for example, from about 5 minutes to about 45 minutes, from about 15 minutes to about 40 minutes, from about 15 minutes to about 20 minutes, from about 10 minutes to about 30 minutes, from about 5 minutes to about 25 minutes, from about 3 minutes to about 35 minutes, from about 2 minutes to about 12 minutes, or any time or range times therein in increments of 1 minute.

Methods of creating a lyophilized, whole saliva extract of a leech having an improved stability are provided by the teachings herein. In these embodiments, the method can include feeding a phagostimulatory agent to a leech; inducing regurgitation in the leech, the inducing including placing the leech in an environment having a temperature ranging from about −5° C. to about 15° C.; collecting an unrefined, whole saliva in the regurgitation of the cooled leech; removing solid components from the unrefined, whole saliva to create a refined, whole saliva; and, lyophilizing separate volumes of the refined, whole saliva extract, the volumes not exceeding about 2 ml each.

In some embodiments, the collecting includes squeezing the leech to increase the amount of unrefined, whole saliva collected. In some embodiments, the methods further comprise revitalizing the leech by warming the leech in a water bath having a temperature ranging from about 5° C. to about 40° C. In some embodiments, the methods further comprise creating a refined, whole-saliva extract; the creating including removing solid components from the unrefined, whole saliva. In some embodiments, the methods further comprise lyophilizing separate volumes of the refined, whole saliva extract, the volumes not exceeding about 2 ml each. And, in some embodiments, the leech is *Hirudinaria manillensis*.

Stable, lyophilized, whole-saliva extracts of a leech are provided by the teachings herein. In these embodiments, the extract comprises a refined, whole-saliva extract of a leech lyophilized in volumes not exceeding about 2 ml each, the extract refined by removing solid components from an unrefined, whole saliva to create the refined, whole saliva; wherein, the extract has a stable activity when stored for use at a temperature below about −20° C., the extract maintaining at least 70% of the activity for at least 6 months. And, the leech can be *Hirudinaria manillensis*.

Storage temperature has been shown in some embodiments herein to have a large effect on the stability of the extracts. In some embodiments, for example, the refined, whole saliva can be stored at a temperature ranging from 0° C. to −80° C., from −20° C. to −270° C., from −20° C. to −196° C., from −20° C. to −80° C., from −80° C. to −196° C., or any temperature, or any range therein in increments of 1° C.

One of skill will appreciate that the extracts can vary in stability, but that the teachings provided herein show extracts with increased stabilities when compared to the current state-of-the-art. One of skill will appreciate that the compositions or formulations should remain stable, or at least substantially stable, until used or activated, and this can relate to a shelf life, or a time between creation and administration of the composition, or some combination thereof. In some embodiments, the composition is stable, or substantially stable, when usable as intended within a reasonable amount of time, a time that is considered reasonable by one of skill for the applications taught herein. In some embodiments, the composition should be usable within a reasonable time from the making to the administration of the composition and, in some embodiments, the composition should have a reasonable commercial shelf life, a shelf life that is considered reasonable to one of skill. A reasonable shelf life can be at least 6 months, at least 1 year, at least 18 months, at least 2 years, at least 3 years, or any time in-between in increments of about 1 month, in some embodiments.

In some embodiments, a composition or formulation can be considered as "stable" if it loses less than 10%, less than 7%, less than 6%, less than 5%, less than 3%, less than 2%, or less than 1% of its original activity. In some embodiments, a composition or formulation can be considered as "substantially stable" if it loses greater than about 10% of its original activity, as long as the composition can perform it's intended use to a reasonable degree of efficacy. In some embodiments, the composition can be considered as substantially stable if it loses activity at an amount greater than about 12%, about 15%, about 25%, about 35%, about 45%, about 50%, about 60%, or even about 70%. The activity loss can be measured by comparing activity at the time of packaging to the activity at the time of administration, and this can include a reasonable shelf life. In some embodiments, the composition is stable or substantially stable, if it remains useful for a period ranging from 3 months to 3 years, 6 months to 2 years, 1 year, or any time period therein in increments of about 1 month.

Methods of Treatment

Methods of treating a subject by administering an effect amount of the leech extracts are provided by the teachings herein. The extracts taught herein can be used for a variety of treatments, preventative, ameliorative, or otherwise, as well as for use as a dietary supplement. The uses can include medicinal purposes, as a health supplement, a nutritional composition, a prophylactic, or a treatment of an existing condition. In some embodiments, any tissue that can make contact with one or more active components of an extract taught herein can be treated. In some embodiments, a tissue can have a desirable secondary effect from one or more of the active components of an extract taught herein making contact elsewhere in the subject, such that one or more of the active components can contact a first tissue, whereas a second tissue realizes a beneficial effect. For example, the first tissue can be a stomach lining, and the second tissue can realize the desirable effect of a release of a neurotransmitter or a neuroimpulse. The tissue can be, for example, connective, muscle, nervous, and/or epithelial tissue. In some embodiments, the tissue is a dermal tissue. In some embodiments, the tissue is a mucosal tissue. And, in some embodiments, the tissue is gastrointestinal tissue. In some embodiments, the method includes treating a solid tumor, treating a liquid tumor, treating diabetes, treating a viral disease, treating a parasitic disease, administering an anti-oxidant therapy, or administering an antibacterial therapy.

As such, the subject can have a target tissue that is the focus of the treatment in which the extracts are applied directly or systemically. In some embodiments, the term "target site" can be used to refer to a select location on or in a subject that could benefit from an administration of a compound taught herein, either parenterally or non-parenterally, whether injected or administered topically or orally, for example. In some embodiments, a target can include any site of action in which the agent's activity can serve a benefit to the subject. The target site can be a healthy or damaged tissue of a subject. As such, the teachings include a method of administering one or more compounds taught herein to a healthy or damaged tissue, dermal, mucosal, gastrointestinal or otherwise.

The terms "treat," "treating," and "treatment" can be used interchangeably in some embodiments and refer to the administering or application of the compositions and formulations taught herein, including such administration as a health or nutritional supplement, and all administrations directed to the prevention, inhibition, amelioration of the symptoms, or even a cure of a condition taught herein. The terms "disease," "condition," "disorder," and "ailment" can be used interchangeably in some embodiments.

The term "subject" and "patient" can be used interchangeably in some embodiments and refer to an animal such as a mammal including, but not limited to, non-primates such as, for example, a cow, pig, horse, cat, dog, rat and mouse; and primates such as, for example, a monkey or a human. As such, the terms "subject" and "patient" can also be applied to non-human biologic applications including, but not limited to, veterinary, companion animals, commercial livestock, and the like.

Treatment of Cancer

The LSE taught herein can be used in the treatment of cancer. In some embodiments, the methods include treating a solid tumor and, in some embodiments, the methods include treating a liquid tumor. One of skill will appreciate that the cancers that can be treated using the methods taught herein can include any hyperproliferative tissue. In some embodiments, for example, any cancer listed in Table 2 can be treated using the methods taught herein.

TABLE 2

| Cell line | Cancer type | Cancer Sub-type |
|---|---|---|
| CCRF-CEM | Leukemia | Acute Lymphoblastic Leukemia (ALL) |
| HL-60 (TB) | Leukemia | Acute Myelogenous Leukemia (AML) |
| K-562 | Leukemia | Chronic Myelogenous leukemia (CML) |
| MOLT-4 | Leukemia | Acute Lymphoblastic Leukemia (ALL) |
| RPMI-8226 | Multiple Myeloma | Plasmacytoma, myeloma |
| SR | Leukemia | Acute Lymphoblastic Leukemia (ALL) |
| A549/ATCC | Non-small cell lung | Adinocarcinoma |
| EKVX | Non-small cell lung | Adinocarcinoma |
| HOP-62 | Non-small cell lung | Adinocarcinoma |
| HOP-92 | Non-small cell lung | Adinocarcinoma |

TABLE 2-continued

| Cell line | Cancer type | Cancer Sub-type |
|---|---|---|
| NCI-H226 | Non-small cell lung | Squamous Carcinoma |
| NCI-H23 | Non-small cell lung | Adinocarcinoma |
| NCI-H322M | Non-small cell lung | Bronchioloalveolar Carcinoma |
| NCI-H460 | Non-small cell lung | Adinocarcinoma |
| NCI-H522 | Non-small cell lung | Adinocarcinoma |
| COLO 205 | Colon | Adinocarcinoma |
| HCC-2998 | Colon | Adinocarcinoma |
| HCT-116 | Colon | Carcinoma |
| HCT-15 | Colon | Adinocarcinoma |
| HT-29 | Colon | Adinocarcinoma |
| KM12 | Colon | Colorectal |
| SW-620 | Colon | Adinocarcinoma |
| SN-268 | CNS | Glioblastoma |
| SF-295 | CNS | Glioblastoma |
| SF-539 | CNS | Gliosarcoma |
| SNB-19 | CNS | Glioblastoma |
| SNB-75 | CNS | Glioblastoma |
| LOX IMVI | Skin Cancer | Melanoma |
| MALME-3M | Skin Cancer | Melanoma |
| M14 | Skin Cancer | Melanoma, amelanotic |
| SK-MEL-2 | Skin Cancer | Melanoma, malignant |
| SK-MEL-28 | Skin Cancer | Melanoma, malignant |
| SK-MEL-5 | Skin Cancer | Melanoma, malignant |
| UACC-257 | Skin Cancer | Melanoma |
| UACC-62 | Skin Cancer | Melanoma |
| IGROVI | Ovarian | Adinocarcinoma |
| OVCAR-3 | Ovarian | Adinocarcinoma |
| OVCAR-4 | Ovarian | Carcinoma |
| OVCAR-5 | Ovarian | Carcinoma |
| OVCAR-8 | Ovarian | Carcinoma |
| SK-OV-3 | Ovarian | Adinocarcinoma |
| 786-0 | Renal | Carcinoma |
| A498 | Renal | Carcinoma |
| ACHN | Renal | Adinocarcinoma |
| CAKI-1 | Renal | Carcinoma |
| RXF-393 | Renal | Carcinoma |
| SN12C | Renal | Carcinoma |
| TK-10 | Renal | Carcinoma |
| UO-31 | Renal | Carcinoma |
| PC-3 | Prostate | Adinocarcinoma |
| DU-145 | Prostate | Carcinoma |
| MCF7 | Breast | Adinocarcinoma |
| NCI/ADR-RES | Breast | Adinocarcinoma |
| MDA-MB-231/ATCC | Breast | Adinocarcinoma |
| HS 578T | Breast | Carcinosarcoma |
| MDA-MB-435 | Breast | Carcinoma, ductal |
| MDA-MB-468 | Breast | Adinocarcinoma |
| BT-549 | Breast | Carcinoma |
| T-47D | Breast | Carcinoma, ductal |

Treatment of Diabetes

The LSE taught herein can be used in the treatment of diabetes. Examples of diabetes include Type 1-, Type 2-, and gestational diabetes. As such, one of skill will appreciate that the LSE taught herein can be used in treating and preventing metabolic imbalances, diabetes mellitus, a pre-diabetic state, metabolic syndrome, and other related disorders, such as Latent Autoimmune Diabetes in adults (referred to as Type 1.5 diabetes). As such, secondary medical conditions related to diabetes can also be treated using the LSE taught herein, indirectly or directly, including heart disease, stroke, high blood pressure, eye complications (retinopathy, cataracts), kidney disease (nephropathy), nervous system disease (neuropathy), peripheral vascular disease, dental disease, gastroparesis, sexual dysfunction, and complications during pregnancy.

The term "diabetic" in a rat can refer to a random blood glucose>225 mg/dl or fasting blood glucose level of >110 mg/dL. The term "diabetic" in a human can refer to a random plasma or blood glucose concentration of $\geq 200$ mg/dL ($\geq 11.1$ mmol/L) or a fasting plasma glucose$\geq 126$ mg/dL ($\geq 7.0$ mmol/L) or a 2 hour post-load glucose$\geq 200$ mg/dL ($\geq 11.1$ mmol/L) during an oral glucose tolerance test. The term "non-diabetic" in a rat generally means a fasting plasma glucose level of ≤80 mg/dL or a random plasma glucose level<200 mg/dL. The term "non-diabetic" in a human can refer to a fasting plasma glucose level of <100 mg/dL (5.6 mmol/dL) or a 2 hour post-load glucose<140 mg/dL (<7.8 mmol/dL) during an oral glucose tolerance test. The term "pre-diabetic" in a rat can refer to a fasting plasma glucose level of about 80 to about 110 mg/dL. The term "pre-diabetic" in a human can refer to a fasting plasma glucose level of 100-125 mg/dL (5.6-6.9 mmol/L) or a 2 hour post-load glucose 140-199 mg/L (7.8-11.1 mmol/L) during an oral glucose tolerance test. The terms "random" and "nonfasting" can be used in reference to any time of day or night without regard to time since the last meal, and the term "fasting" generally means no caloric intake for at least 12 hours. The term "metabolic imbalance" can refer any condition associated with an elevated plasma glucose. A metabolic imbalance, for example, comprises diabetes mellitus, gestational diabetes, genetic defects of .beta.-cell function, genetic defects in insulin action, diseases of the exocrine pancreas, endocrinopathies, drug or chemical-induced, infections, other genetic syndromes associated with diabetes, a pre-diabetic state, and metabolic syndrome. The term "metabolic syndrome" can refer to a group of metabolic risk factors in one person including, but not limited to, abdominal obesity, atherogenic dyslipidemia, hypertension, insulin resistance or glucose intolerance, prothrombotic state (high fibrinogen or plasminogen activator inhibitor-1), and proinflammatory state (elevated C-reactive protein). In some embodiments, metabolic syndrome be the presence of three or more of the following components: elevated waist circumference (males: ≥40 inches, females≥35 inches), fasting triglycerides≥150 mg/dL, reduced HDL (males: <40 mg/dL, females<50 mg/dL), blood pressure≥130/85 mm Hg, and fasting glucose≥100 mg/dL.

The above definitions for diabetes follow standards of the American Diabetes Association (ADA), the American Heart Association (AHA) and the National Heart, Lung, and Blood Institute. Other definitions can be used and may vary by region or country, and may depend upon the group or institution (e.g. ADA, World Health Organization (WHO), National Institute of Diabetes and Digestive and Kidney Diseases (NIDDK/NIH), Center for Disease Control (CDC), etc.) providing other guidelines. Physicians may also use clinical experience, a patient's past medical history, and the like when deciding on a diagnosis and treatment. As such, one of skill will appreciate that the particular ranges and measures are merely relative rather than critical to making a diagnosis or planning a treatment. In some embodiments, for example, any of the above measures can vary by about 1%, about 2%, about 3%, about 5%, about 7%, about 10%, about 15%, about 20%, about 25%, about 30%, 40%, 50%, or any range or amount therein in increments of 0.1%.

Treatment of a Viral Disease

The LSE taught herein can be used in the treatment of several different types of viral diseases. In some embodiments, the virus can be a species of *Adenoviridae, Herpesviridae, Papillomaviridae, Polyomaviridae, Poxyiridae, Hepadnaviridae, Parvoviridae, Astroviridae, Caliciviridae, Picornaviridae, Coronaviridae, Flaviviridae, Togaviridae, Retroviridae, Orthomyxoviridae, Arenaviridae, Bunyaviridaem, Filoviridae, Paramyxoviridae, Rhabdoviridae,* or *Reoviridae.*

In some embodiments, the species of virus treated can be selected from the group consisting of Adenovirus, Herpes simplex, type 1, Herpes simplex, type 2, Varicella-zoster virus, Epstein-barr virus, Human cytomegalovirus, Human herpesvirus, type 8, Human papillomavirus, BK virus, JC virus, Smallpox, Hepatitis B virus, Human bocavirus, Parvovirus B19, Human astrovirus, Norwalk virus, coxsackievirus, hepatitis A virus, poliovirus, rhinovirus, Severe acute respiratory syndrome virus, Hepatitis C virus, yellow fever virus, dengue virus, West Nile virus, Rubella virus, Hepatitis E virus, and Human immunodeficiency virus (HIV).

In some embodiments, the viral condition can be a regionally identified condition selected from the viral conditions in Table 3:

TABLE 3

| Australia | Hong Kong | Malaysia | United Kingdom | United States |
|---|---|---|---|---|
| Acquired Immunodeficiency Syndrome (AIDS) | | Acquired immunodeficiency syndrome | | |
| Arbovirus infections: Barmah Forest, Dengue fever, Japanese encephalitis, Kunjin virus, Murray Valley encephalitis virus, Ross River virus | Arbovirus infections: West Nile virus | | | Arbovirus infections: California serogroup virus, Eastern equine encephalitis virus, Powassan virus, St. Louis encephalitis virus, West Nile virus, Western equine encephalitis virus |
| | Chickenpox | | | Chickenpox (i.e., varicella) - morbidity and deaths only |
| | | Chikungunya fever | | |
| | Dengue fever | Dengue fever | | Dengue fever |
| | | Enterovirus 71 infection | | |
| | Hantavirus infection | | | Hantavirus |
| Hepatitis | | Hepatitis | Hepatitis | |
| Hepatitis A | Hepatitis A | | | Hepatitis A |
| Hepatitis B | Hepatitis B | | | Hepatitis B |

TABLE 3-continued

| Australia | Hong Kong | Malaysia | United Kingdom | United States |
|---|---|---|---|---|
| Hepatitis C | Hepatitis C | | | Hepatitis C |
| Hepatitis D | Hepatitis D | | | |
| Hepatitis E | Hepatitis E | | | |
| Human immunodeficiency virus (HIV) infection | | | Human immunodeficiency virus (HIV) infection | HIV infection |
| Influenza | Influenza A (H2), Influenza A (H5), Influenza A (H7) or Influenza A (H9) | | | Influenza-associated pediatric mortality and novel influenza A infection |
| | Japanese encephalitis | | | |
| Lyssavirus | | | | |
| Measles | Measles | Measles | Measles | Measles |
| Mumps | Mumps | | Mumps | Mumps |
| Poliomyelitis | Acute poliomyelitis | Poliomyelitis | Poliomyelitis | Poliomyelitis, paralytic and non-paralytic |
| | Rabies | Rabies | Rabies | Rabies |
| Rubella | Rubella and congenital rubella syndrome | | Rubella | Rubella |
| | Severe Acute Respiratory Syndrome | | Severe Acute Respiratory Syndrome | Severe Acute Respiratory Syndrome |
| Smallpox | Smallpox | | Smallpox | Smallpox |
| Yellow fever | Yellow fever Viral haemorrhagic fever | Yellow fever Viral hemorrhagic fever, including Lassa fever, Marburg virus, and Ebola virus | Yellow fever Viral hemorrhagic fever | Yellow fever Viral hemorrhagic fever, including Arenavirus (new world), Crimean-Congo hemorrhagic fever, Dengue hemorraghic fever, Ebola virus, Lassa virus, Marburg virus |

In some embodiments, the compositions taught herein can be administered with a second agent, such as abacavir, aciclovir, acyclovir, adefovir, amantadine, amprenavir, ampligen, arbidol, atazanavir, atripla, aoceprevir, cidofovir, combivir, darunavir, delavirdine, didanosine, docosanol, edoxudine, efavirenz, emtricitabine, enfuvirtide, entecavir, entry inhibitors, famciclovir, fomivirsen, fosamprenavir, foscarnet, fosfonet, fusion inhibitor, ganciclovir, ibacitabine, immunovir, idoxuridine, imiquimod, indinavir, inosine, integrase inhibitor, interferon type III, interferon type II, interferon type I, interferon, lamivudine, lopinavir, loviride, maraviroc, moroxydine, methisazone, nelfinavir, nevirapine, nexavir, oseltamivir, peginterferon alfa-2a, penciclovir, peramivir, pleconaril, podophyllotoxin, protease inhibitor. Raltegravir, reverse transcriptase inhibitor, ribavirin, rimantadine, ritonavir, pyramidine, saquinavir, stavudine, synergistic enhancer (antiretroviral), tea tree oil, telaprevir, tenofovir, tenofovir disoproxil, tipranavir, trifluridine, trizivir, tromantadine, truvada, valaciclovir, valganciclovir, vicriviroc, vidarabine, viramidine, zalcitabine, zanamivir, and zidovudine.

Treating a Parasitic Disease

The LSE taught herein can be used in the treatment of several different types of parasitic diseases. In some embodiments, the parasitic disease treated can be classed as a condition caused by protozoa (causing protozoan infection), helminths (helminthiasis), and ectoparasites.

In some embodiments, the parasitic disease can be selected from the group consisting of Acanthamoeba keratitism, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis (caused by the Guinea worm), Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis (cause of Cysticercosis), Toxocariasis, Toxoplasmosis, Trichinosis, and Trichuriasis.

In some embodiments, the compositions taught herein can be administered with a second agent, such as thiabendazole, pyrantel pamoate, mebendazole, praziquantel, niclosamide, bithionol, oxamniquine, metrifonate, Ivermectin, albendazole, benznidazole, nifurtimox, and nitroimidazole.

Treatment of a Bacterial Disease

The LSE taught herein can be used in the treatment of several different types of bacterial diseases. In some embodiments, the bacterial disease can include, for example, tuberculosis from *Mycobacterium tuberculosis*; pneumonia from *Streptococcus* and *Pseudomonas*; a foodborne illness from

*Shigella, Campylobacter,* or *Salmonella*; and, either tetanus, typhoid fever, diphtheria, syphilis, or leprosy. In some embodiments, the bacterial disease can be a bacterial vaginosis; bacterial meningitis; bacterial pneumonia; urinary tract infection, including *E. coli.* Infections; bacterial gastroenteritis, also including *E. coli*; and, bacterial skin infections, including impetigo from *S. aureus* and *S. pyogenes*, Erysipelas from *Streptococcus*, and cellulitis which can include connective tissue. In some embodiments, the bacterial disease can be selected from the group consisting of the diseases in Table 4.

TABLE 4

| Australia | Hong Kong | Malaysia | United Kingdom | United States |
|---|---|---|---|---|
|  |  |  |  | Anaplasmosis |
|  | Anthrax |  | Anthrax | Anthrax |
| Botulism | Botulism |  | Botulism | Botulism |
| Brucellosis |  |  | Brucellosis | Brucellosis |
| Campylobacteriosis |  |  |  |  |
|  |  |  |  | Chancroid |
| Chlamydia |  |  |  | Chlamydia trachomatis |
| Cholera | Cholera | Cholera | Cholera | Cholera |
| Diphtheria | Diphtheria | Diphtheria | Diphtheria | Diphtheria |
| Donovanosis |  |  |  |  |
|  |  |  |  | Ehrlichiosis |
| Shiga toxin- and verocytotoxin-producing *Escherichia coli* (STEC/VTEC) | *Escherichia coli* O157:H7 infection |  |  | *Escherichia coli* O157:H7 or Shiga-toxin producing *Escherichia coli* |
|  |  | Encephalitis | Encephalitis |  |
| Gonococcal infection |  | Gonococcal infection/Gonorrhea |  | Gonorrhea |
| Haemolytic uraemic syndrome (HUS) |  |  | Haemolytic uraemic syndrome (HUS) | Hemolytic uremic syndrome, post-diarrheal |
| Haemophilus influenzae serotype b (Hib) | Haemophilus influenzae type b infection (invasive) |  |  | Haemophilus influenzae, invasive disease |
| Legionellosis | Legionnaire's Disease |  | Legionnaire's Disease | Legionellosis |
| Leprosy | Leprosy | Leprosy | Leprosy | Hansen's disease (Leprosy) |
| Leptospirosis | Leptospirosis |  |  |  |
| Listeriosis | Listeriosis |  |  | Listeriosis |
|  |  |  |  | Lyme disease |
| Meningococcal disease | Meningococcal infection (invasive) |  | Meningococcal septicaemia/ Acute Meningitis | Meningococcal disease |
|  | MSRA: Community-associated methicillin-resistant *Staphylococcus aureus* infection |  |  |  |
|  | Paratyphoid fever | Paratyphoid fever | Paratyphoid fever |  |
| Pertussis (Whooping cough) | Pertussis (Whooping cough) | Pertussis (Whooping cough) | Pertussis (Whooping cough) |  |
| Plague | Plague (bubonic, septicemic, pneumonic and pharyngeal) | Plague | Plague | Plague (bubonic, septicemic, pneumonic and pharyngeal) |
| Psittacosis | Psittacosis |  |  | Psittacosis |
| Q fever | Q fever |  |  | Q Fever, acute and chronic |
|  | Relapsing fever | Relapsing fever |  |  |
|  |  | Rickettsiosis |  | Rickettsiosis, spotted fever |
|  | Scarlet fever |  | Scarlet fever |  |

TABLE 4-continued

| Australia | Hong Kong | Malaysia | United Kingdom | United States |
|---|---|---|---|---|
| Salmonellosis | | | | Salmonellosis |
| Shigellosis | Bacillary dysentery | | | Shigellosis |
| | | | Group A Streptococcal disease | Group A Streptococcal disease |
| Pneumococcal disease | | | | *Streptococcus pneumoniae*, invasive disease |
| | Streptococcus suis infection | | | |
| Syphilis | | Syphilis | | Syphilis |
| Tetanus | Tetanus | Tetanus | Tetanus | Tetanus |
| | | | | Toxic shock syndrome (Streptococcal and other than Streptococcal) |
| Tuberculosis | Tuberculosis | Tuberculosis | Tuberculosis | Tuberculosis, *Mycobacterium tuberculosis* |
| Tularemia | | | | Tularemia |
| Typhoid fever | Typhoid fever Typhus and other rickettsial diseases | Typhoid fever Typhus | Typhoid fever Typhus | Typhoid fever |
| | | | | Vancomycin Intermediate *Staph Aureus* (VISA), Vancomycin Resistant *Staph Aureus* (VRSA) |

Administering an Anti-Oxidant Therapy

The LSE taught herein can be used in antioxidant therapy. One of skill will appreciate that reactive oxygen species (ROS) are widely believed to cause or aggravate several human pathologies such as arthritis, neurodegenerative diseases, cancer, heart disease, stroke and many other ailments. Antioxidants can be used to counteract the harmful effects of ROS and therefore prevent or treat oxidative stress-related diseases. In some embodiments, the LES taught herein can be used as a free radical scavenger, or to prevent oxidation in the body. In some embodiments, the LES taught herein can be used to treat inflammatory disorders, endocrine disorders, cardiovascular disease, aging, as well as to serve as a neuroprotective agent. In some embodiments, the LES taught herein can be used to treat atherosclerosis. And, in some embodiments, the LES can be administered in combination with a cholesterol medication such as an absorption blocker, a synthesis inhibitors and a niacin-based drug. In some embodiments, a non-drug alternative can be used, such as beta-glucan from whole oats or barley; psyllium from wheat bran; or, phytosterols and/or phytostanols.

In some embodiments, the absorption blocker can be cholestyramine or ZETIA. In some embodiments, the synthesis inhibitor can be a statin including, but not limited to, MEVACOR, PRAVACHOL, ZOCOR, LIPITOR, LESCOL, CRESTOR, or LIVALO. In some embodiments, the synthesis inhibitor can be LOVASTATIN, PRAVASTATIN, or SIMVASTATIN. In some embodiments, the niacin-based medication can be NIASPAN or NIACOR. In some embodiments, the cholesterol medication can be a combination product such as MEVACOR with NIASPAN, or ZETIA with ZOCOR.

Methods of Administration

Any administration vehicle known to one of skill to be suitable for administration of the compounds, compositions, and formulations taught herein can be used. A "vehicle" can refer to, for example, a diluent, excipient or carrier with which a compound is administered to a subject.

The terms "administration" or "administering" can be used to refer to a method of incorporating a composition into or onto the cells or tissues of a subject, either in vivo or ex vivo to test the activity of a system, as well as to diagnose, prevent, treat, or ameliorate a symptom of a disease or condition. In one example, a compound can be administered to a subject in vivo using any means of administration taught herein. In another example, a compound can be administered ex vivo by combining the compound with cell tissue from the subject for purposes that include, but are not limited to, assays for determining utility and efficacy of a composition. And, of course, the compositions can be used in vitro to test their stability, activity, toxicity, efficacy, and the like. When the compound is incorporated in the subject in combination with one or active agents, the terms "administration" or "administering" can include sequential or concurrent incorporation of the compound with the other agents such as, for example, any agent described above. A composition can be formulated, in some embodiments, to be compatible merely with its intended route of administration.

Any dosage form known to one of skill can be used for administrations that include, for example, parenteral and non-parenteral administrations. In some embodiments, the composition is in a dosage form for administration topically. And, in some embodiments, the composition is in a dosage form for administration orally. In some embodiments, the dosage form can be a capsule or an injectable fluid. The composition can also be used as a dietary supplement. The term "dosage unit" can refer to discrete, predetermined quantities of a compound that can be administered as unitary dosages to a subject. A predetermined quantity of active compound can be selected to produce a desired therapeutic effect and can be administered with a pharmaceutically acceptable carrier. The predetermined quantity in each unit dosage can depend on factors that include, but are not limited to, (a) the unique characteristics of the active compound and the particular therapeutic effect to be achieved, and (b) the limitations inherent in the art of creating and administering such dosage units.

A "pharmaceutically acceptable carrier" is a diluent, adjuvant, excipient, or vehicle with which the composition is administered. A carrier is pharmaceutically acceptable after approval by a state or federal regulatory agency or listing in the U.S. Pharmacopeial Convention or other generally recognized sources for use in subjects. The pharmaceutical carriers include any and all physiologically compatible solvents, dispersion media, coatings, antibacterial and antifungal agents, isotonic and absorption delaying agents, and the like. Examples of pharmaceutical carriers include, but are not limited to, sterile liquids, such as water, oils and lipids such as, for example, phospholipids and glycolipids. These sterile liquids include, but are not limited to, those derived from petroleum, animal, vegetable or synthetic origin such as, for example, peanut oil, soybean oil, mineral oil, sesame oil, and the like.

Suitable pharmaceutical excipients include, but are not limited to, starch, sugars, inert polymers, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. In some embodiments, the composition can also contain minor amounts of wetting agents, emulsifying agents, pH buffering agents, or a combination thereof. Oral formulations, for example, can include standard carriers such as, for example, pharmaceutical grades mannitol, lactose, starch, magnesium stearate, sodium saccharine, cellulose, magnesium carbonate, and the like. See Martin, E. W. Remington's Pharmaceutical Sciences.

As described herein, the compositions can take the form of lotions, creams, suspensions, emulsions, tablets, pills, capsules, powders, sustained-release formulations and the like. In some embodiments, the compositions or formulations can be administered to a subject in any non-parenteral manner known to one of skill whereas, in contrast, a parenteral administration involves piercing the skin or a mucous membrane. Depending on the target tissue, the administration can be topical, oral, ocular, otologic, nasal, urogenital, rectal, dermal, vaginal or otherwise to a mucous membrane. Oral administration, for example, can include digestive tract, buccal, and sublingual administration, and a solid or liquid carrier can be used. One of skill will appreciate that the therapeutic program selected, the agents administered, the condition of the subject, and the effects desired, can affect the administration schedule and program used.

The compositions or formulations can be contained in forms that include tablets, troches, capsules, elixirs, beverages, suspensions, syrups, wafers, chewing gums, gels, hydrogels, and the like. Tablets, pills, capsules, troches liquids and the like may also contain binders, excipients, disintegrating agent, lubricants, glidants, chelating agents, buffers, tonicity modifiers, surfactants, sweetening agents, and flavoring agents. Some examples of binders include microcrystalline cellulose, gum tragacanth or gelatin. Some examples of excipients include starch or maltodextrin. Some examples of disintegrating agents include alginic acid, corn starch and the like. Some examples of lubricants include magnesium stearate or potassium stearate. An example of a chelating agent is EDTA. Some examples of buffers are acetates, citrates or phosphates. Some examples of tonicity modifiers include sodium chloride and dextrose. Some examples of surfactants for micellation or increasing cell permeation include coconut soap, anionic, cationic or ethoxylate detergents. An example of a glidant is colloidal silicon dioxide. Some examples of sweetening agents include sucrose, saccharin and the like. Some examples of flavoring agents include peppermint, chamomile, orange flavoring and the like.

In the digestive tract, for example, a solid can include a pill, capsule, tablet, or time-release technology in some embodiments; and, a liquid can include a solution, soft gel, suspension, emulsion, syrup, elixir, tincture, or a hydrogel. Digestive tract administration can include oral or rectal administration using any method known to one of skill. For buccal, sublingual, and sublabial administration, a solid can include an orally disintegrating tablet, a film, a lollipop, a lozenge, or chewing gum; and, a liquid can include a mouthwash, a toothpaste, an ointment, or an oral spray.

One of skill understands that the amount of the agents administered can vary according to factors such as, for example, the type of disease, age, sex, and weight of the subject, as well as the method of administration. Dosage regimens may also be adjusted to optimize a therapeutic response. In some embodiments, a single bolus may be administered; several divided doses may be administered over time; the dose may be proportionally reduced or increased; or, any combination thereof, as indicated by the exigencies of the therapeutic situation and factors known to one of skill in the art. It is to be noted that dosage values may vary with the severity of the condition to be alleviated, as well as whether the administration is prophylactic, such that the condition has not actually onset or produced symptoms. Dosage regimens may be adjusted over time according to the individual need and the professional judgment of the person administering or supervising the administration of the compositions, and any dosage ranges set forth herein are exemplary only and do not limit the dosage ranges that may be selected.

An "effective amount" of a compound can be used to describe a therapeutically effective amount or a prophylactically effective amount. An effective amount can also be an amount that ameliorates the symptoms of a disease. A "therapeutically effective amount" can refer to an amount that is effective at the dosages and periods of time necessary to achieve a desired therapeutic result and may also refer to an amount of active compound, prodrug or pharmaceutical agent that elicits any biological or medicinal response in a tissue, system, or subject that is sought by a researcher, veterinarian, medical doctor or other clinician that may be part of a treatment plan leading to a desired effect. In some embodiments, the therapeutically effective amount should be administered in an amount sufficient to result in amelioration of one or more symptoms of a disorder, prevention of the advancement of a disorder, or regression of a disorder. In some embodiments, for example, a therapeutically effective amount can refer to the amount of an agent that provides a measurable response of at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of a desired action of the composition.

In cases of the prevention or inhibition of the onset of a disease or disorder, or where an administration is considered prophylactic, a prophylactically effective amount of a composition or formulation taught herein can be used. A "prophylactically effective amount" can refer to an amount that is effective at the dosages and periods of time necessary to achieve a desired prophylactic result, such as prevent the onset of a sunburn, an inflammation, allergy, nausea, diarrhea, infection, and the like. Typically, a prophylactic dose is used in a subject prior to the onset of a disease, or at an early stage of the onset of a disease, to prevent or inhibit onset of the disease or symptoms of the disease. A prophylactically effective amount may be less than, greater than, or equal to a therapeutically effective amount.

In some embodiments, a therapeutically or prophylactically effective amount of a composition may range in concentration from about 0.01 nM to about 0.10 M; from about 0.01 nM to about 0.5 M; from about 0.1 nM to about 150 nM; from about 0.1 nM to about 500 µM; from about 0.1 nM to about 1000 nM, 0.001 µM to about 0.10 M; from about 0.001 µM to about 0.5 M; from about 0.01 µM to about 150 µM; from about 0.01 µM to about 500 µM; from about 0.01 µM to about 1000 nM, or any range therein. In some embodiments, the compositions may be administered in an amount ranging from about 0.005 mg/kg to about 100 mg/kg; from about 0.005 mg/kg to about 400 mg/kg; from about 0.01 mg/kg to about 300 mg/kg; from about 0.01 mg/kg to about 250 mg/kg; from about 0.1 mg/kg to about 200 mg/kg; from about 0.2 mg/kg to about 150 mg/kg; from about 0.4 mg/kg to about 120 mg/kg; from about 0.15 mg/kg to about 100 mg/kg, from about 0.15 mg/kg to about 50 mg/kg, from about 0.5 mg/kg to about 10 mg/kg, or any range therein, wherein a human subject is often assumed to average about 70 kg.

In some embodiments, the compositions or formulations can be administered in conjunction with at least one other therapeutic agent for the condition being treated. The amounts of the agents can be reduced, even substantially, such that the amount of the agent or agents desired is reduced to the extent that a significant response is observed from the subject. A "significant response" can include, but is not limited to, a reduction or elimination of a symptom, a visible increase in a desirable therapeutic effect, a faster response to the treatment, a more selective response to the treatment, or a combination thereof. In some embodiments, the other therapeutic agent can be administered, for example, in an amount ranging from about 0.1 µg/kg to about 1 mg/kg, from about 0.5 µg/kg to about 500 µg/kg, from about 1 µg/kg to about 250 µg/kg, from about 1 µg/kg to about 100 µg/kg from about 1 µg/kg to about 50 µg/kg, or any range therein. Combination therapies can be administered, for example, for 30 minutes, 1 hour, 2 hours, 4 hours, 8 hours, 12 hours, 18 hours, 1 day, 2 days, 3 days, 4 days, 5 days, 6 days, 7 days, 8 days, 9 days, 10 days, 2 weeks, 3 weeks, 4 weeks, 6 weeks, 3 months, 6 months, 1 year, 2 years. any combination thereof, or any amount of time considered desirable by one of skill. The agents can be administered concomitantly, sequentially, or cyclically to a subject. Cycling therapy involves the administering a first agent for a predetermined period of time, administering a second agent or therapy for a second predetermined period of time, and repeating this cycling for any desired purpose such as, for example, to enhance the efficacy of the treatment. The agents can also be administered concurrently. The term "concurrently" is not limited to the administration of agents at exactly the same time, but rather means that the agents can be administered in a sequence and time interval such that the agents can work together to provide additional benefit. Each agent can be administered separately or together in any appropriate form using any appropriate means of administering the agent or agents. One of skill can readily select the frequency, duration, and perhaps cycling of each concurrent administration.

Each of the agents described herein can be administered to a subject in combination therapy. In some embodiments, the agents can be administered at points in time that vary by about 15 minutes, 30 minutes, 1 hour, 2 hours, 4 hours, 8 hours, 12 hours, 18 hours, 24 hours, 48 hours or 1 week in time. In some embodiments, at least one of the agents is an immunomodulatory agent. In other embodiments, the agents can include antiproliferatives, antineoplastics, antimitotics, anti-inflammatories, antiplatelets, anticoagulants, antifibrins, antithrombins, antibiotics, antiallergics, antioxidants, and any prodrugs, codrugs, metabolites, analogs, homologues, congeners, derivatives, salts and combinations thereof.

Without intending to be limited to any theory or mechanism of action, the following examples are provided to further illustrate the teachings presented herein. It should be appreciated that there are several variations contemplated within the skill in the art, and that the examples are not intended to be construed as providing limitations to the claims.

Example 1

A Method of Removing a Whole Saliva from a Leech

This example shows that leeches can be fed a phagostimulatory agent, induced to regurgitate the agent to collect the whole saliva as an unrefined, whole saliva in the regurgitation, and then be revitalized for reprocessing to collect more saliva. The regurgitation can be induced, for example, by significantly lowering the leeches body temperature to a state of paralysis or near-paralysis to induce a vomiting. The leeches can then be warmed to re-animate, or revitalize, the leeches for storage and/or the reprocessing to collect more saliva.

The leeches were collected by a local supplier from the natural lake, Cheneh, located in Terengganu, Malaysia. The leeches were maintained at room temperature under 12 h:12 h light and dark cycle in well-aerated plastic containers filled with un-chlorinated tap water which was regularly changed every 2-3 days.

FIG. 1 illustrates a method of feeding a phagostimulatory agent to a leech using a membrane, according to some embodiments. As shown in FIG. 1, the leeches 105 were fed a solution of the phagostimulatory agent 110 comprising 0.001M arginine in normal saline. The leeches 105 were fed using the feeding device having the parafilm membrane 120 stretched across the glass funnel 100 filled with the phagostimulatory solution 110 warmed at a temperature of 37° C. The starved leeches 105 attach to the membrane 120, feed by sucking the phagostimulatory solution 110 through the membrane 120 until satiated, and drop spontaneously.

Figure 2A:
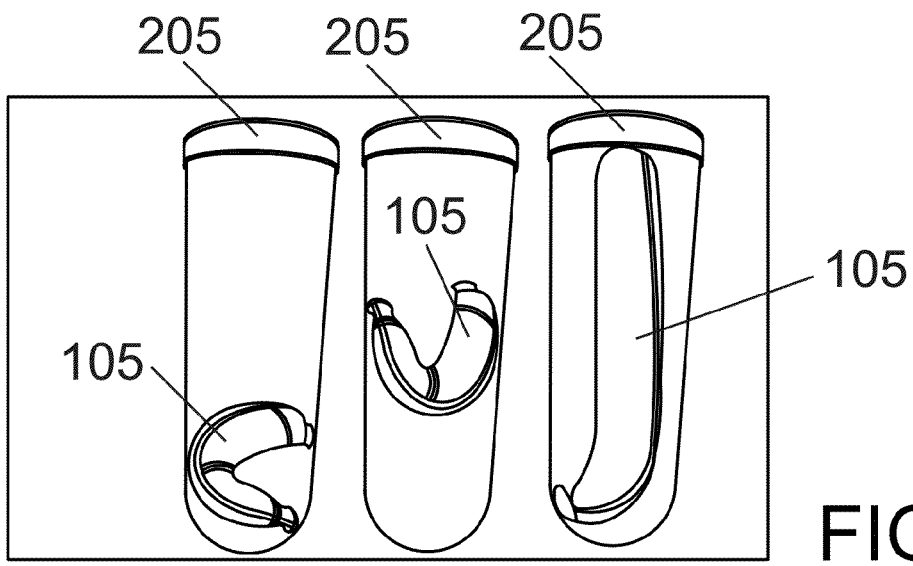
FIGS. 2A-2C illustrate the collection of unrefined, whole saliva extract, according to some embodiments.
Figure 2B:
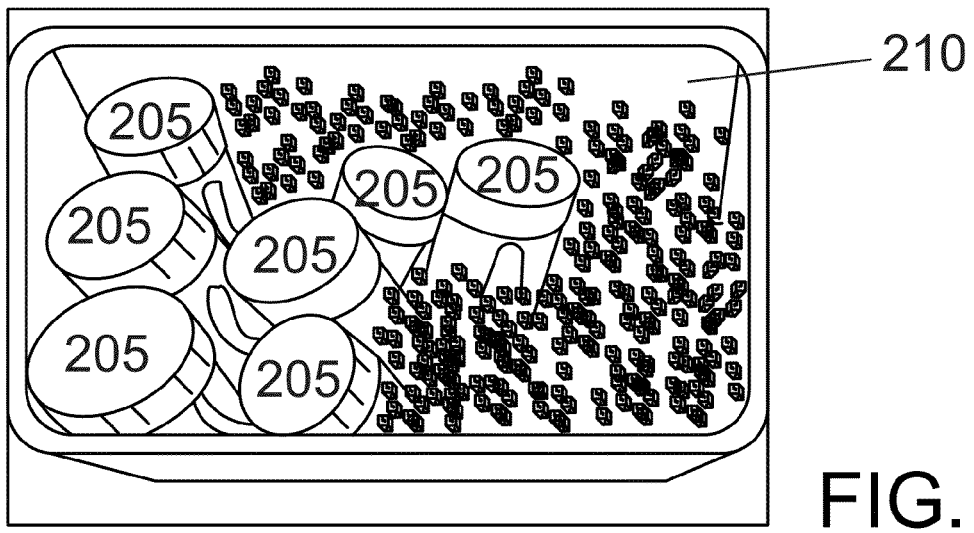
Figure 2C:
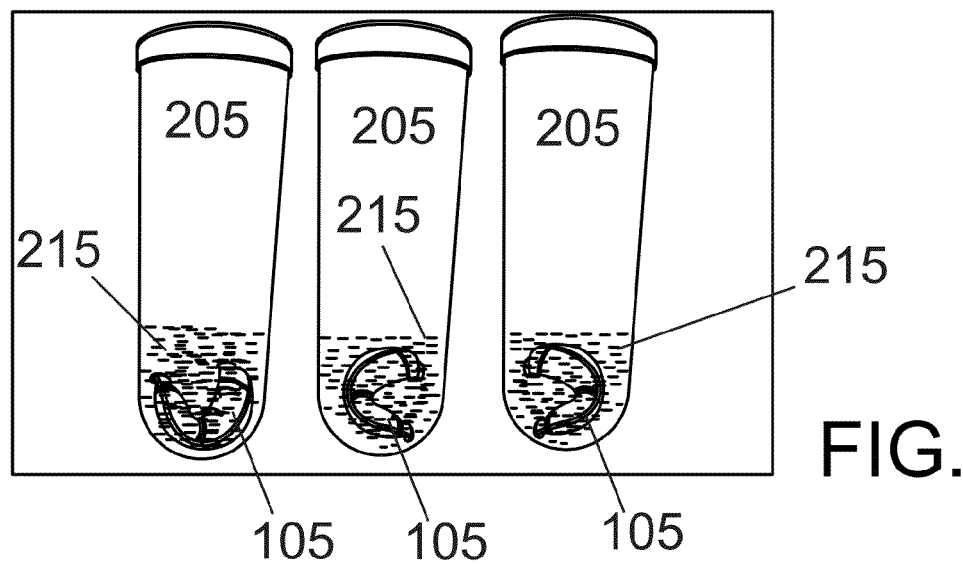

FIGS. 2A-2C illustrate the collection of unrefined, whole saliva extract, according to some embodiments. The engorged leeches 105 that were fed the phagostimulatory solution 110 were transferred to polypropylene containers 205 as shown in FIG. 2A, immersed in an ice bath 210 for about 15 to about 20 minutes as shown in FIG. 2B, and induced to vomit an unrefined, whole saliva 215 as shown in FIG. 2C.

The low temperature induced a regurgitation of the phagostimulatory solution 110, as well as a sort of paralysis or near-paralysis of the leech 105. The paralyzed leeches 105 were squeezed to remove additional unrefined whole saliva 215 without harming the leeches 105. A valuable process consideration is that the leeches 105 were found to readily regain their activity by immersing them in a warm water bath at 37° C. for about 15 to about 30 min, after which they are revitalized and can be stored for re-use.

The unrefined whole saliva was a colorless fluid that was pooled and centrifuged at 4° C. and 9000 rpm for 15 min to remove solids and refine the whole saliva. To further refine the whole saliva, the supernatant was filtered using a 0.45 μm filter paper. The refined leech saliva extract was aliquoted in amber flat-bottom glass tubes in amounts that did not exceed 2 ml for a 24-hour lyophilization cycle. Before lyophilization, the refined extracts were frozen at −80° C. for 30 min. After lyophilizations, the refined extracts were kept at −80° C. in the closed, amber flat-bottom glass tubes.

Example 2

Chemical Characterization of the Leech Saliva Extract

This example provides a chemical characterization of the refined, leech saliva extract (LSE).

Standard procedures known to those of skill were used to produce UV spectra of the LSE. The spectra were obtained by scanning and measuring the $\lambda_{max}$, showing an optimum protein spectrum with $2\lambda_{max}$ values at 199 nm and 207 nm.

Figure 3:
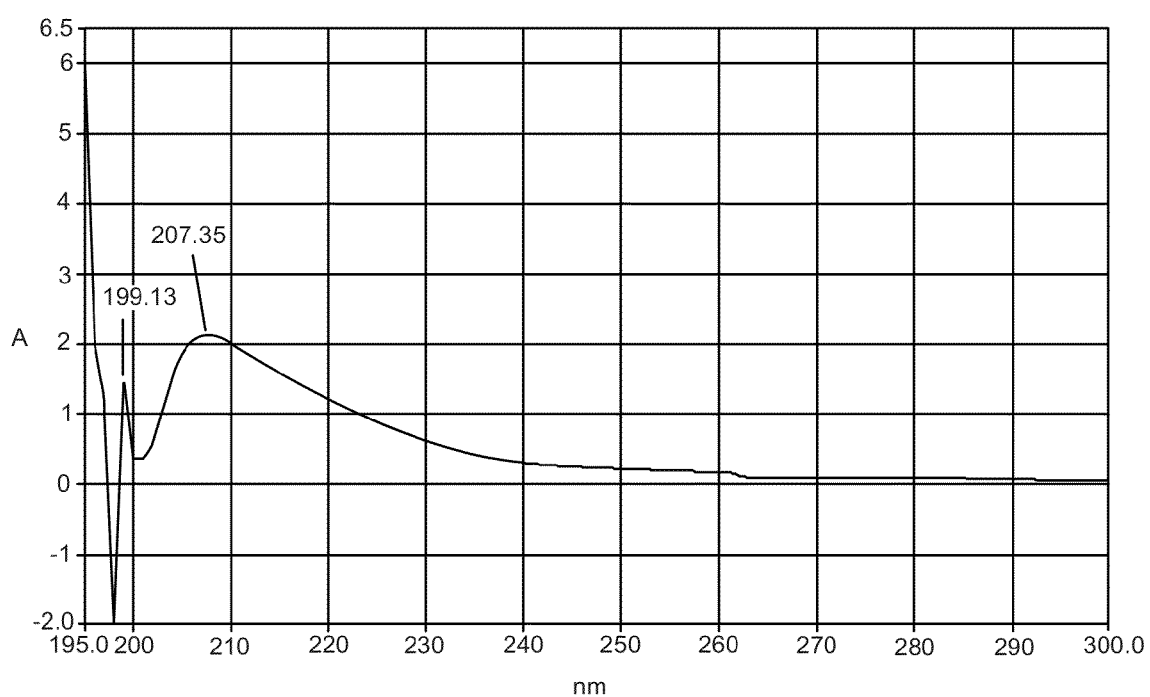
FIG. 3 illustrates a UV spectra of the refined, leech saliva extract, according to some embodiments.

FIG. 3 illustrates a UV spectra of the refined, leech saliva extract, according to some embodiments. The spectra of leeches' saliva extract were determined using UV spectrophotometer in the following steps: a) UV lamp was warmed up for about 15 min, b) the instrument was adjusted to spectrum mode, c) wavelengths were adjusted to a $\lambda_{min}$=190 nm, and a $\lambda_{max}$=800 nm, d) a blank (the phagostimulatory solution) was used to calibrate to zero.

Standard procedures known to those of skill were used to produce a quantitative colorimetic protein assay, in which a reagent kit having bovine serum albumin (BSA) as a standard protein was used. Bradford, M. M. Anal. Biochem. 72: 248-254 (1976). A phagostimulatory solution having 0.001M arginine in 0.15M NaCl was used as a blank, and a series of known-concentrations of BSA (10 μg/ml to 250 μg/ml) were prepared in the phagostimulatory solution. Three dilutions of the LSE were prepared in the phagostimulatory solution, and 100-μl volumes of the BSA, LSE and blank were aliquoted in EPPENDROF tubes with an equal volume of Bradford reagent and mixed well. The absorbance at 595 nm ($A_{595}$) were measured using a microplate reader. The $A_{595}$ values of the blank were subtracted from those of BSA and LSE, and a standard curve of the known concentrations of BSA against their $A_{595}$ values was prepared to determine total protein concentration of the leech saliva extract from the plot.

Figure 4:
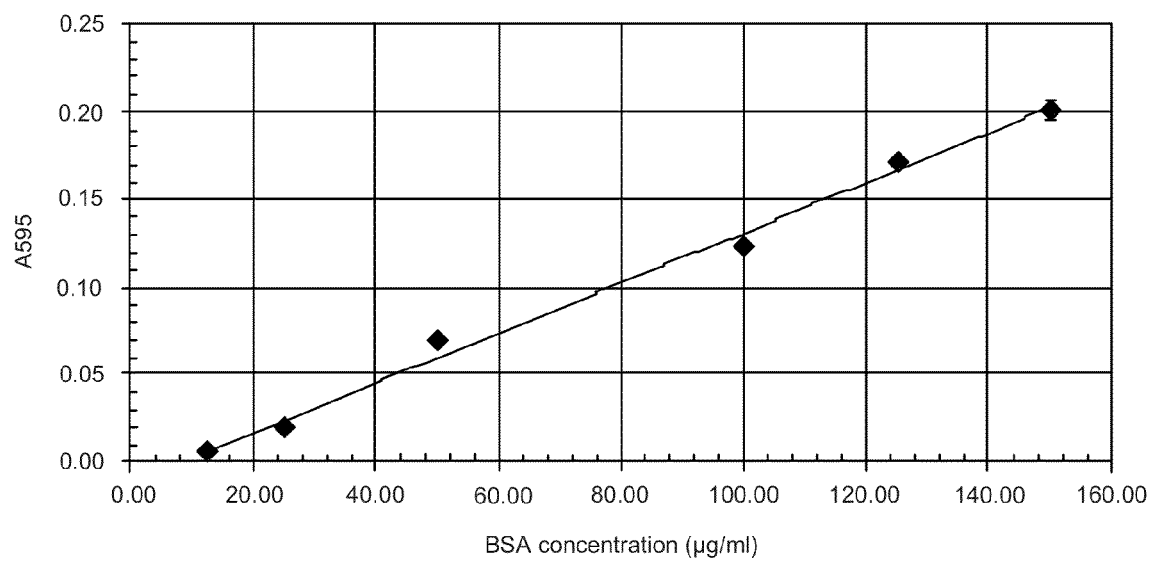
FIG. 4 illustrates a standard curve for a colorimetric Bradford protein assay, according to some embodiments.

FIG. 4 illustrates a standard curve for a colorimetric Bradford protein assay, according to some embodiments. The standard curve was Y=0.001X−0.011, where: X=BSA concentration (μg/ml) and Y=absorbance at 595 nm, $R^2$=0.993. It was found that the total protein concentration of the colorless LSE collected from leeches starved for 16 weeks was 119.691±8.690 μg/ml, whereas leeches starved for 22-weeks yielded LSE with a total protein concentration of 62.682±2.459 μg/ml. Table 2 describes the total protein concentration results of LSE collected from leeches starved for 16 and 22 weeks as the mean of triplicates, expressed as the mean±standard deviation SD (n=3).

TABLE 2

| | | Absorbance $A_{595}$ | | | |
|---|---|---|---|---|---|
| | | Replicate 1 | Replicate 2 | Replicate 3 | $A_{595}$ |
| BSA conc. (μg/ml) | | | | | |
| 12.5 | | 0.007 | 0.006 | 0.000 | 0.004 ± 0.004 |
| 25 | | 0.017 | 0.024 | 0.021 | 0.021 ± 0.003 |
| 50 | | 0.074 | 0.067 | 0.069 | 0.070 ± 0.003 |
| 100 | | 0.120 | 0.123 | 0.127 | 0.124 ± 0.003 |
| 125 | | 0.170 | 0.172 | 0.173 | 0.171 ± 0.002 |
| 150 | | 0.194 | 0.205 | 0.204 | 0.201 ± 0.006 |
| Blank Arg/NaCl (μl) | | | | | |
| 100 | | 0.287 | 0.285 | 0.277 | 0.283 ± 0.005 |
| LSE volume (μl) | | | | | |
| Starvation period 16 weeks | 80 | 0.080 | 0.087 | 0.099 | 0.088 ± 0.010 |
| | 90 | 0.095 | 0.112 | 0.098 | 0.102 ± 0.009 |
| | 100 | 0.098 | 0.099 | 0.099 | 0.099 ± 0.000 |
| Starvation period 22 weeks | 80 | 0.037 | 0.045 | 0.040 | 0.041 ± 0.004 |
| | 90 | 0.044 | 0.042 | 0.043 | 0.043 ± 0.001 |
| | 100 | 0.053 | 0.056 | 0.048 | 0.052 ± 0.004 |
| Total protein concentration in LSE (μg/ml) | | | | | |
| Starvation period 16 weeks (November) | | 124.333 | 125.074 | 109.667 | 119.691 ± 8.690 |
| Starvation period 22 weeks (December) | | 64.750 | 59.963 | 63.333 | 62.682 ± 2.459 |

Standard gel electrophoresis procedures known to those of skill were used to produce molecular weight distributions of the LSE. The separation of molecules within a gel is determined by the relative size of the pores formed within the gel. The pore size of a gel is determined by two factors, the total amount of acrylamide present (designated as % T) and the amount of cross-linker (% C). As the total amount of acrylamide increases, the pore size decreases.

Laemmli SDS-PAGE Gel Electrophoresis of LSE

The Laemmli SDS-PAGE gel electrophoresis method is commonly used and known to one of skill in the art. The method is widely-used to separate proteins based on electrophoretic mobility.

STOCK SOLUTIONS AND BUFFERS: Stock solutions and buffers were prepared for a Laemmli SDS-PAGE (sodium dodecyl sulfate polyacrylamide gel) gel electrophoresis as follows:

In preparing stock solutions, an acrylamide/bisacrylamide (30% T, 2.67% C) (AB 30) was prepared, calculating % C and % T according to (Hjerten, 1962):

$$\% T = \frac{\text{g acrylamide} + \text{g bisacrylamide}}{100 \text{ ml solution}};$$

and, $$\% C = \left(\frac{\text{g acrylamide}}{\text{g acrylamide} + \text{g bisacrylamide}}\right) \times 100;$$

such that 29.2 g acrylamide 29.2 g and 0.8 g bisacrylamide were dissolved in distilled water and the volume was brought to 100 ml in a volumetric flask. The solution was filtered by using WHATMAN filter paper grade 1 under vacuum. The solution was kept in a dark container at 4° C. A 10% (w/v) SDS was prepared by dissolving 10 g of SDS in 90 ml water with gentle stirring and the volume was brought to 100 ml with distilled water in a volumetric flask. The solution was kept in room temperature.

In preparing the 10% APS (ammonium persulfate; prepared and used fresh daily) stock solution as a polymerization initiator, 100 mg of APS was dissolved in 1 ml of distilled water and used immediately.

In preparing a 1.5M tris-HCl, pH 8.8 buffer, 18.15 g of Tris base (tris(hydroxymethyl)aminomethane) was dissolved in 80 ml distilled water, and the pH was adjusted to 8.8 with 6N HCl. The total volume was brought to 100 ml with distilled water and stored at 4° C.

In preparing a 0.5 M tris-HCl buffer, pH 6.8, 6 g of the Tris base was dissolved in 60 ml distilled water. The pH was adjusted to 6.8 with 6 N HCl. The total volume was brought to 100 ml with distilled water and store at 4° C.

In preparing an SDS reducing buffer (sample buffer), 1.25 ml of 0.5M tris-HCl was mixed with 2.5 ml glycerol, 2 ml of the 10% SDS, and 0.2 ml of 0.5% (w/v) bromophenol blue. The total volume was brought to 10 ml with distilled water in a volumetric flask. The buffer was stored at room temperature. 50 µl β-mercaptoethanol were added to 950 µl sample buffer at the time of use.

In preparing a 10× electrode (running) buffer, pH 8.3, 30.3 g of the Tris base, 144.0 g glycine, and 10.0 g SDS were dissolved in distilled water under gentle stirring and the last volume was brought to 1 liter with distilled water. The buffer was kept at room temperature. When running the gel, 100 ml of this buffer were taken and the volume was brought to 1 liter.

MAKING THE GEL: The gel electrophoresis procedure was run using a mini protein tetra cell BIO RAD instrument. The gel (6×8 cm×1 mm) was prepared using glass plates, a gel caster, a resolving gel, and a stacking gel as follows:

In preparing a resolving gel 15%, 5 ml of the acrylamide/bisacrylamide stock solution, 2.4 ml distilled water, 2.5 ml of the pH 8.8 tris buffer and 0.1 ml of the SDS stock solution were mixed and degassed for about 15 min, and 50 µl of the APS stock solution and 5 µl of TEMED (N,N,N',N'-tetramethylethylenediamine) were added.

In preparing the stacking gel, 1.7 ml of the acrylamide/bisacrylamide stock solution, 5.7 ml distilled water, 2.5 ml of the pH 6.8 tris buffer, and 0.1 ml SDS were mixed and degassed for about 15 min. 50 µl of the APS stock solution and 10 µl of TEMED were added.

The resolving gel was poured into the gel slabs using a plastic syringe and 1.5 cm over the separating gel was left empty for the stacking gel. 100 µl isopropanol were laid on the surface of the gel for smoothness and to avoid dehydration, and the gel was allowed to polymerize for about 45 minutes. The isopropanol was removed after polymerization of the resolving gel, and stacking gel was added after washing the surface of the resolving gel with a separating gel buffer. A comb was added to form cells, and the stacking gel was allowed to polymerize for about 30 minutes, and the comb was removed from the gel. The cells were washed with the electrophoresis buffer, and the gel slab was placed in the electrophoresis tank, and the tank was filled with the electrophoresis buffer.

PREPARING THE LSE: the LSE was lyophilized as described herein, and the LSE powder was dissolved in a sample buffer and heated at 95° C. for 5 min in a water bath. SDS was added to the sample buffer to help in the denaturation of proteins, masking the surface of proteins with negative charges to balance the charge/size ratio for all proteins, such that the separation will be based only on the size of the protein. Heating the protein samples before loading helps in completely denaturing all proteins, increases solubility and reduction of disulfide reduction without degradation of proteins (Voerman, 1998).

RUNNING THE GEL: the sample was applied to the cells using a micropipette, and a peptide marker was applied to one cell. The electrophoresis lid was placed carefully, the electrodes were attached to a power source, and the electrophoresis was run for 35 minutes at 200V.

Coomassie Brilliant Blue dye was used to visualize proteins and determine molecular weights from the polyacrylamide gels. A 1 L stock dye solution was prepared by dissolving 1 g Coomassie Brilliant Blue R-250 in 450 ml methanol and 100 ml glacial acetic acid. Distilled water was added to increase total volume to 1 L. The stock dye solution was filtered using WHATMAN filter paper grade 1 and kept at room temperature. A 1 L destaining solution was prepared by mixing 100 ml methanol with 100 ml glacial acetic acid and adding distilled water to increase the total volume to 1 L.

After electrophoresis, the gel was transferred to a plastic container containing stock dye solution and left there for 30 minutes. The staining solution was discarded and the gel was incubated in the destaining solution for 30 minutes with agitation. This step was repeated three to four times with fresh destaining solution, and the gel was incubated in destaining solution overnight. The gel was imaged and documented using a BIO RAD gel imager.

Non-Urea SDS-PAGE Gel Electrophoresis of LSE for Peptides

This portion of the gel electrophoresis analysis was performed according to the Okajima method, which is considered to give better results for peptides. (Okajima, et al., 1993). The method generally uses the same stock solutions and buffers as the Laemmli SDS-PAGE method, an exception being the separating gel buffer.

SEPARATING/STACKING GEL BUFFER: a 3M tris-HCl, pH 8.45 buffer was made by dissolving 36.3 g of the Tris base in distilled water, pH was adjusted to 8.45 with 6N HCl, and the total volume was brought to 100 ml with distilled water.

MAKING THE GEL: In preparing the resolving (separating) gel 19.2%, 10 ml of the AB 30 stock solution was mixed with 3.75 ml of the separating buffer, 0.15 ml SDS, and 1 ml water. The mixture was degassed for 15 min using the sonicator, and 50 µl of the APS stock solution and 10 µl of the TEMED stock solution were added. The mixture was poured into the gel slabs using a plastic syringe and allowed to polymerize for 45 minutes. In preparing the stacking gel 4%, 1.3 ml of the AB 30 stock solution was mixed with 2.5 ml stacking gel buffer, 0.1 ml SDS, and 6 ml water. The mixture was degassed for 15 minutes before adding APS 50 µl and TEMED 10 µl. The sample buffer used for the Laemmli method above was used for this method.

PREPARING THE LSE AND RUNNING THE GEL: the LSE was lyophilized as described herein, and the LSE powder was dissolved in a sample buffer and heated at 95° C. for 5 min in a water bath. SDS was added to the sample buffer to help in the denaturation of proteins, masking the surface of proteins with negative charges to balance the charge/size ratio for all proteins, such that the separation will be based only on the size of the protein. 20 µl of the sample was applied for the gel. The gel was run for 100 minutes at 100V. Commassie blue staining was used to stain the gel.

Tricine SDS-PAGE Gel Electrophoresis of LSE for Peptides in the Range of 1-100 kDa This portion of the gel electrophoresis analysis was performed according to a tricine SDS-PAGE method commonly used to separate proteins in the smaller molecular weight range of 1-100 kDa, and preferably used for resolving proteins smaller than 30 kDa. The use of tricine instead of glycine as a reduction agent provides a better separation of peptides having such low molecular weights.

STOCK SOLUTIONS AND BUFFERS: The AB 30 stock solution, 10% (w/v) SDS, 10% (w/v) APS, and the sample buffer (SDS reducing buffer) is the same as that used in the Laemmli SDS-PAGE method described herein; and, the separating (stacking) gel buffer of Okajima method is used. Otherwise, this method generally uses the same stock solutions and buffers as the Laemmli SDS-PAGE method.

A 10× cathode buffer was prepared by dissolving 12.1 g Tris base, tricine, and 1 g SDS in distilled water. The total volume was brought to 100 ml, and the solution was kept at room temperature. The buffer was diluted 10 times before use. In addition, a 10× anode buffer was prepared by dissolving 12.1 g Tris base in water and adjusting pH to 8.9 with HCl 6 N. The total volume was brought to 100 ml, and the solution was kept at room temperature. The buffer was diluted 10 times before use.

A fixation solution of 5% glutaraldehyde was prepared by add 10 ml of a 50% glutaraldehyde to distilled water and bringing the total volume to 100 ml. The solution was filtered using WHATMAN filter paper grade 1 under a fume hood and used fresh.

MAKING THE GEL: The gels were made according to methods known in the art. (Schägger & von Jagow, 1987). In preparing the resolving (separating) gel 16%, 5 ml of AB 30 was mixed with 5 ml of the separating buffer, 1.5 ml glycerol, and 1.5 ml distilled water. The mixture was degassed for 15 minutes, and 50 µl of the APS stock solution and 5 µl of the TEMED stock solution were added. The gel was poured to the gel slab without delay. The surface of gel was covered by 100 µl isopropanol and allowed to polymerize for 45 minutes. In preparing the stacking gel 4%, 1 ml of the AB 30 was mixed with 3 ml gel buffer, and 11 ml distilled water. The mixture was degassed for 15 minutes, and 100 µl of the APS stock solution and 10 µl of the TEMED stock solution were added. Without delay, the gel was poured to the gel slab. The comb was positioned, and the gel was allowed to polymerize for 30 minutes.

PREPARING THE LSE AND RUNNING THE GEL: the LSE was lyophilized as described herein, and the LSE powder was dissolved in a sample buffer and heated at 95° C. for 5 min in a water bath. SDS was added to the sample buffer to help in the denaturation of proteins, masking the surface of proteins with negative charges to balance the charge/size ratio for all proteins, such that the separation will be based only on the size of the protein. 20 µl of the sample was applied for the gel. The gel was run for 5 hours, running at 40V for the first 3 hours and increasing voltage by 10V every 30 minutes. After electrophoresis, the gel was washed with distilled water for 5 minutes and repeated three times. The washed gel was transferred to a container of the fixer solution for 1 hour and washed with distilled water to remove the glutaraldehyde. The fixed gel was placed in Commassie blue staining solution for 30 min with gentle agitation. The destaining solution was applied for 30 min with agitation, and this step was repeated several times until the band became clear.

The Gel Electrophoresis Results

Figure 5:
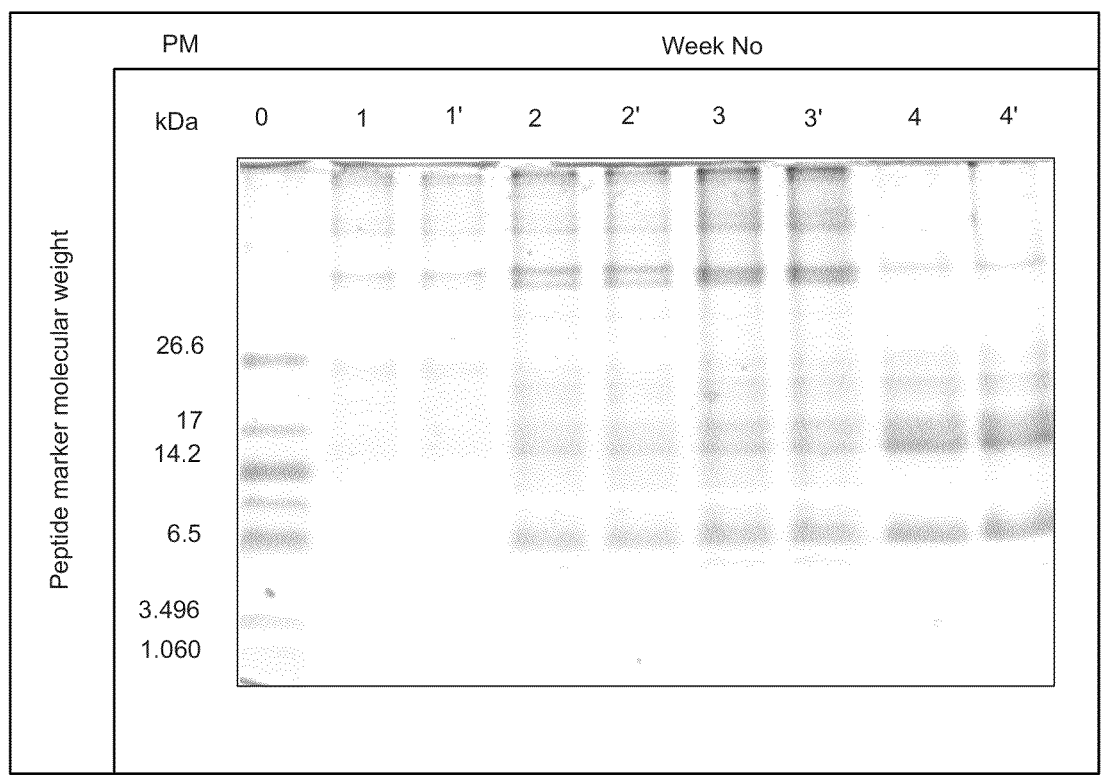
FIG. 5 shows the LSE protein molecular weight distribution results of a Malaysian leech, *Hirudinaria manillensis*, using the Laemmli SDS-PAGE 15% gel electrophoresis, according to some embodiments.

FIG. 5 shows the LSE protein molecular weight distribution results of a Malaysian leech, Hirudinaria manillensis, using the Laemmli SDS-PAGE 15% gel electrophoresis, according to some embodiments. Lane 1 is the peptide marker, and lanes 1-4 represent the week number at which the saliva was extracted in duplicate; wherein, lanes 1-1' are week 2, lanes 2-2' are week 3, lanes 3-3' are week 4, and lanes 4-4' are week 0. As can be seen, the method works well, as the results showed good resolution with highly isolated bands.

Figure 6:
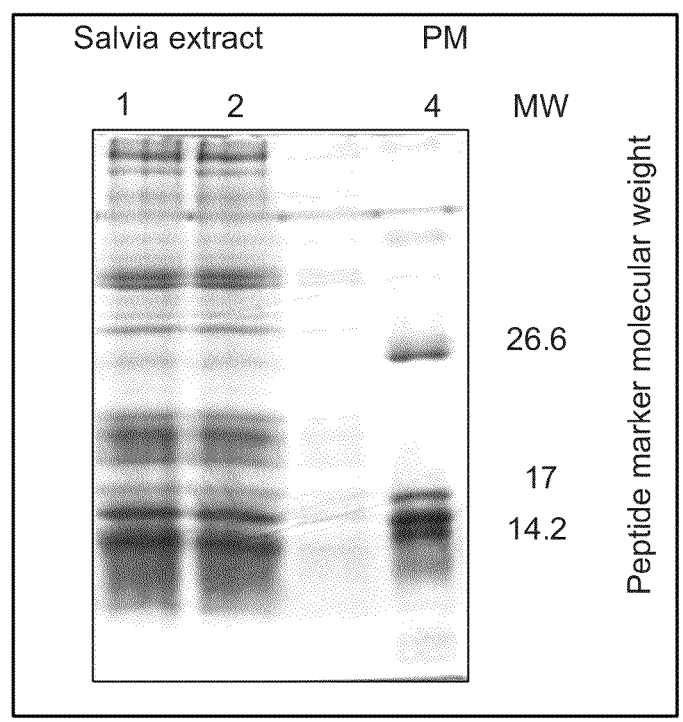
FIG. 6 shows the LSE protein molecular weight distribution results of a Malaysian leech, *Hirudinaria manillensis*, using the Laemmli SDS-PAGE 15% gel electrophoresis, wherein the LSE was concentrated using acetone precipitation, according to some embodiments.

FIG. 6 shows the LSE protein molecular weight distribution results of a Malaysian leech, Hirudinaria manillensis, using the Laemmli SDS-PAGE 15% gel electrophoresis, wherein the LSE was concentrated using acetone precipitation, according to some embodiments. This method showed a high resolution and clear bands, with a protein molecular weight distribution ranging from 10812 Da to 88210 Da. Lanes 1 and 2 are LSE, and lane 4 is the peptide marker.

Figure 7:
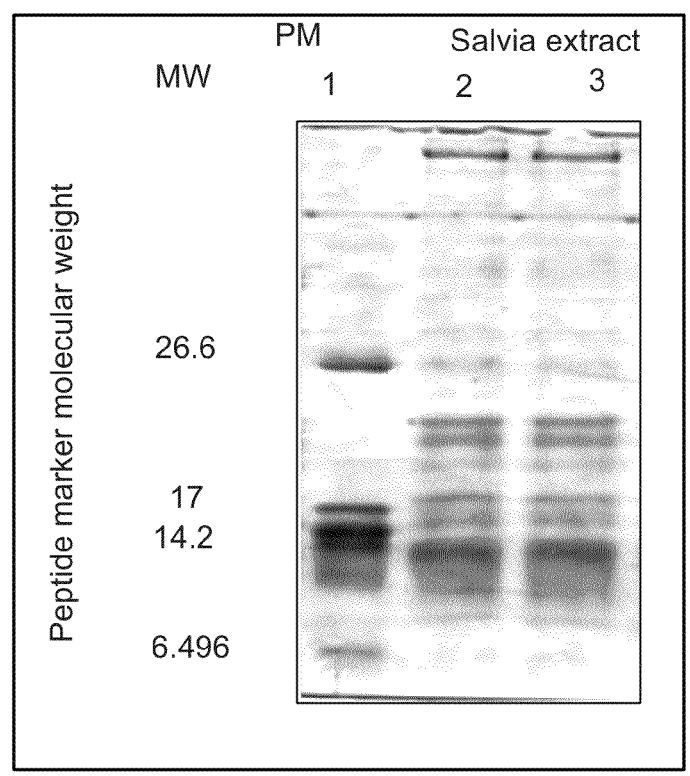
FIG. 7 shows the LSE protein molecular weight distribution results of a Malaysian leech, *Hirudinaria manillensis*, using the Laemmli SDS-PAGE 15% gel electrophoresis, wherein the LSE was precipitated from solution using a trichloroacetic acid (TCA) precipitation, according to some embodiments.

FIG. 7 shows the LSE protein molecular weight distribution results of a Malaysian leech, Hirudinaria manillensis, using the Laemmli SDS-PAGE 15% gel electrophoresis, wherein the LSE was precipitated from solution using a trichloroacetic acid (TCA) precipitation, according to some embodiments. The results show clear bands with a high resolution, although acetone precipitation gave better resolution for the proteins bands. Lanes 2 and 3 are LSE, and lane 1 is the peptide marker.

Figure 8:
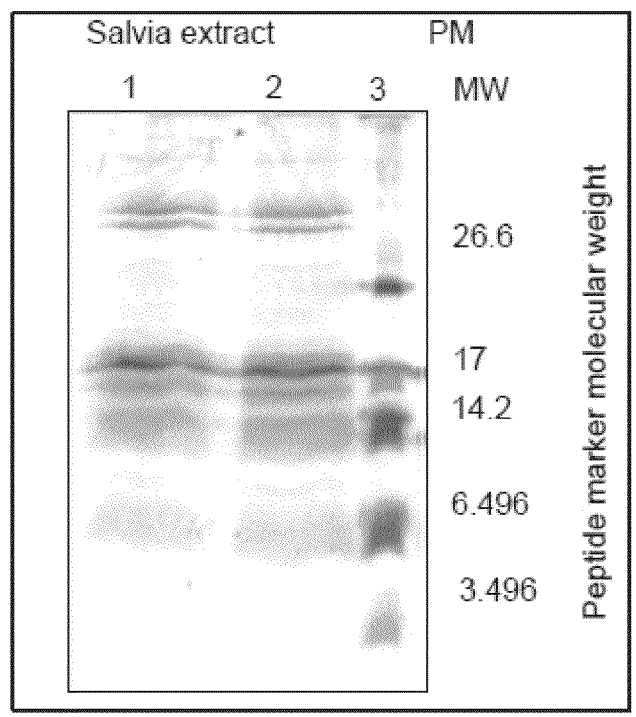
FIG. 8 shows the LSE protein molecular weight distribution results of a Malaysian leech, *Hirudinaria manillensis*, using the Non-Urea SDS-PAGE gel electrophoresis of Okajima, according to some embodiments.

FIG. 8 shows the LSE protein molecular weight distribution results of a Malaysian leech, *Hirudinaria manillensis*, using the Non-Urea SDS-PAGE gel electrophoresis of Okajima, according to some embodiments. Smaller molecular weight peptides and proteins were shown having good resolution with clear bands. The molecular weight range is wider compared to the classic Laemmli SDS-PAGE method, as proteins as small as 6.5 kDa were detected. Lanes 2 and 3 are LSE, and lane 1 is the peptide marker.

Figure 9:
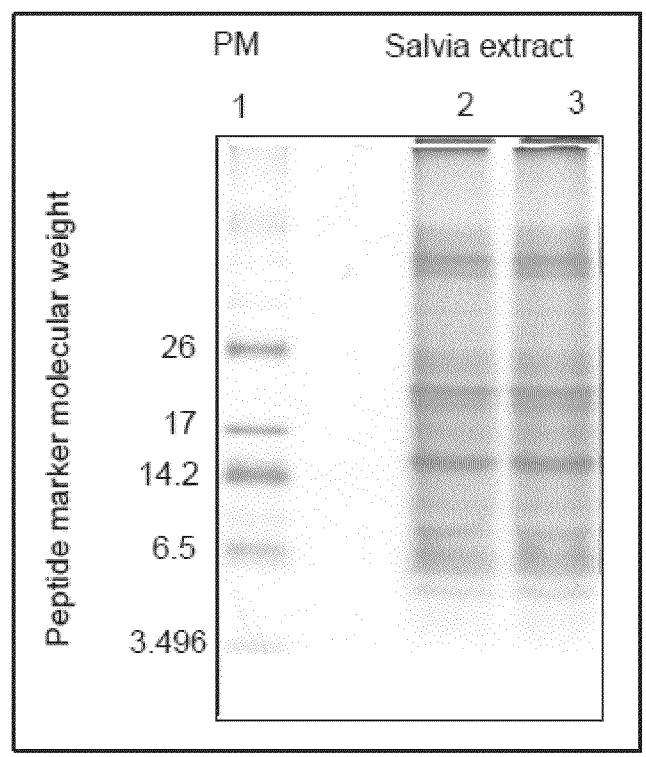
FIG. 9 shows the LSE protein molecular weight distribution results of a Malaysian leech, *Hirudinaria manillensis*, using the Tricine SDS-PAGE gel electrophoresis method, according to some embodiments.

FIG. 9 shows the LSE protein molecular weight distribution results of a Malaysian leech, *Hirudinaria manillensis*, using the Tricine SDS-PAGE gel electrophoresis method, according to some embodiments. The results showed more than 20 proteins and peptides ranging in molecular weight from 4276 Da to 44386 Da. Lanes 2 and 3 are LSE, and lane 1 is the peptide marker.

The data compared well to known literature values of *Hirudinaria* species, such as bufridin (7 kDa), manillase (58 kDa), hirullin P18 (6.8 kDa) and gelin (8.2 kDa). The data suggested other proteins may be shared with other species, such as Calin (65 kDa), Destabilase lysozym (12 kDa), lefaxin (30 kDa), Hirudin (7 kDa) and hyaloronidase (28.5 kDa).

Reverse-Phase HPLC of LSE

This example shows how to use analytical chromatography (Buffer (A), 0.1% TFA in water and Buffer (B), 0.1% TFA in acetonitrile) of the crude saliva extract to identify more than 30 peaks with high resolution in the LSE. In particular, reverse-phase HPLC (RP-HPLC) can be used.

MATERIALS AND METHODS: An Agilent $C_{18}$ RP column, buffer (A) 0.1% TFA in water, buffer (B) 0.1% TFA in acetonitrile, a 1 ml/min flow rate, and a 5% gradient: 5% (B) over 5 min, 5-90% (B) over 40 min wavelength 214 nm, A lyophilized saliva, B fresh saliva. The lyophilized saliva extract after reconstitution in distilled was applied to the $C_{18}$ RP column at a flow rate of 1 ml/min, and a gradient of 5% of (B) over 5 min, followed by 5%-90% (B) over 40 min, and then 90% of (B) over 5 min, and finally 90%-5% of (B) over 5 min. The UV detector was set at 214 nm, and a volume 100 µl was injected in the loop. A blank (0.15M saline+0.001M arginine) was run before each analysis.

Figure 10A:
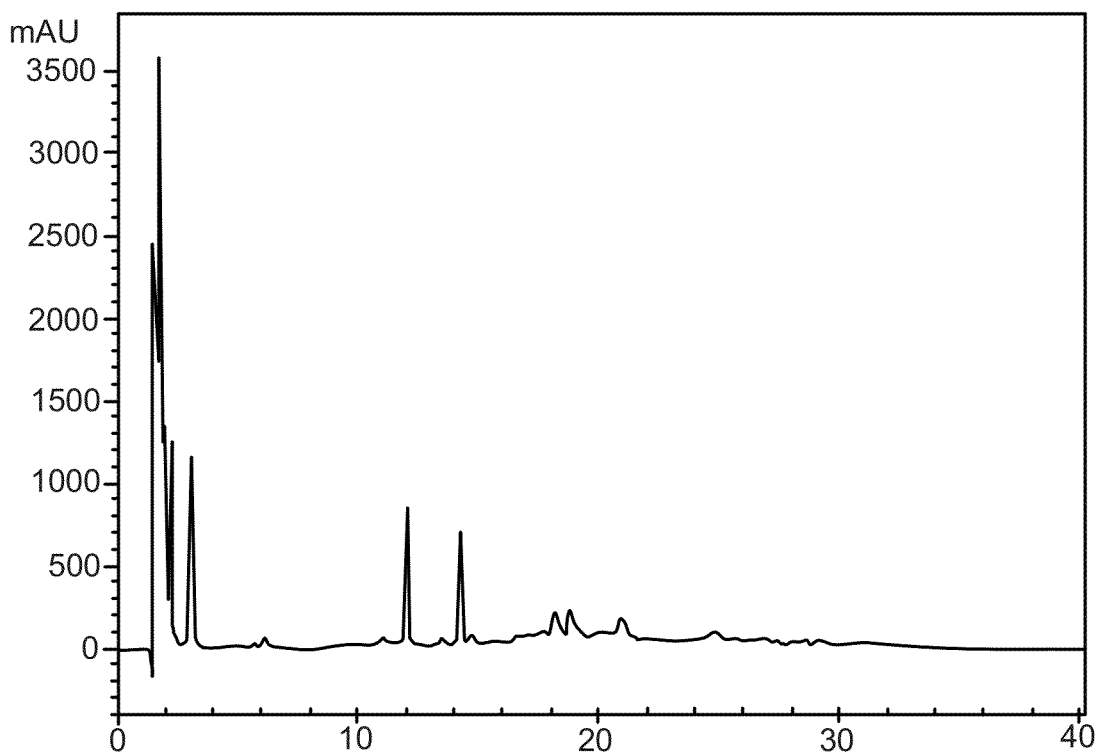
FIGS. 10A and 10B show the results of RP-HPLC in the analysis of LSE, according to some embodiments.
Figure 10B:
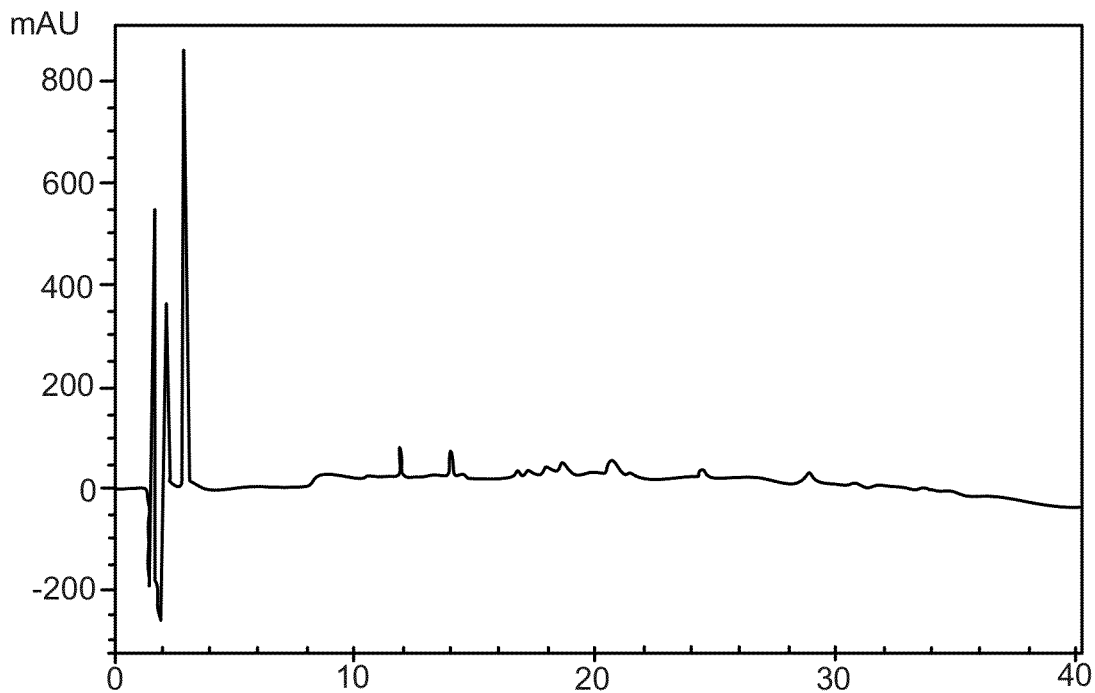

FIGS. 10A and 10B show the results of RP-HPLC in the analysis of LSE, according to some embodiments. As shown, the results were the same, or at least substantially similar, for lyophilized (FIG. 10A) and fresh (FIG. 10B) saliva extracts.

Figure 11:
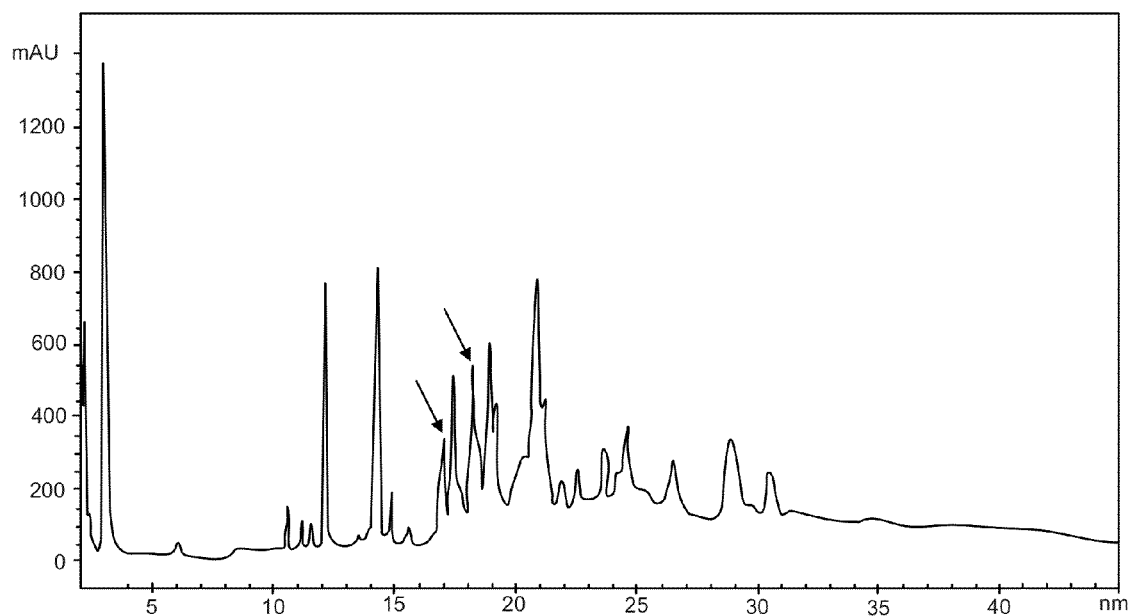
FIG. 11 shows isolation of LSE proteins using RP-HPLC, according to some embodiments.

FIG. 11 shows isolation of LSE proteins using RP-HPLC, according to some embodiments. As can be seen, 30 peaks were isolated from the LSE. Examples of two isolated proteins from the LSE are indicated by arrows.

Figure 12:
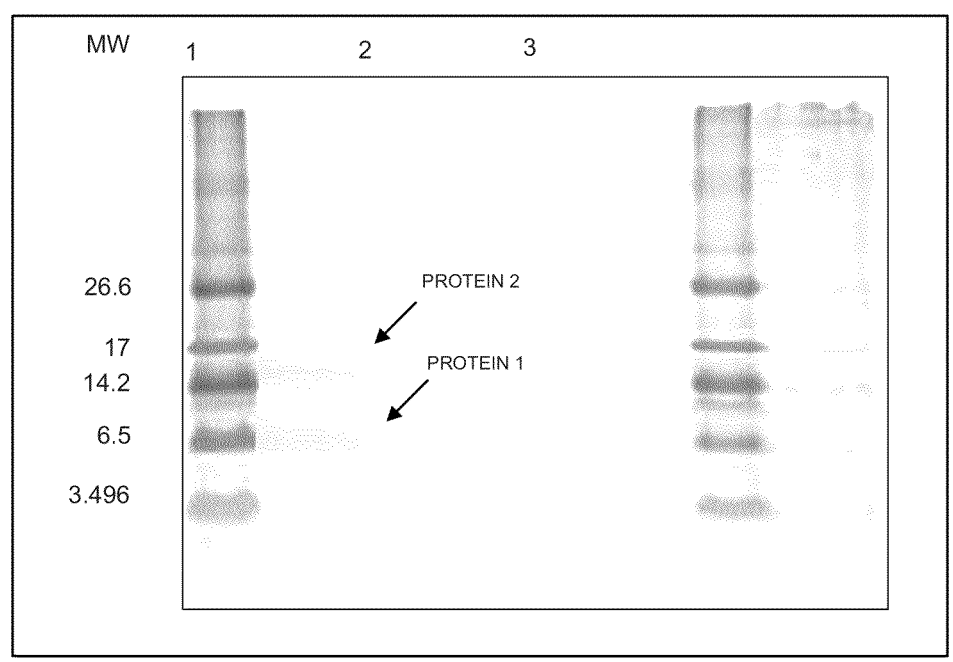
FIG. 12 shows the molecular weights of the two isolated proteins using Tricine SDS-PAGE gel electrophoresis, according to some embodiments.

FIG. 12 shows the molecular weights of the two isolated proteins using Tricine SDS-PAGE gel electrophoresis, according to some embodiments. Lane 1 is the peptide marker, lane 2 is protein 2, and lane 3 is protein 1. The molecular weights of the two isolated proteins, protein 1 and protein 2, were 6289.799 Da and 14244.58 Da, respectively.

Anticoagulant Activity of LSE

This example shows that (i) the lyophilized LSE retains anticoagulant activity, and (ii) active components of the LSE can be identified using known methods. The LSE was frozen at −40° C., lyophilized, dissolved in 60 μl distilled water, and used to assess the anticoagulant activity of isolated portions of the LSE. Isolated proteins were identified and assessed for anticoagulant activity, and the results revealed two active proteins that extend thrombin time. They were given the names. "protein 1" and "protein 2" and prolonged thrombin time by 26.23% and 31.65%, respectively. The isolated proteins were also assessed for inhibition of amidolytic activity of thrombin, and the results show that they inhibited the amidolytic activity of thrombin by 30.61% and 41.22% for protein 1 and protein 2, respectively, confirming the results obtained regarding thrombin time.

The determination of the amidolytic activity of LSE was based on its inhibitory effect on thrombin-induced release of p-nitroanilide from the synthetic substrate of thrombin S-2238 using known methods. (Mao et al., 1987; Schmied, Hoeffken, Hornberger, & Bernard, 1995).

Materials and Methods

1. Preparation of the reaction buffer: All reagents used for this experiment were prepared in phosphate buffered saline-bovine serum albumin buffer (PBS-BSA, pH 7.4) which contains 0.12M NaCl, 0.01M sodium phosphate, 0.01% $NaN_3$ and 0.1% bovine serum albumin.
2. Thrombin reagent and thrombin substrate S-2238: were prepared in PBS-BSA to a final concentration of 0.6NIHU thrombin/ml and 100 μM, respectively. Thrombin substrate solution was preserved at −20° C. to be used within one month according to storage conditions provided by the manufacturer.
3. Amidolytic assay procedures: Volumes of 50 μl of thrombin reagent were mixed with equal volumes of different dilutions of LSE in the 96-well plate. The plate was shaken gently and incubated for 10 min at 25° C. in the microplate reader. Thereafter, 100 μl of the substrate was pipetted and the mixture was agitated. The absorbance at 405 nm ($A_{405}$) was monitored for eight hours at 5-minute intervals. Same procedures were done using the phagostimulatory solution (PhS) as a negative control. Reaction buffer PBS-BSA was considered as a control.
4. Calculations: All measurements were repeated in triplicates and the means were considered. The percentage inhibition (% inhibition) was calculated from the equation:

$$\% \text{ inhibition} = \left( \frac{\text{Absorbance of control} - \text{Absorbance of } LSE}{\text{Absorbance of control}} \right) \times 100$$

Figure 13:
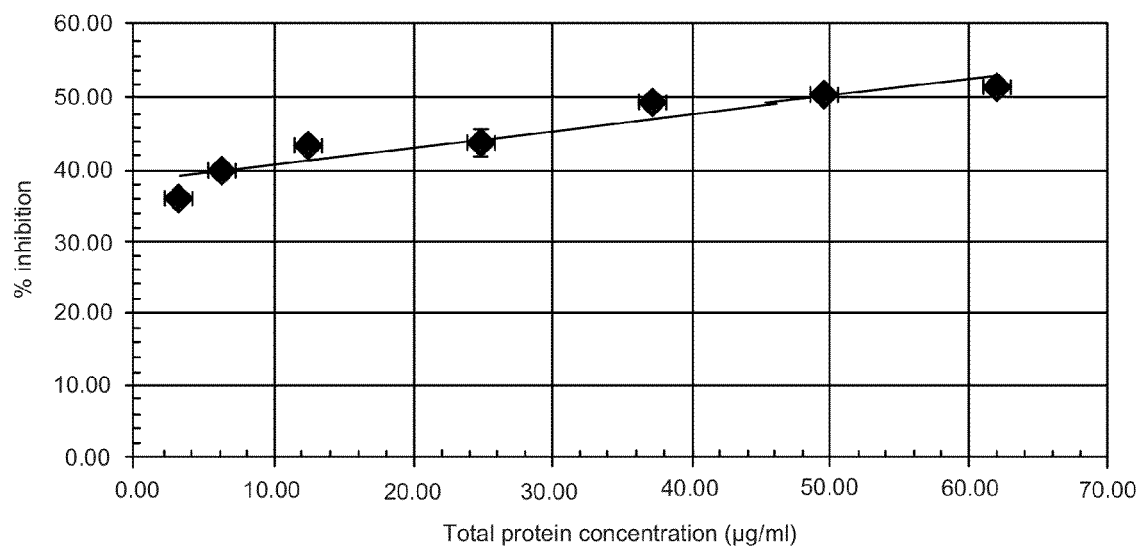
FIG. 13 illustrates IC50 of LSE with respect to antithrombin activity, according to some embodiments.

FIG. 13 illustrates IC50 of LSE with respect to antithrombin activity, according to some embodiments. The LSE effectively inhibited thrombin-mediated release of the p-nitroanilide from the synthetic substrate (S-2238). The protein concentration that inhibits 50% of thrombin activity ($IC_{50}$) was determined by plotting the % inhibition against total protein concentration in the LSE, and it was found to be 49.391±2.219 μg/ml. The dose responsive curve of the amidolytic activity of leech saliva extract. Y=2.28X+38.26, where: Y=% inhibition and X=protein concentration (μg/ml), $R^2$=0.878.

Antithrombin activity was determined using a thrombin time (TT) assay in vitro. The following standard protocols were used as provided with THROMBOCLOTIN reagent and a SYSMIX CA 50 COAGULOMETER:

1. Citrated plasma preparation: prepared from fresh human blood taken by venipuncture immediately prior to the experiment. Fresh human blood (4.5 ml) was mixed with sodium citrate in a citrate tube containing 0.5 ml of 0.11 mol/l sodium citrate (9 parts of blood: 1 part of sodium citrate). The mixture was centrifuged at room temperature (25° C.) for 10 min at 3000 rpm. The supernatant citrated plasma was kept at room temperature (+25 C) to be used within four hours of preparation.
2. Thrombin reagent preparation: Each vial of THROMBOCLOTIN was reconstituted with 10.0 ml distilled water. The resulted solution contains 2.5NIHU thrombin/ml and was stable for one week when stored at 2° C.-8° C.
3. Control plasma preparation: a control plasma test was used before each experiment to evaluate the precision and accuracy of the reagents used and the coagulometer. One vial of CONTROL N (a control plasma used to test the instrument) was dissolved in 1.0 ml distilled water, shaken gently and let to stand for 15 minutes at room temperature. The reconstituted control plasma was kept at −20° C. for a maximum period of four weeks.
4. Thrombin time assay: An aliquot 100 μl of the prepared citrated plasma was pipetted into the pre-warmed coagulation tube provided with the coagulometer and subsequently incubated at 37° C. in the coagulation analyzer well for 3 minutes. 100 μl of the reconstituted thrombin reagent (2.5NIHU thrombin/ml) was added and the time until coagulation started was measured by the coagulometer. Different dilutions of the fresh LSE were mixed with the freshly prepared citrated plasma to yield a final volume of 100 μl and TT values of the mixtures were measured. The phagostimulatory solution was used as a negative control.
5. Calculations: All measurements were repeated in triplicates and the means were considered. The percentage increase of thrombin time (% TT) was calculated from the equation:

$$\% \ TT = \left( \frac{TT \text{ of the sample} - TT \text{ of the citrated plasma}}{TT \text{ of the citrated plasma}} \right) \times 100$$

Fresh LSE collected from leeches starved for 16 weeks prolonged thrombin time (TT) of the citrated plasma in a dose dependent manner. Leech saliva protein concentration which can increase TT two-fold ($IC_{100}$) was estimated by plotting % TT values against saliva protein concentrations that were mixed with the citrated plasma.

Figure 14:
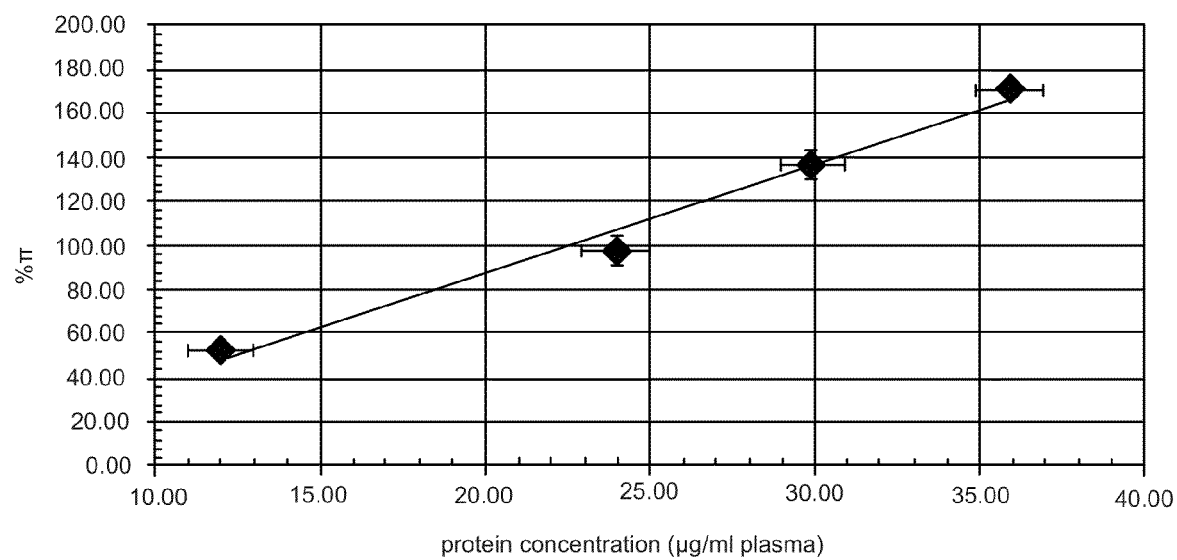
FIG. 14 shows the relationship between thrombin time and the concentration of LSE protein, according to some embodiments.

FIG. 14 shows the relationship between thrombin time and the concentration of LSE protein, according to some embodiments. The concentration of LSE protein which increased TT two-fold ($IC_{100}$) was estimated from the curve of saliva protein concentration (μg/ml plasma) versus percentage increase of TT (% TT). Consequently, it was found that $IC_{100}$ was 22.558 µg/ml plasma. The results show that the antithrombotic activity of LSE was a linear function with the protein concentration in plasma, Y=4.953X−11.73, where: Y=% TT and X=protein concentration (µg/ml), $R^2$=0.984.

Example 3

A Method of Creating a Stable, Lyophilized, Whole-Saliva Extract of a Leech

This example shows the substantial effect of lyophilization conditions and storage conditions on the activity and stability of the LSE. Antithrombin activity was used as a measure of the activity and stability of the LSE under the different conditions. Lyophilization conditions such as vessel type, prefreezing temperature, lyophilization time, and storage conditions were all varied to determine their effects on LSE activity.

The LSE was aliquoted in separate glass and polypropylene tubes each containing 1 ml. The samples were then frozen at −20° C. or −40° C., and the frozen samples were lyophilized for 12, 24, 48 or 72 hours. The antithrombin activity (% TT) of each lyophilized sample was determined and compared with that of the fresh LSE. In addition, glass or polypropylene tubes, each containing 1 ml of lyophilized or non-lyophilized LSE were stored at room temperature, 4° C., and −20° C. Some tubes at room temperature were protected from light by wrapping them with aluminum foil. The antithrombin activity (% TT) of each sample was monitored for a period of six months and compared with that of the fresh LSE.

Figure 15:
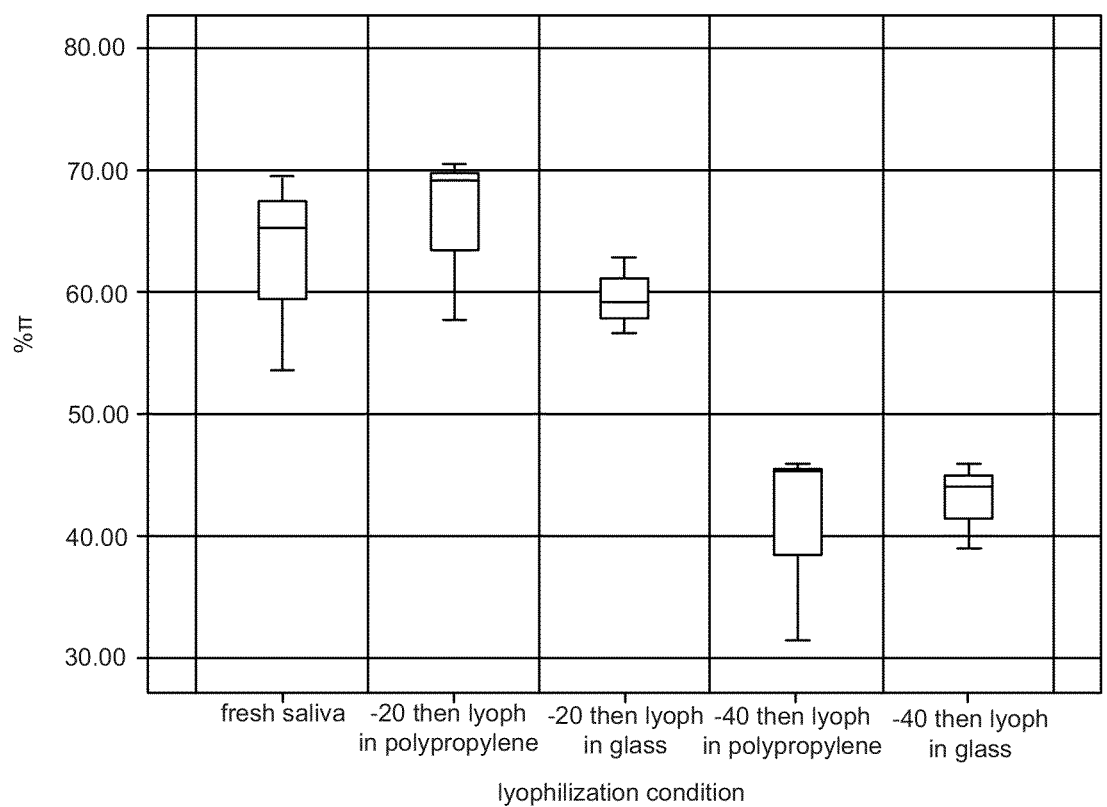
FIG. 15 shows effects of lyophilization conditions and storage conditions on the activity and stability of the LSE, according to some embodiments.

FIG. 15 shows effects of lyophilization conditions and storage conditions on the activity and stability of the LSE, according to some embodiments. The results are the mean of triplicates±the standard error of the mean SEM (n=3), analyzed using one-way ANOVA and Tukey's HSD post hoc test; p<0.05 was considered statistically significant. Freezing at −40° C. before lyophilization significantly (p<0.05) decreased the antithrombotic activity of LSE by 31-34% when compared to the activity of fresh LSE. Freezing at −20° C. before lyophilization provided an antithrombin activity (% TT=60-65%) similar to that of fresh LSE (% TT=62%), regardless the vessel type. The container had no significant effect on LSE activity during lyophilization.

Figure 16:
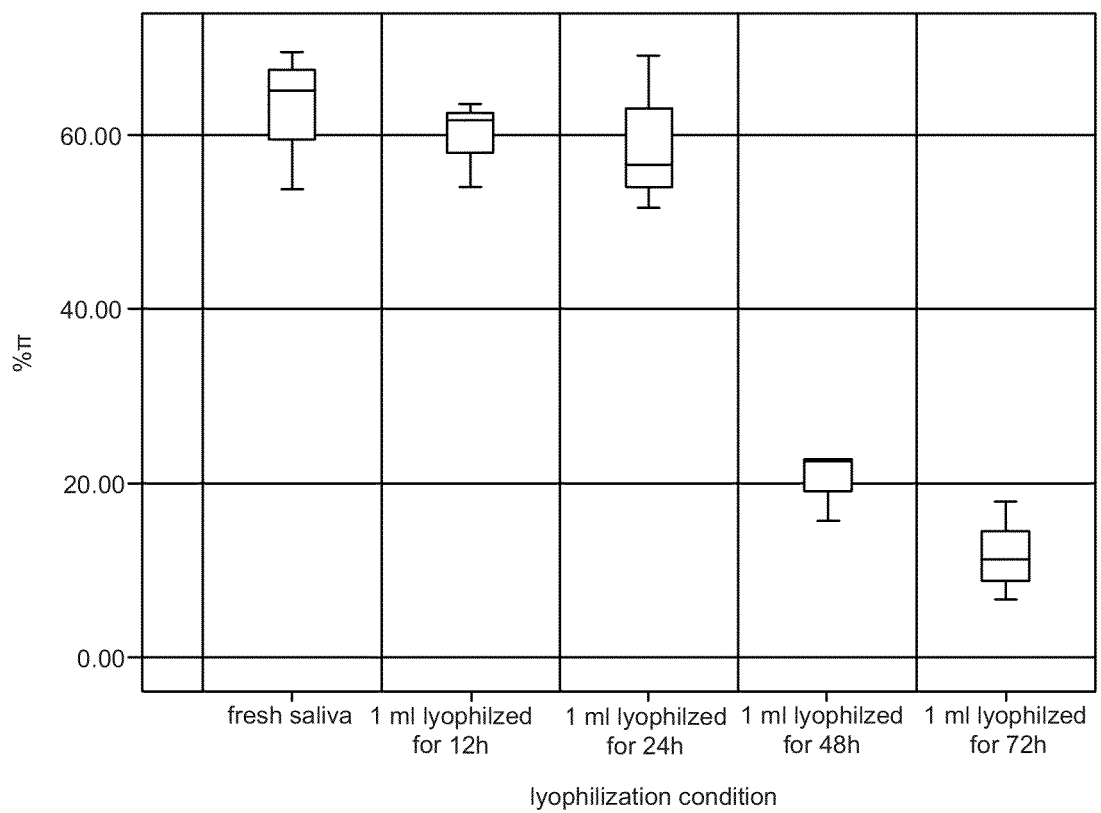
FIG. 16 shows the effect of lyophilization time on antithrombin activity of LSE, according to some embodiments.

FIG. 16 shows the effect of lyophilization time on antithrombin activity of LSE, according to some embodiments. All samples were lyophilized for 24 h in glass tube. $^{\alpha}$p<0.001 when compared with fresh LSE. The results are the mean of triplicates±the standard error of the mean SEM (n=3), analyzed using one-way ANOVA and Tukey's HSD post hoc test; p<0.05 was considered statistically significant. Lyophilization for more than 24 hours led to a dramatic decrease 67-80% (p<0.001) in antithrombin activity. Lyophilization for 12-24 hours, on the other hand, retained about 95% of its original activity.

Storage at Room Temperature

After one day of storage, all samples (lyophilized or non-lyophilized) stored at room temperature over time lost activity compared to the initial activity of fresh LSE.

Fresh samples stored in glass tubes exposed to light lost more than 90% activity after one day. Non-lyophilized LSE kept in glass tubes protected from light lost 62.2% activity after one day of storage, and more than 90% after 3 days of storage. Non-lyophilized samples kept in polypropylene tubes showed more than 90% loss of activity after a storage period of one day, regardless of protection from light. Lyophilized LSE kept in glass tubes protected from light for one, three, and seven days lost about 26.5%, 75% and 95% activity, respectively. Lyophilized LSE exposed to light for one day lost about 48% activity, and about 90% after 3-7 days. Lyophilized LSE kept in polypropylene tubes in the dark for one day lost 57% activity, and more than 90% activity after 3 days. Lyophilized LSE kept in polypropylene tubes and exposed to light lost 80%-99% activity over 7 days.

Light significantly affected LSE activity at room temperature. Lyophilized LSE kept in glass tubes protected from light lost 26.5% activity in one day compared to a 48% (p<0.05) activity loss for samples exposed to light. Non-lyophilized samples kept in polypropylene tubes protected from light lost 62.2% activity after one day, and lost about 92% (p<0.001) of their activity when exposed to light.

The type of the container affected activity of LSE when stored at room temperature. Lyophilized samples stored in glass tubes lost 26.5%-47.8% activity, whereas those stored in polypropylene tubes lost 57.1%-84.5% (p<0.05) activity. Non-lyophilized samples kept in glass tubes protected from light lost 62% activity, whereas such samples stored in polypropylene tubes lost 92% (p<0.001) activity in one day protected from light.

Lyophilization provided stability to the LSE at room temperature. Non-lyophilized samples show a substantial loss of activity when compared to lyophilized samples when stored under the same conditions. Non-lyophilized LSE stored in glass tubes protected from light lost 62.2% activity after one day, whereas the lyophilized LSE lost 26.5% activity after one day (p<0.001). After 3-7 days of storage, significant differences between samples were not observed because samples lost a great part of their biological activity (75-95%).

Figure 17:
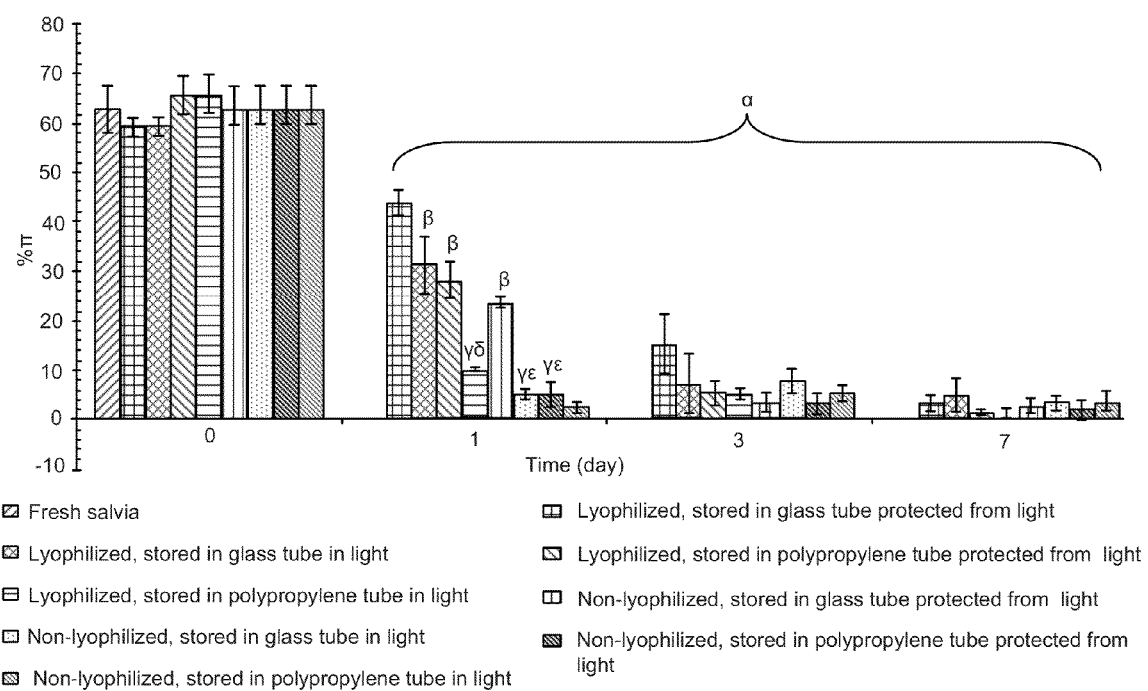
FIG. 17 shows the effect of light, and container on antithrombin activity of LSE samples (lyophilized and non-lyophilized) stored at room temperature for up to 7 days, according to some embodiments.

FIG. 17 shows the effect of light, and container on antithrombin activity of LSE samples (lyophilized and non-lyophilized) stored at room temperature for up to 7 days, according to some embodiments. The results are the mean±standard error of the mean SEM (n=3) and analyzed by General Linear Model (GLM), repeated measure ANOVA, using SPSS 18.0 software, and p<0.05 was considered statistically significant. α is significant when compared with fresh LSE (reference control); β is significant when compared with lyophilized LSE stored in glass tubes and protected from light; γ is significant when compared with lyophilized LSE stored in polypropylene tubes and protected from light; ε is significant when compared with non-lyophilized LSE stored in glass tubes and protected from light; and δ is significant when compared with lyophilized LSE in glass tubes in light.

Storage at 4° C.

At a reduced temperature of 4° C., no significant loss of activity occurred in seven days, regardless of sample type or storage conditions. However, all samples showed a significant decrease (p<0.001) in activity after 15 days when compared to the initial activity of fresh saliva (control reference).

Non-lyophilized samples kept in glass tubes retained 100%-97% activity during the seven days. A sharp decline (45%) in activity occurred after 15 days, and longer storage times showed more than a 90% loss of activity. Lyophilized samples kept in glass tubes retained about 100% activity after seven days, lost about 27% of activity after 15 days, and lost about 80-90% activity after 30 days.

Non-lyophilized samples kept in polypropylene containers retained 100-95% activity during the seven days, lost about 47% activity after 15 days, and more than 90% activity after 30 days. Lyophilized saliva samples kept in polypropylene containers lost about 0-9% activity after 3 days, about 13% after 7 days, about 32% after 15 days, and about 85-95% after 30 days.

Figure 18:
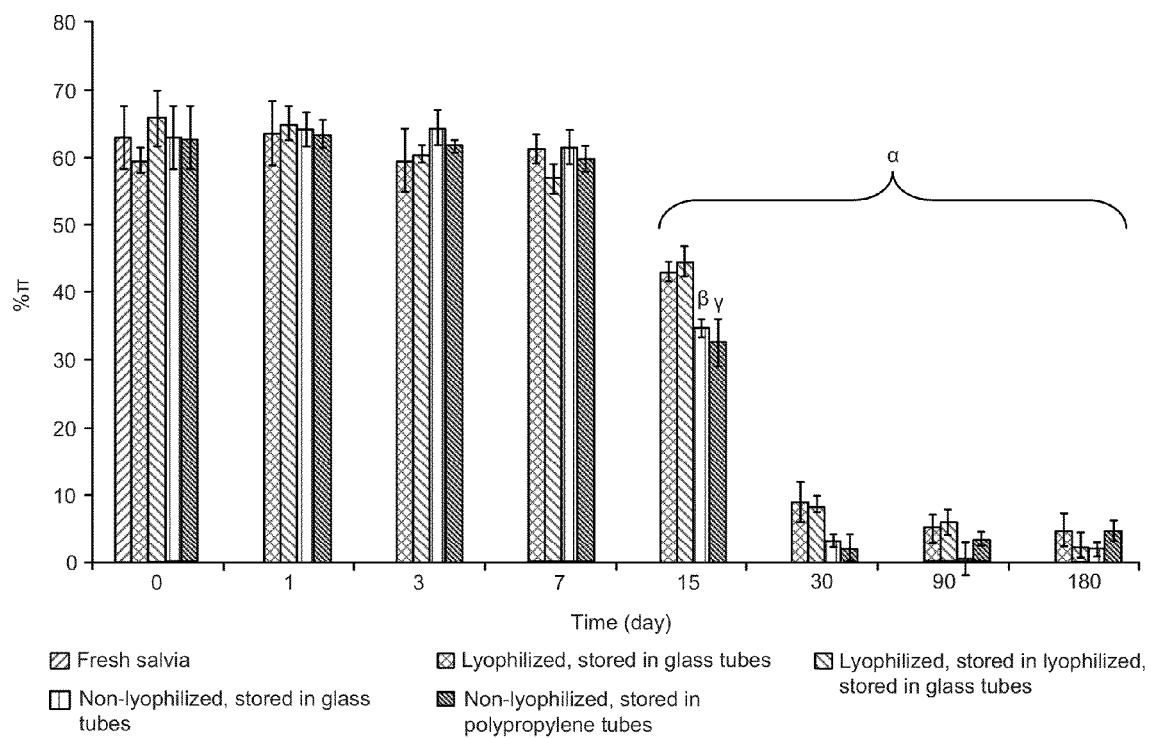
FIG. 18 shows the effect of storage temperature, light, and container on antithrombin activity of LSE samples (lyophilized and non-lyophilized) for up to 180 days at 4° C., according to some embodiments.

FIG. 18 shows the effect of storage temperature, light, and container on antithrombin activity of LSE samples (lyophilized and non-lyophilized) for up to 180 days at 4° C., according to some embodiments. After 30 days-180 days, all samples lost 81-98% of their activity. The results are the mean±standard error of the mean SEM (n=3) and analyzed by General Linear Model (GLM), repeated measure ANOVA, using SPSS 18.0 software, and p<0.05 was considered statistically significant. α is significant when compared with fresh LSE (reference control); β is significant when compared with lyophilized LSE stored in glass tubes; γ is significant when compared with lyophilized LSE stored in polypropylene tubes. The type of container only had a minor effect, whereas lyophilization had a significant effect on activity after 15 days of storage. Non-lyophilized samples showed much more activity loss than lyophilized samples. Non-lyophilized samples kept in glass tubes lost 45% activity, while lyophilized counterparts lost 27% after 15 days of storage (p<0.05-0.001). Non-lyophilized samples kept in polypropylene tubes lost 47% compared to a loss of 32% in lyophilized samples (p<0.05) for the same period of 15 days.

Storage at −20° C.

At the storage temperature of −20° C., the type of container and state of the extract were not statistically significant. Non-lyophilized LSE stored in glass tubes lost from 0-6% activity (statistically insignificant) in 15 days at −20° C. After 30 days, about 10% activity was lost. After 90-180 days, a significant loss of about 12-15% (p<0.05) activity was observed. Non-lyophilized LSE kept in polypropylene tubes lost 0-5% (statistically insignificant) activity in 15 days, and about 13-16% (p<0.05) after 30-180 days. Lyophilized LSE stored in glass tubes lost only 0-5% activity in 180 days (statistically insignificant). Lyophilized samples stored in polypropylene tubes lost about 3-6% activity in 15 days and about 13%-20% (statistically significant) after 30-180 days.

Figure 19:
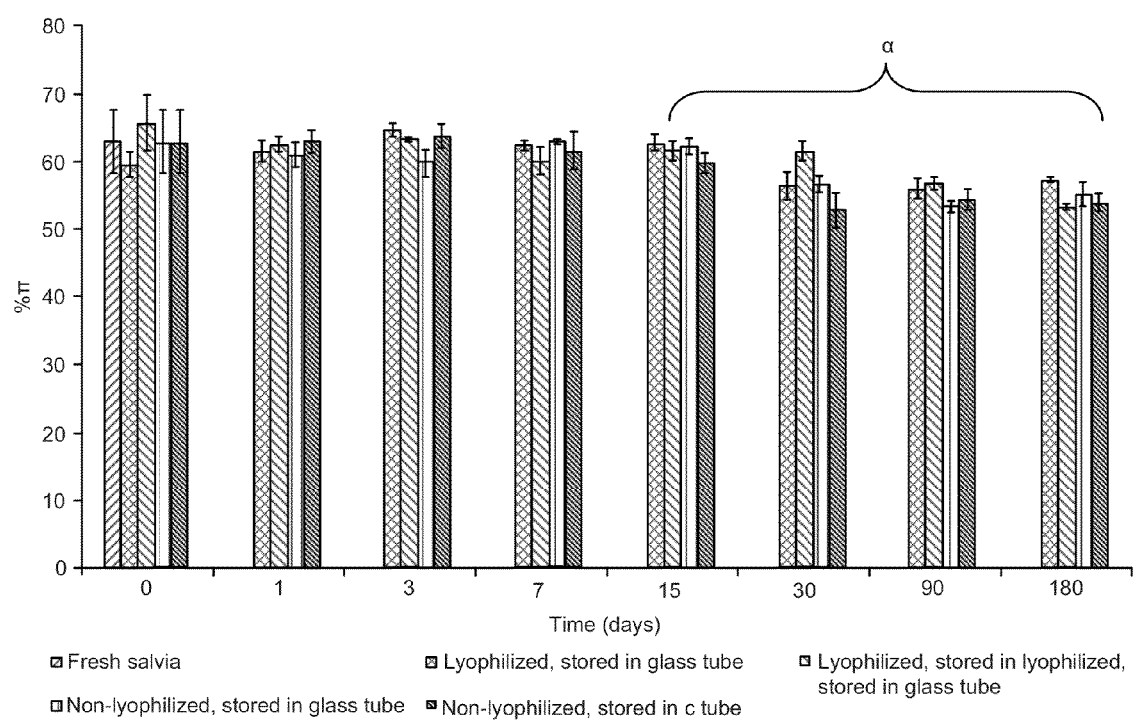
FIG. 19 shows the effect of container and lyophilization on antithrombin activity of LSE samples for up to 180 days at −20° C., according to some embodiments.

FIG. 19 shows the effect of container and lyophilization on antithrombin activity of LSE samples for up to 180 days at −20° C., according to some embodiments. The results are the mean±standard error of the mean SEM (n=3) and analyzed by General Linear Model (GLM), repeated measure ANOVA, using SPSS 18.0 software, and p<0.05 was considered statistically significant.

Example 4

A Method of Treating a Solid Tumor

This example shows the cytotoxic activity of the LSE prepared according to Example 1 in the treatment of a solid tumor.

REAGENTS: all reagents prepared as desired under strict sterile conditions per ESCO Class II Biological Safety Cabinet; Leibovitz's L-15 medium (from Sigma-Aldrich); phosphate buffered saline (PBS), 1× sterile solution (from Amresco); L-glutamine (L-Glu, liquid, 200 mM), penicillin/streptomycin (pen/strep, 100×), fetal bovine serum FBS mycoplex and ACCUTASE (a combination of protease and collagen in PBS with 0.5 mM EDTA) (from The Cell Culture Company PAA); trypan blue dye (from Merck); and CELL-TITER-GLO luminescent cell viability assay (from Promega); bovine serum albumin and arginine hydrochloride (from Sigma-Aldrich); sodium chloride (from Merck); Bradford reagent kit (from Amresco); carboplatin (cis-Diamine [1,1-cyclobutanedicarboxylato]platinum II) (from Calbiochem); Irinotecan hydrochloride (USP reference standard from Rockville, Md.).

EQUIPMENT: a Jouan CR22 refrigerated centrifuge (Jouan, France); a Memmert incubator type BE-400 (Memmert, Germany); an inverted microscope (from Olympus model CK30); a TECAN microplate luminometer (TECAN, USA); an Infinite M200, NanoQuant TECAN multi detection microplate reader (from TECAN (USA)); and a Christ freeze-drier model Alpha 1-4LD (Germany).

Methods

A human small cell lung cancer (SW1271 cell line) was obtained from the American Type Cell Collection ATCC. According to ATCC standard protocols, the anchorage dependent cell line was cultivated at an initial inoculums cell concentration of $10^4$ cells/cm$^2$ in 15 ml complete growth media (CGM) which consists of Leibovitz's L-15 medium supplemented with 10% FBS (v/v), 0.3 g/L of L-Glu, and 1% (v/v) pen/strep in a CORNING 75 cm$^2$ canted neck cell culture flask. The cultivated cells were incubated at 37° C. in CO$_2$-free humidified atmosphere. The CGM was stored at +4° C. and warmed (37° C.) for 15 min in a water bath prior to usage (ATCC, 2007). Flasks containing the cultivated cells were checked at 24 h intervals for cell viability, adherence, morphology and confluence state using the inverted microscope. Cultures were examined for any macroscopic evidence of microbial contamination by the inverted microscope. Media was changed as needed when media color turns to yellow, as Leibovitz's L-15 medium contains red phenol which becomes yellow at low pH levels and bright red at pH 7.4 which is suitable for cell culture (ATCC, 2007).

When the monolayer of anchorage-dependent cell line SW1271 is near 90% confluent, they were subcultured according to protocols provided by the ATCC. After aspirating the CGM from the flasks, the adherent cells were dissociated from the cell culture flask walls by pipetting 3 ml ACCUTASE. After an incubation period of 15 minutes with ACCUTASE at 37° C., cells were examined under the inverted microscope to be sure that most (95%) cells were detached and dispersed into a single-cell suspension (ATCC, 2007).

Counting the viable cells was done using trypan blue dye exclusion which depends on counting the unstained cells that have not uptake the dye appearing rounded with halos following the below protocol (NSF, 2006):

1. Trypan blue solution was prepared in sterile BPS to a final concentration of 0.4% (w/v).
2. Cell suspension was diluted by a sterile BPS to a total volume of 4 ml so that cell do not overlay on each other making counting difficult and inaccurate.
3. Both hemocytometer and coverslip, were cleaned, dried and assembled.
4. Cell suspension and trypan blue was mixed thoroughly at a ratio of 1:1 (creating a dilution factor of 2). Thence, 10 μl of the mixture was pipetted into the counting chamber of the hemocytometer. Touching the tips with the edge of the coverslip is sufficient to fill the chamber because of the capillary action.
5. Cell number in the square on each corner was counted and the average was considered.
6. The total cell number was estimated using the following equation:

$$\text{Total cell number} = \text{average count per square} \times \text{dilution factor} \times 10^4 \times \text{the total volume of the diluted cell suspension}$$

Cell suspension was homogenized by gentle pipetting and then dispensed at a final density of $10^4$ cells/cm$^2$ into new cell culture flasks containing 15 ml of CGM. The flasks were regularly monitored to check for cell viability and microbial contamination (ATCC, 2007).

When cells reached roughly 90% confluence, they were harvested as described above using ACCUTASE as a dissociating agent. The ACCUTASE was removed by gentle centrifugation (10 min, at +4° C. and 125×g) with the refrigerated centrifuge, the supernatant was discarded, and cells were re-suspended in 4 ml of CGM. The cells were counted using the trypan blue dye exclusion, and $10^4$ cells were seeded into a CORNING COSTAR 96-well flat bottom cell culture microplate containing 200 µl of CGM using 8-channel EPPENDORF micropipettor. The microplates were incubated at 37° C. in a free-$CO_2$ humidified environment for 24 hours (ATCC, 2007).

After the 24-hour incubation, the medium was discarded and replaced by new 180 µl of CGM. A series of double dilutions of the concentrated lyophilized leech saliva extract (10×LSE) was prepared. The 10×LSE was filtered through 0.2 µm SARTORIUS sterile filter paper and 20 µl aliquots were added to the first three rows of the microplate with the higher concentration in the first row and so forth making the total volume 200 µl (180 µl of CGM+20 µl of 10×LSE). To the next three rows, 20 µl volumes of another double dilution series of a ten-time concentrated of the phagostimulatory solution were added. Another negative control plate was prepared containing untreated cells ($10^4$ cells/well) cultivated in 200 µl of CGM.

Other plates were prepared following the same protocols by replacing 10×LSE by carboplatin and irinotecan as positive controls with a serial two-fold dilution of both starting from 100 µM in the first column. Two plates were prepared using 200 volumes of a double dilution series of mixtures consisting of:
 1. 10 µl of 10×LSE mixed with 10 µl of 100 µM carboplatin.
 2. 10 µl of 10×LSE mixed with 10 µl of 100 µM irinotecan.

All plates were incubated at 37° C. in free-$CO_2$ humidified atmosphere for 5 days. The antiproliferative or the cytotoxic effect of leech saliva extract was performed using a CELL-TITER-GLO luminescent cell viability assay based on measuring the luminescence signal from the reaction between the ULTRA-GLO recombinant luciferase and the ATP molecules produced by the metabolically viable cells in the presence of $Mg^{+2}$ and molecular oxygen (from Promega, 2009). A CELL-TITER-GLO assay was performed according to standard protocols:
 1. CELLTITER-GLO reagent was prepared by mixing CELLTITER-GLO buffer and the substrate which were previously equilibrated to room temperature.
 2. The 5-day incubated 96-well plates containing the experimental cells were allowed to be equilibrated to room temperature prior the assay. The medium was aspirated from all wells and replaced by 100 µl of new CGM.
 3. An equal volume of the prepared CELLTITER-GLO reagent (100 µl) was pipetted into the well, and then mixed for 2 min using the orbital plate shaker and let to stand at room temperature for 10 min to stabilize the luminescent signal.
 4. The reaction medium (CGM+CELLTITER-GLO reagent) was transferred into new white 96-well plate suitable for the luminometer used.
 5. Luminescence was recorded by the luminometer.
 6. Cell inhibition was calculated from the equation (Xu, Guo, Li, Wei, & Zhao, 2008):

$$\% \text{ inhibition} = \frac{\text{Control signal} - \text{Sample signal}}{\text{Control signal}} \times 100$$

7. The concentration of the test sample (LSE or the negative control) which inhibits 50% of cell growth ($IC_{50}$) was averaged from three replicates and estimated from plotting the percentage of cell growth inhibition against test sample concentration. (Hsu et al., 2011). Plots were carried out using a Four Parametric Logistic Equation using Sigma Plot 11.0 software.

After an incubation period of 5 days at 37° C. in $CO_2$-free humidified environment, the cells reached almost 90% confluence. The cells were harvested by detaching them from the cell culture flask walls with ACCUTASE and centrifuged at 4° C. and 125×g for 10 minutes. Cell counting with a trypan blue method revealed that one flask contains approximately $5.550-5.740 \times 10^6$ viable cells at near 90% confluence.

Figure 20:
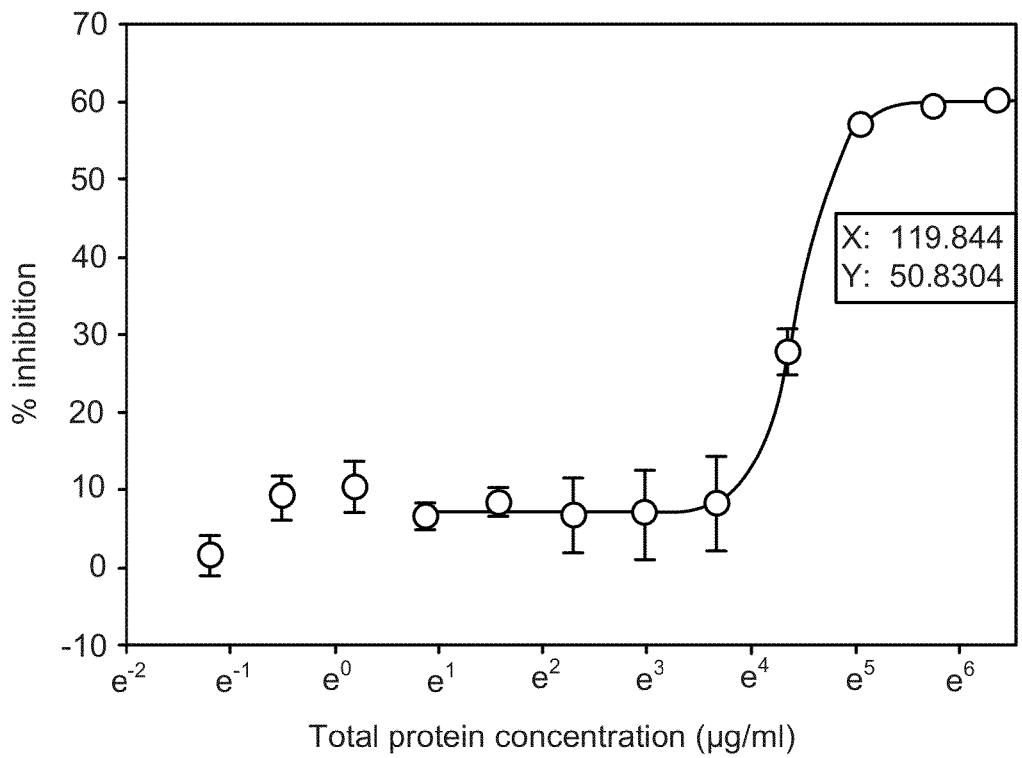
FIG. 20 shows that the LSE showed remarkable anti-proliferation activity against human small cell lung cancer (SW1271 cell line), according to some embodiments.

FIG. 20 shows that the LSE showed remarkable anti-proliferation activity against human small cell lung cancer (SW1271 cell line), according to some embodiments. The concentration of total LSE protein that inhibits growth of 50% of the cells after 5 days incubation ($IC_{50}$) was 119.844 µg/ml, estimated by plotting percent inhibition against total protein concentration. The phagostimulatory solution alone had no effect on cell proliferation.

Figure 21:
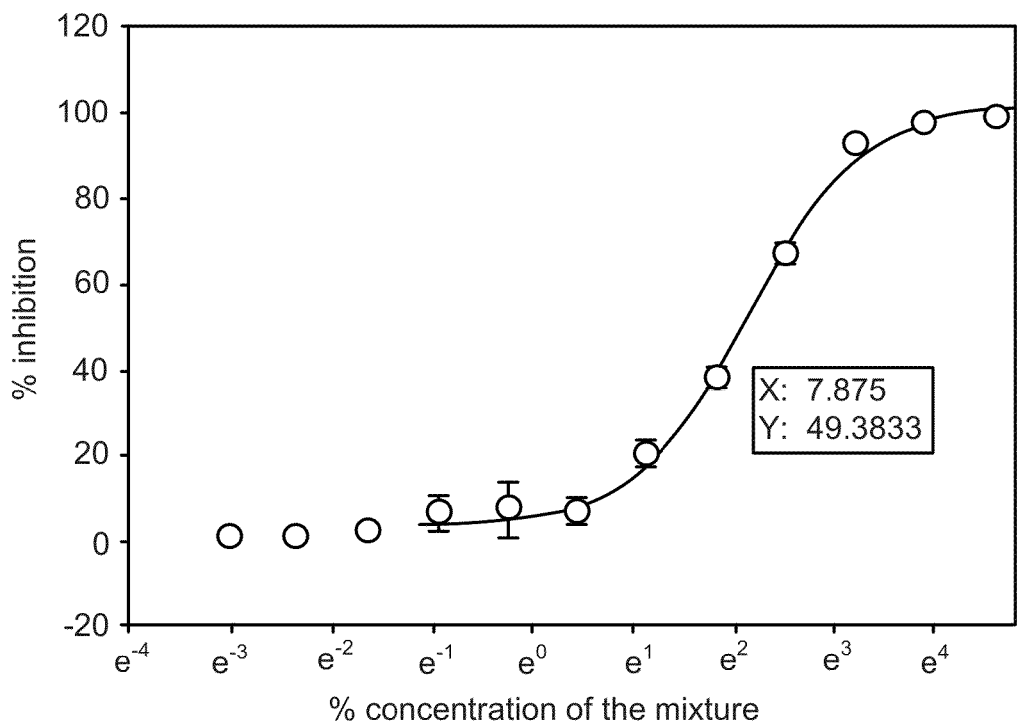
FIGS. 21 and 22 show the cytotoxic effect of mixtures of LSE with irinotecan or carboplatin, according to some embodiments.
Figure 22:
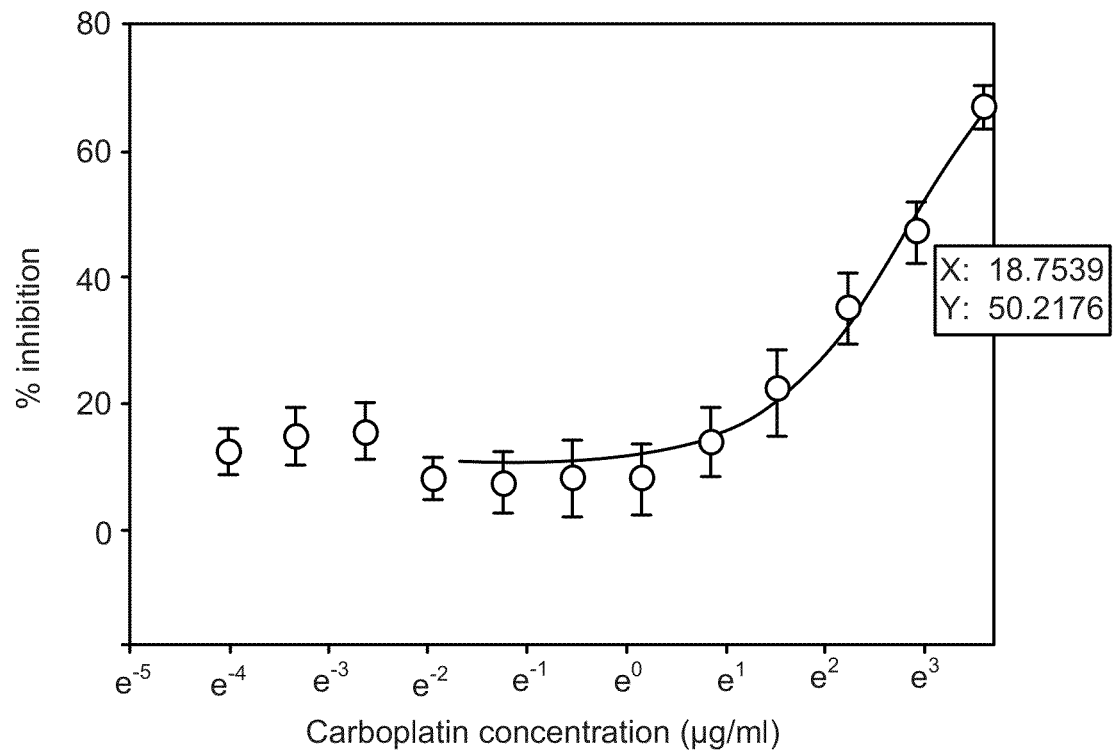

FIGS. 21 and 22 show the cytotoxic effect of mixtures of LSE with irinotecan or carboplatin, according to some embodiments. The $IC_{50}$ of irinotecan and carboplatin were 5.813 µg/ml and 18.754 µg/ml, respectively. All measurements were repeated in triplicate, and the mean±the standard error of the mean SEM (n=3) were considered. Plots were generated using Four Parametric Logistic Equation with Sigma Plot 11.0 software.

A combination of LSE and irinotecan showed an $IC_{50comb}$ of 51.463 µg/ml which is about 57.1% less than the $IC_{50}$ of LSE used alone. A combination of LSE and carboplatin show an $IC_{50comb}$ of 114.261 µg/ml, a 4.6% reduction in $IC_{50}$. Carboplatin showed a dramatic decline in $IC_{50}$ value by 65%, such that $IC_{50comb}$ of carboplatin and LSE was 6.449 µg/ml.

The results suggest that LSE, alone or in combination with other agents such as irinotecan or carboplatin could be useful in treating other forms of cancer, such as prostate, breast, and liquid cancers such as leukemias and lymphomas. Acute myeloid leukemia is of particular interest.

Example 5

A Method of Treating a Diabetes

This example shows the effectiveness of LSE in treating diabetes. The LSE isolation and total protein measurement was done according to the methods taught herein.

Materials and Methods:

Sodium chloride, arginine hydrochloride, absolute ethanol and formaldehyde 37% (from Merck); Bradford reagent kit (Amresco Inc.); Parafilm membrane (from American Can Company); anhydrous glucose (from Fisher Scientific); alloxan monohydrate used to induce diabetes (from Sigma Aldrich); bovine serum albumin (from Sigma Aldrich); insulin from bovine pancreas (≥27 units/mg) (from Sigma Aldrich); the method of preparing Alloxan solution in ice-cold normal saline immediately prior to injection (from Lenzen, 2008).

Centrifugation was done using Universal 32R centrifuge (from Hettich ZenTrifugen, Germany); microplate reader model INFINITE M200, NANOQUANT TECAN (from TECAN USA); lyophilization performed using a CHRIST freeze-drier model Alpha 1-4LD (Germany); a ONE TOUCH ULTRA glucometer and test strips used for the determination of blood glucose concentration (from LifeScan Inc., USA); and, a NIKON ECLIPSE 80i microscope.

Male rats of Sprague Dawley strain (SD) (from Mikro Makmur Enterprise, Kuantan, Pahang Darul Makmur, Malaysia) were grouped randomly and kept at an animal post-graduate laboratory in Kulliyyah of Pharmacy, International Islamic University Malaysia (IIUM), maintained with an air conditioning system and exhaust fans. The rats were under a 12 h/12 h dark and light cycle at room temperature (25° C.). They were acclimatized to these conditions for one week prior to the experiment and housed in polypropylene cages lined with pine wood husk changed every two days. The rats were given free access to tap water and a commercial dry pellet diet, Gold Coin. The experimental procedures were conducted according to Principles and Guide to Ethical Use of Laboratory Animals approved by Ministry of Health Malaysia (Sinniah & Hussein, 2000). The experimental protocols were approved by Ethics Committee Meeting (No. 1/2011 on 22 Apr. 2011) of Kulliyyah of Medicine, IIUM (Ref. No. IIUM/305/20/4/10).

The rats were fasted overnight and a type-1-like diabetes was induced by a single-dose intraperitoneal (i.p) administration of freshly prepared alloxan solution 160 mg/kg body weight (b.w.) (Rajakopal & Sasikala, 2008). In order to prevent fatal alloxan-induced hypoglycemia, the rats were administered a 20% glucose solution intraperitoneally followed by a 5% glucose solution orally for the next 12 hours (Lenzen, 2008). The rats were then fed a commercial pellet diet ad libitium and given free access to tap water. All experimental animals were injected three times with alloxan at 24 hours intervals.

After 24 hours of alloxanisation, the fasting blood glucose concentration (FBG) was measured every morning to check the diabetic state of the injected rats. All FBG values were taken from fresh capillary blood from a tail vein puncture, and measurements were taken using a ONE TOUCH ULTRA glucometer. After three days of alloxan injection, the rats showed FBG levels of more than 11.1 mmol/L, a level considered diabetic for the study (Abeeleh et al., 2009).

Forty male rats were divided randomly into eight groups, each comprising five rats as detailed below:
  Group I: normal control rats, neither alloxan nor LSE was injected into this group.
  Group II: induced-diabetic control rats injected only with alloxan solution i.p
  Group III: induced-diabetic rats injected subcutaneously (s.c) with LSE 500 μg/kg b.w which corresponds to the protein amount/dose given by one leech.
  Group IV: induced-diabetic rats injected s.c with LSE 1000 μg/kg b.w which corresponds to the protein amount/dose given by two leeches.
  Group V: induced-diabetic rats injected s.c with the phagostimulatory solution PhS1 (0.001M arginine in normal saline) in a dose of 20 ml/kg b.w which contains the amount of the arginine and sodium chloride that is supposed to accompany the higher dose of LSE injected to the group IV.
  Group VI: induced-diabetic rats injected s.c with 20 units/kg b.w bovine pancreas insulin suspension in distilled water (Booth & Brookover, 1968).
  Group VII: induced-diabetic rats injected s.c with 10 units/kg b.w bovine pancreas insulin suspension in distilled water (Booth & Brookover, 1968).
  Group VIII: induced-diabetic rats injected s.c with 250 μg/kg b.w LSE+10 units/kg b.w bovine pancreas insulin.

The antihyperglycemic activity of LSE was assessed by the fall in FBG values within eight hours. Fasting blood glucose (FBG) at two-hour intervals was recorded during the experiment period for all the experimental animals. The percentage decrease in fasting blood glucose concentration was calculated from the following equation (Madubunyi, Onoja, & Asuzu, 2010):

$$\text{Percentage decrease in } FBG = \left[ \frac{FBG \text{ before treatment}(0 \text{ hr}) - FBG \text{ after treatment }(x \text{ hr})}{FBG \text{ before treatment }(0 \text{ hr})} \times 100 \right]$$

Thirty male rats were divided randomly into six groups, each comprising five rats as detailed below:
  Group A-I: rats injected i.p with a single dose of alloxan (160 mg/kg b.w).
  Group A-II: rats injected i.p with two doses of alloxan (160 mg/kg b.w) at 24-hour interval.
  Group A-III: rats injected i.p with three doses of alloxan (160 mg/kg b.w) at 24-hour interval.
  Group A-IV: rats injected s.c with a single dose of LSE (250 μg/kg b.w) followed after one hour by a single dose i.p of alloxan (160 mg/kg b.w).
  Group A-V: rats injected s.c with two doses of LSE (250 μg/kg b.w) followed after one hour by two i.p doses of alloxan (160 mg/kg b.w) at 24-hour interval.
  Group A-VI: rats injected s.c with three doses of LSE (250 μg/kg b.w) followed after one hour by three i.p doses of alloxan (160 mg/kg b.w) at 24-hour interval.

The prophylactic activity of LSE was assessed by measuring FBG after 24 hours of each injection. Rats that exhibited FBG values between 8.3 and 13.9 mmol/L were considered as mild diabetic and those with FBG of more than 13.9 mmol/L were considered as severe diabetic (Gupta et al., 2009).

Figure 23:
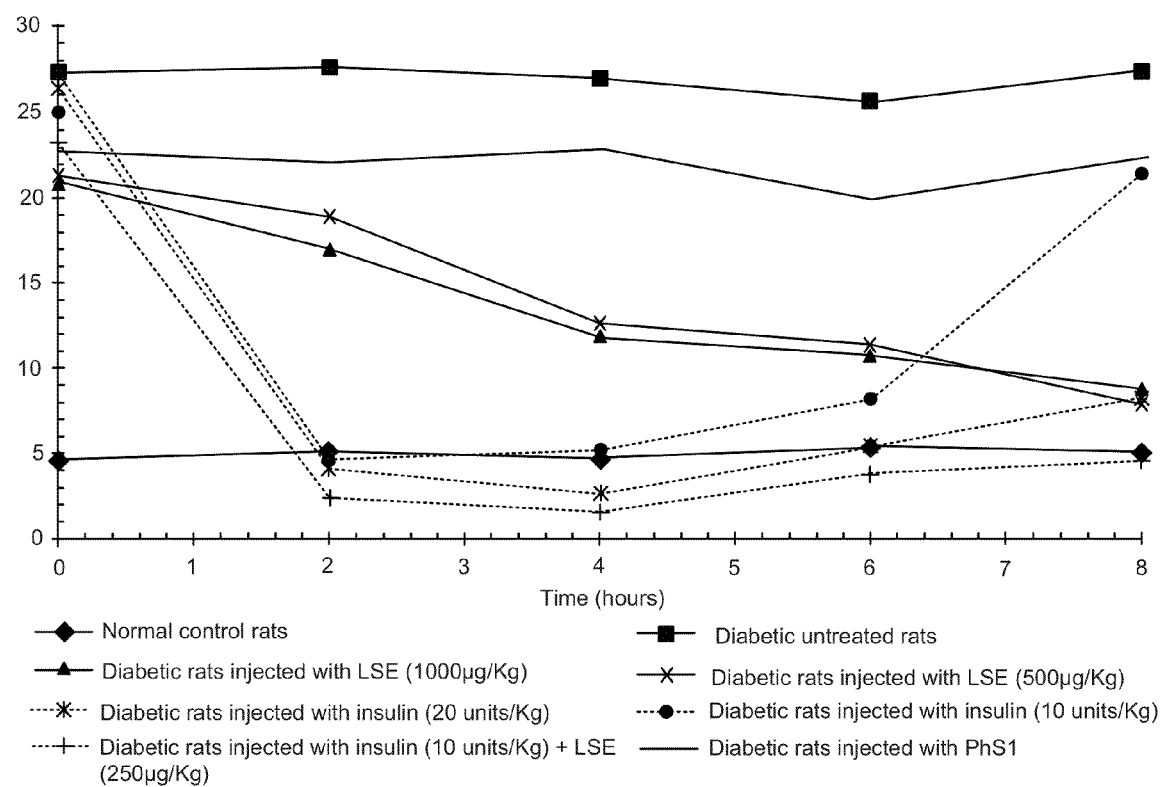
FIGS. 23 and 24 show the effect of different doses of LSE and insulin on fasting blood glucose (mmol/L) in normal and diabetic rats at various time intervals (h), according to some embodiments.
Figure 24:
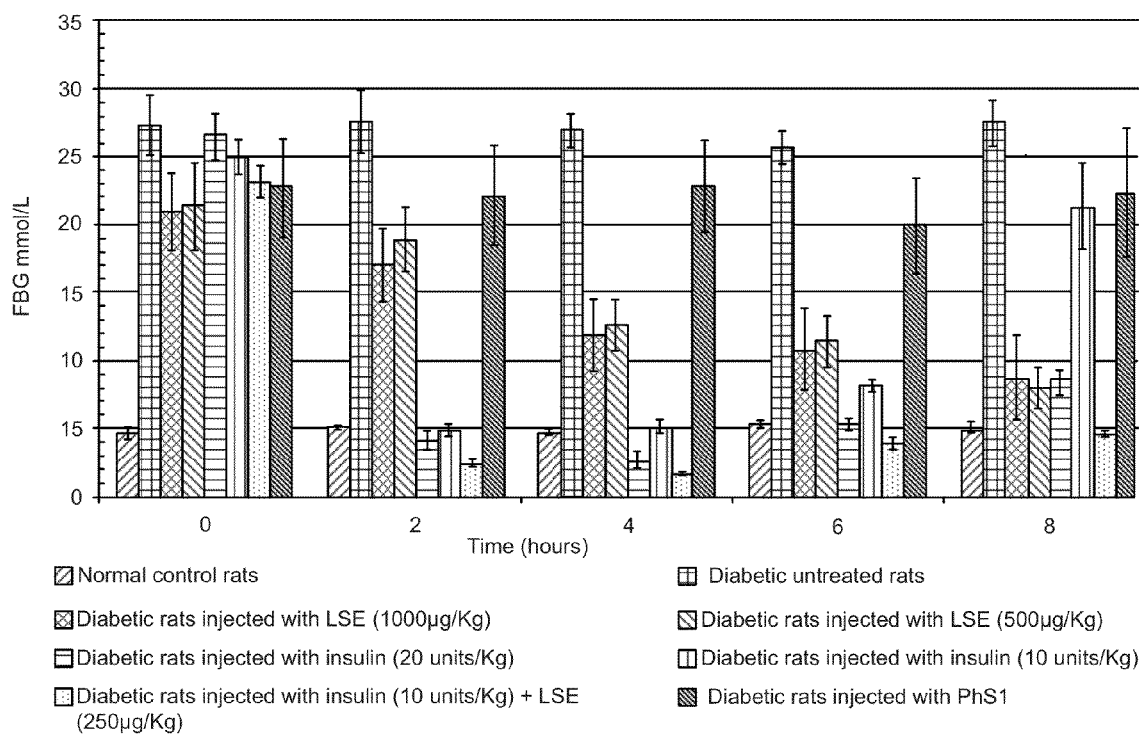

FIGS. 23 and 24 show the effect of different doses of LSE and insulin on fasting blood glucose (mmol/L) in normal and diabetic rats at various time intervals (h), according to some embodiments. After three days of intraperitoneal alloxan injection (160 mg/kg b.w), the FBG increased significantly (p<0.001) in the FBG in the diabetic control rats when compared with the normal control ones. The FBG levels were significantly reduced after injecting rats with LSE subcutaneously at both doses of 1000 and 500 μg/kg b.w. The LSE at a dose of 1000 μg/kg b.w resulted in a higher significant decline (p<0.001) in FBG than that of the dose 500 μg/kg (p<0.05). In addition, a significant reduction in FBG (p<0.05) occurred after two hours of injection with LSE, and a higher significant decline was noticed after four, six and eight hours (p<0.001).

All insulin-injected rats experienced a sharp significant decrease (p<0.001) in FBG after two hours of injection. Rats injected with the lower dose of insulin (10 units/kg b.w) returned to the diabetic state with rapid increasing FBG values after 8 hours of treatment. Rats that received insulin (10 units/kg) and LSE (250 μg/kg) exhibited a significant drop in FBG during the whole 8-hour study period. Diabetic rats injected with the phagostimulatory solution showed no significant reduction in FBG compared with the diabetic control group. No significant difference was seen between the normal rats and the diabetic rats treated with LSE or insulin at either dose.

Neither mortality nor a behavioural change was observed amongst the all saliva-injected animals until the end of the study. All these animals exhibited typical locomotion and physical activity, such as no signs of weakness or aggressiveness. No toxicity reaction were noticed for example no anorexia, ataxia, piloerection, loss of weight, diarrhoea, urination, breathing difficulty and noisy breathing. Simultaneous administration of LSE (250 µg/ml b.w) and insulin (10 units/kg b.w) induced hypoglycemia with no mortality. No signs of acute toxicity were observed in rats injected subcutaneously with LSE at both doses of 1000 and 500 µg/kg b.w, On the other hand, injection insulin at a dose of 20 units/kg b.w resulted in a hypoglycemic condition in all rats leading to the death of one rat. The other rats which stayed alive showed less physical activity especially during the first two hours of injection.

Figure 25:
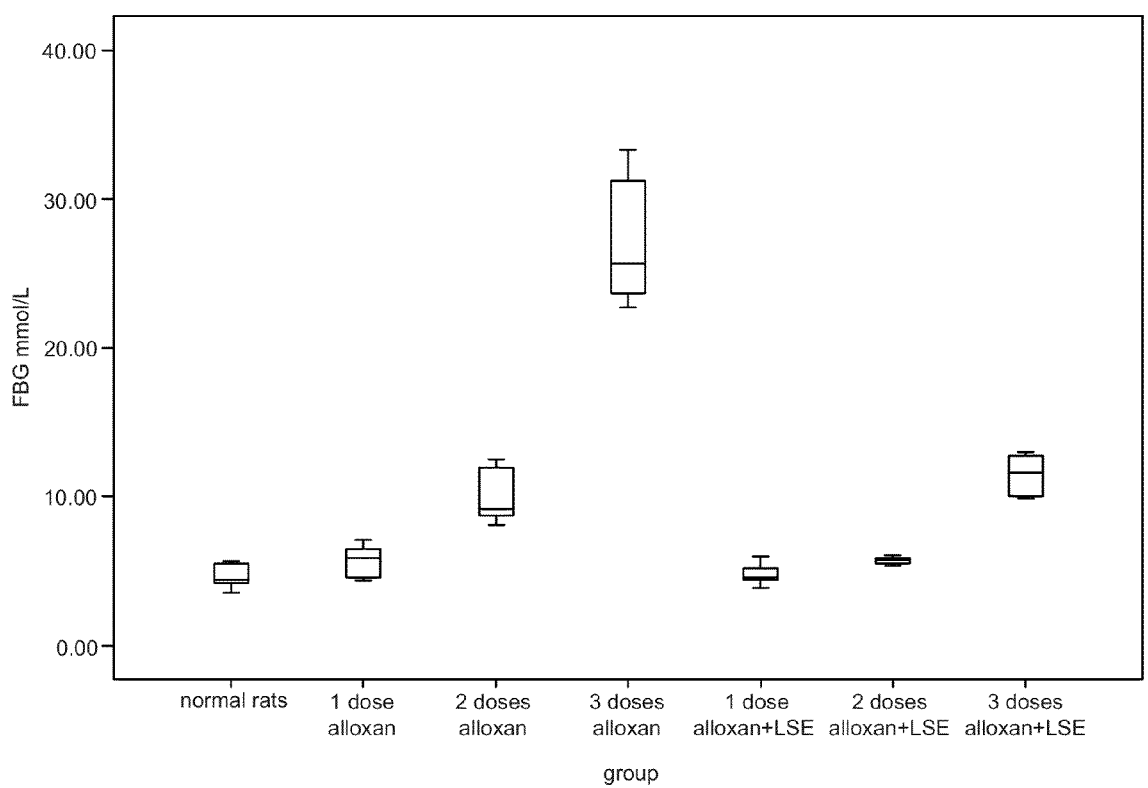
FIG. 25 shows that the LSE has a prophylactic effect on the onset of diabetes, according to some embodiments.

FIG. 25 shows that the LSE has a prophylactic effect on the onset of diabetes, according to some embodiments. For example, without use of LSE as a prophylactic, one dose of alloxan (160 mg/kg b.w) was not enough to induce diabetes in the rats, two doses made all rats mildly diabetic (10.1±2.0 mmol/L), and three doses induced severe diabetes (27.3±2.1 mmol/L). None of the rats injected with one dose of LSE (250 µg/kg b.w) before alloxanisation got diabetic at all. Two doses of LSE were able to prevent diabetic induction in all rats when injected one hour before the alloxan injection. Only rats which received three doses of alloxan after three doses of LSE became mild diabetic (11.5±0.6 mmol/L). The results are the mean of triplicates±the standard error of the mean SEM (n=5), analyzed using one-way ANOVA and Tukey's HSD post hoc test; $p<0.05$ was considered statistically significant. $P<0.05$ when compared with rats injected with two doses of alloxan and LSE. $p<0.001$ when compared with rats injected with three doses of alloxan and LSE.

Example 6

A Method of Treating a Viral Disease

This example will be used to show the effectiveness of LSE at treating a viral disease. The LSE isolation and total protein measurement will be done according to the methods taught herein.

A tissue culture generally a chicken embryo 3-6 days old will be infected in side the embryo membrane by a dose of live viruses (hepatitis C, HIV, Dengue, West Nile, and Influenza H1N1, H5N1) if necessary a multiple infections will be used until the infection takes place.

After a period of incubation, embryo growth and changes in their tissues will be monitored according to established procedures. This infected tissue culture will serve as a control. Three other cultured tissues will be prepared by the same method. In the first one, four doses of LSE (100/250/500/1000 ug/b.w) will be injected before the viral infection. In the second tissue culture, four doses of LSE (100/250500/1000 ug/b.w) will be injected at 1, 2, 3. 4 hours after the viral infection. In third a tissue, four doses of inactivated LSE (100/250/500/1000 ug/b.w), will be injected after and before infection. The aim in the third experiment is to analyze any change in signal pathways and comparison with the active LSE will be made in order to have an indication of the mechanism of action. The three cultured tissues: treated after and before and with inactivated LSE will be monitored and compared to the control tissue.

The effect LSE on viral infection will be then deduced according to established procedures and will be compared to the conventional drugs like interferon.

Example 7

A Method of Treating a Parasitic Disease

This example will be used to show the effectiveness of LSE at treating a parasitic disease. The LSE isolation and total protein measurement will be done according to the methods taught herein.

In the case of malaria, an animal model, generally a mouse model will be injected by a dose of a malaria parasite (the dose will be determined according to the virulence of the parasite Spp) until the animals develop the desired symptoms of malaria. The sick animals will be injected (SC or IV mode) by two doses (500/1000 ug/K b.w LSE). After treatment, blood drops will be taken from the mice tail on glass slides for examination under the microscope. or for ELIZA testing.

We will use eight groups of ten mice each as follows:
1. Group A—control infective positive
2. Group B—Infected & treated with LSE (500 ug/K bw) after 1, 2, 3, 4.hours
3. Group C—Infected & treated with LSE (1000 ug/K bw) after 1, 2, 3, 4.hours
4. Group D—½ hour before the infection with the parasite we inject it with LSE (500 ug/K bw) as prophylactic measures.
5. Group E—½ hour before the infection with the parasite we inject it with LSE (1000 ug/K bw) as prophylactic measures.
6. Group F & G—Infected mice injected with 500 & 1000 ug/K bw of phagostimulatory solution.

Blood smears will be taken from the tail of the mice daily and examined under a light microscope for seven days to monitor the activity of the LSE. The last (H) infected group will be treated with a standard antimalaria drug to monitor the relative activity and potency of LSE on the parasite.

Example 8

A Method of Administering an Antioxidant Therapy

This example shows the antioxidant activity of LSE. The LSE isolation and total protein measurement was done according to the methods taught herein.

Materials and Methods

Methanol (MeOH) (from Fischer Scientific); L-Ascorbic acid (from Calbiochem); arginine hydrochloride, bovine serum albumin (BSA), and DPPH (2,2-Diphenyl-1-picrylhydrazyl) (from Sigma Aldrich); sodium chloride (NaCl) (from Merck).

An Infinite M200, NanoQuant TECAN multi detection microplate reader (from TECAN (USA)); a Hettich ZenTrifugen Universal 32R centrifuge (Germany); a CHRIST freeze-drier model Alpha 1-4LD (Germany).

Antioxidant activity was determined using known methods (Blois, 1958) of measuring radical scavenging ability using 2,2-diphenyl-1-picrylhydrazyl (DPPH) (Althunibat et al., 2009; Blois, 1958; Sanja, Sheth, Patel, Patel, & Patel, 2009):
1. Preparation of DPPH solution: a DPPH solution (0.002M) was prepared by dissolving 4.3 mg DPPH in 3.3 ml MeOH. The resultant solution was protected from light by covering the container with an aluminum foil.
2. Preparation of test sample: The lyophilized LSE was dissolved in the minimum amount of distilled water (2 ml). The volume was brought to a final volume of 6.6 ml by MeOH yielding a 3-time concentrated LSE, and the resultant methanol solution was termed as 3×mLSE. Volumes of 100 µl of serial double-fold dilutions of the 3×mLSE were pipetted into a 96-well plate. All volumes were brought to a final volume of 300 µl by MeOH.
3. Preparation of standard solution: A stock solution of ascorbic acid (50 µg/ml) was prepared by dissolving 500 µg of ascorbic acid in 10 ml MeOH with vigorous shaking. Serial step-wise dilutions were prepared in the 96-well plate by taking different volumes of the stock solution and diluting them with MeOH up to 300 µl, corresponding to final concentrations of 50, 40, 30, 20, 10, 5 and 2.5 µg/ml.
4. Experimental protocols: A volume of 15 µl of DPPH solution (0.002M) was added to 300 µl of MeOH. Immediately, the absorbance at 516 nm ($A_{516}$) was measured as a control reading. 15 µl of DPPH solution was added to the test samples and standard solutions. The $A_{516}$ of the test samples were taken after 15 min, and the same procedures were used with PhS1 as a negative control.
5. Calculations: The free radical scavenging activity (% antiradical activity) was estimated from the equation:

$$\% \text{ antiradical activity} = \frac{\text{Control absorbance} - \text{Sample absorbance}}{\text{Control absorbance}} \times 100$$

Figure 26:
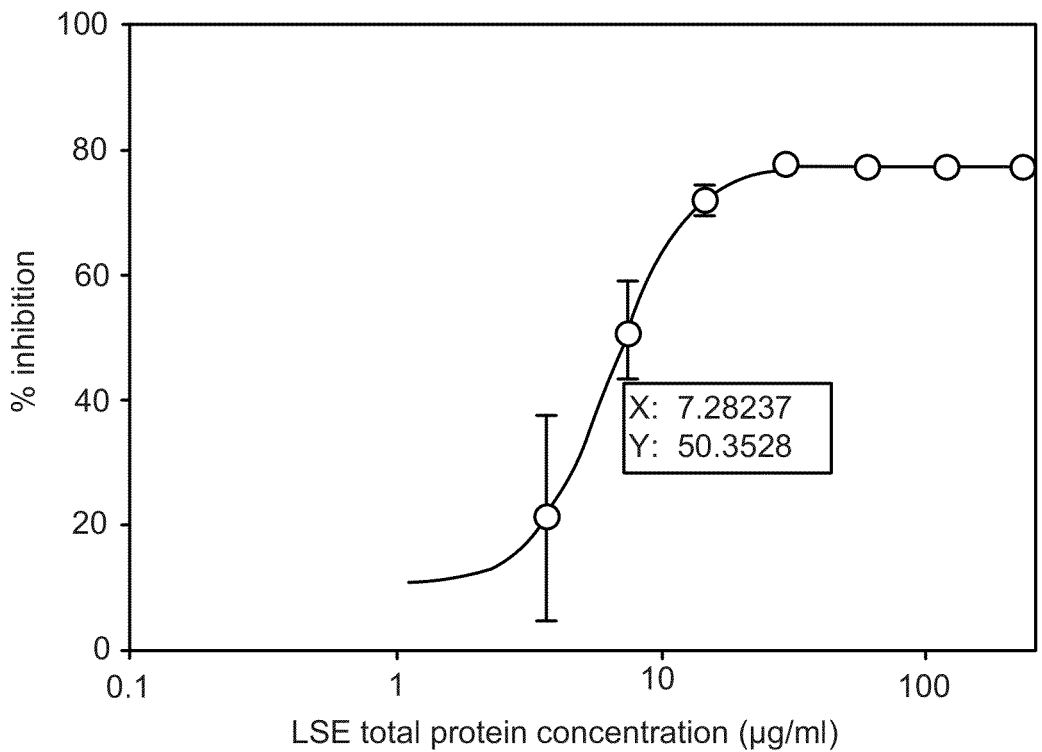
FIGS. 26 and 27 compare the free radical scavenging activity of LSE to L-ascorbic acid (vitamin C), according to some embodiments.
Figure 27:
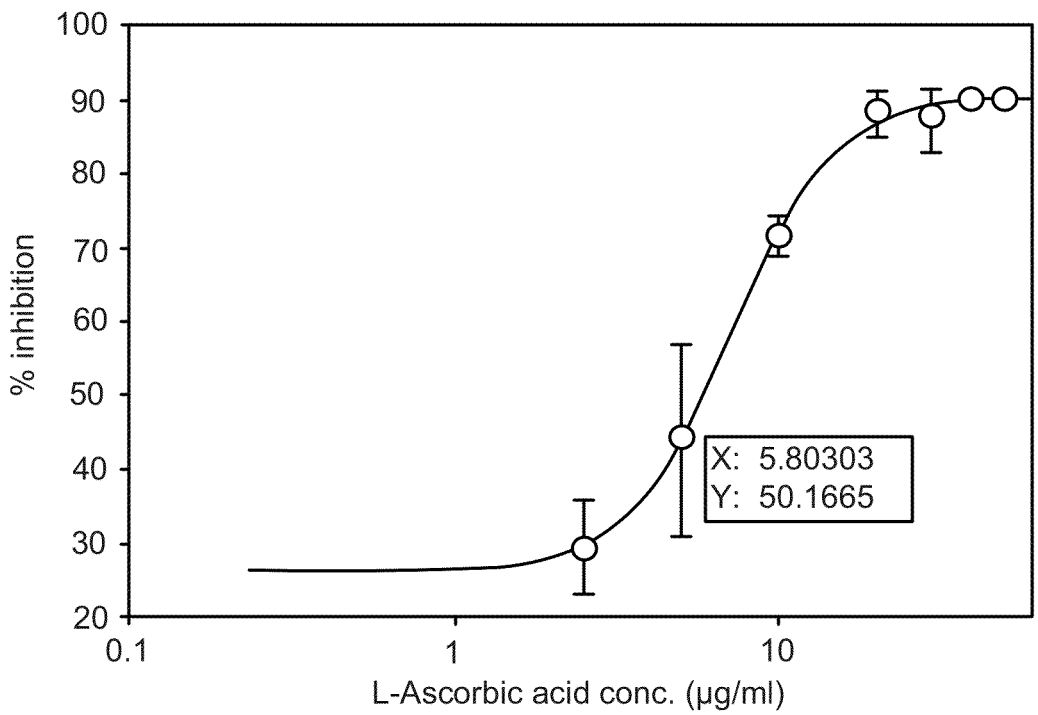

FIGS. 26 and 27 compares the free radical scavenging activity of LSE to L-ascorbic acid (vitamin C), according to some embodiments. All measurements were repeated in triplicate, and the mean±SEM was considered. The concentration of ascorbic acid and the LSE proteins (µg/ml) required for scavenging 50% of DPPH ($IC_{50}$) was estimated from the curve resulted from plotting % antiradical activity against concentrations (µg/ml). Plots were carried out using Four Parametric Logistic Equation using Sigma Plot 11.0 software.

A dose-dependent free radical scavenging activity was shown by the LSE having an $IC_{50}$ of 7.282 µg/ml. Similarly, L-ascorbic acid was found to be a free radical scavenger with $IC_{50}$ of 5.803 µg/ml.

Example 10

A Method of Administering an Antibacterial Therapy

This example shows the effectiveness of LSE as an antibacterial.

Methods and Materials

Mueller-Hinton agar (MHA) and Mueller-Hinton broth (MHB) (from Oxoid Ltd.); potato dextrose agar (PDA) and potato dextrose broth (PDB) (from Liofilchem); antimicrobial susceptibility test discs containing 5 µg/disc ciprofloxacin and 100 units/disc nystatin (from Oxoid Ltd); bovine serum albumin and arginine hydrochloride (from Sigma-Aldrich); sodium chloride (NaCl) (from Merck); Bradford reagent kit (from Amresco).

a Laminar Flow Hood Jouan (Jouan SA, France); an incubator Memmert/INB 400 and water bath Memmert/WNB 22 (from Memmert GmbH, Germany); a HIRAYAMA/HV-85 Autoclave (HIRAYAMA Corporation, Japan); a HITACHI U-1900 Spectrophotometer (from HITACHI High-Tech (Japan)); sterile 96-well plates (from Greiner Bio-One Corporation): a centrifuge Hettich ZenTrifugen Universal 32R (Germany).

Reference strains of human pathogens were used including Gram-positive bacterial spp. (*Bacillus cereus* ATCC25923 and *Staphylococcus aureus* ATCC25923), Gram-negative bacterial strains (*Pseudomonas aeruginosa* ATCC27853, *Escherichia coli* ATCC35218 and *Salmonella typhi* from Institute of Medical Research Health Ministry IMR) and two fungal strains (*Candida albicans* ATCC10231 and *Cryptococcus neoformans* ATCC90112).

All media used during the experimental procedures were prepared according to the manufacturer instructions, as the following:
1. Muller-Hinton agar (MHA): was prepared by suspending 38 g of MHA in 1 L distilled water with boiling and frequent vigorous agitation until completely dissolved. Then, it was sterilized by autoclaving at 121° C. for 15 minutes.
2. Muller-Hinton broth (MHB): was prepared by suspending 21 g of MHB in 1 L distilled water with boiling and frequent vigorous agitation until completely dissolved. Then, it was sterilized by autoclaving at 121° C. for 15 minutes. The resultant stock sterile broth was kept in a well closed 1000-ml screw-cap bottle, wrapped with parafilm membrane at the cap and stored at +4° C. for further usage. Before usage, MHB was warmed (37° C.) in the incubator for 15 minutes.
3. Potato dextrose agar (PDA): was prepared by suspending 39 g of PDA in 1 L distilled water with boiling and frequent vigorous agitation until completely dissolved. Then, it was sterilized by autoclaving at 121° C. for 15 minutes.
4. Potato dextrose broth (PDB): was prepared by suspending 26.5 g in PDB 1 L distilled water with boiling and frequent vigorous agitation until completely dissolved. Then, it was sterilized by autoclaving at 121° C. for 15 min. The resultant stock sterile broth was kept in a well closed 1000-ml screw-cap bottle, wrapped with parafilm membrane at the cap and stored at +4° C. for further usage. Before usage, PDB was warmed (37° C.) in the incubator for 15 minutes.

Before pouring of agar, the freshly prepared sterilized agar medium MHA/PDA for bacterial/fungal strains, was allowed to cool in water bath adjusted at 50° C. for 15-30 minutes in order to prevent the formation of moisture droplets by condensation phenomenon. Thereafter, a volume of about 20-25 ml was poured into disposable flat-bottom sterile (gamma-irradiated) Petri dishes to a height of 4 mm avoiding trapping any air bubbles. The plates with lids ajar were left to equilibrate at room temperature for about 15 minutes under the laminar flow to get rid of excess surface moisture and temperature. Finally, the plates were covered, inverted downside upwards and stored in the refrigerator (+4° C.) to be used within a maximum period of one week. Before inoculation of the agar-containing plates, they were equilibrated to room temperature for about one hour in order to minimize condensation (Coyle, 2005; Goldman & Green, 2009; Lalitha, 2004).

A turbid-metric assay was carried out to standardize the microorganism number used for inoculation. The Direct Colony Suspension method was used to prepare inoculation suspension (Coyle, 2005; Goldman & Green, 2009; Lalitha, 2004; Rex, Pfaller, Rinaldi, Polak, & Galgiani, 1993). Experimental procedures include the following steps:
1. Preparation of Barium Sulfate (0.5 McFarland) standard suspension: It was prepared by adding 0.5 part of 0.048M $BaCl_2$ to 99.5 parts of 0.18M $H_2SO_4$ and agitated vigorously until a homogenous suspension was obtained. The turbidity of the suspension was verified by measuring the optical density at 625 nm ($OD_{625}$) by the spectrophotometer. Proper dilutions were done to get an absorbance value of 0.008-0.10 which corresponds to 0.5 McFarland standards. The prepared standard suspension was aliquoted into small screw-caps glass bottles, stored at room temperature and protected from light. Before utilization, the bottles were stirred well by vortex to maintain a uniform suspension.

2. Direct Colony Suspension method:
   a) Under aseptic condition, five colonies isolated by ignition-sterilized inoculation loop from 18-24-hour cultivated agar plates of each microbe were suspended separately in 20 mL pre-warmed (37° C.) broth medium (MHB for bacterial strains or PDB for fungi stains) kept in screw-cap bottles and incubated at 37° C.
   b) During the incubation period, aliquots of 1 mL were taken from the culture at hourly intervals and the optical density ($OD_{625}$ for bacterial suspension and $OD_{530}$ for fugal suspension) were measured using the spectrophotometer.
   c) Proper dilutions by MHB/PDB were done in order to adjust the microorganism suspension to match the 0.5 McFarland turbidity standards. Broth suspension and the Barium Sulfate 0.5 McFarland standard were compared by the naked eye against a card with a white background and black lines. Finally, the resultant broth suspensions contained $10^7$ CFU/ml for bacterial spp. and $10^4$ CFU/ml for fungal spp. which were used for all experiments performed.
   d) Suspensions were always agitated thoroughly before OD measurement and inoculation.

The Kirby-Bauer Disc Diffusion method was used for determining antimicrobial activity of LSE:

1. Inoculation of test plates: a sterile cotton swab was immersed and rotated many times in the adjusted microorganism suspension. The immersed swab was pressed strongly till all excess fluids were removed. The swab was passed over the dried sterile agar surface of MHA-containing plates for bacterial strains or PDA-containing plates for fungal strains. These steps were repeated three times by spreading the broth suspension using glass rod in order to get evenly inoculated plates. The plates were left open under the laminar flow hood for 5 minutes to allow the surface to absorb the extra moisture.

2. Preparation of dried filter paper discs: WHATMAN filter paper No. 1 was used to prepare discs approximately 6 mm in diameter. These discs were dipped in test solution (LSE or PhS1, steriled by filtration through 0.2 μm sterile SARTORIUS filter paper). Thereafter, they were allowed to dry for 5 minutes in the incubator (37° C.) before application onto the Petri dishes. The discs were left at room temperature for about 15 minutes before placement to the inoculated agar Petri dishes.

3. Discs placement to the inoculated agar Petri dishes: The filter discs loaded with test solution (LSE/PhS1) and reference antibiotic-containing discs (5 μg/disc ciprofloxacin or 100 units/disc nystatin) were laid down on the inoculated agar plates using sterile forceps with gentle pressing to ensure a good adherence to the agar surface. The discs were distributed to be at least 15 mm from the edge of the plate and no closer than 24 mm from center to center. Lastly, the plates were inverted upside downward and incubated at 37° C. for 24 h and 48 h for bacterial and fungal spp., respectively.

After the incubation period, the zone of inhibition (mm) around each disc was measured using a ruler and compared with the reference antibiotics used.

Microdilution was used to determine the minimal inhibitory concentration (MIC), which is the minimal concentration of LSE protein content that can inhibit the growth of the test organism. Serial double-fold dilutions of LSE were carried out in a sterile 96-well plate. 100 μl of sterile Mueller-Hinton broth was pipetted into the first five columns wells of the plate. 100 μl of LSE was mixed with the broth in the first three wells of the first row of the plate. Dilutions were made by transferring 100-μl aliquots of the mixture from the first three wells into the next ones vertically, and so forth. 10 μl of the test organism suspension broth containing ($10^7$ CFU/ml) was pipetted into each well of the first four columns, but no inoculum was added to the fifth column. The fourth and the fifth columns were considered as positive (broth with inoculum) and negative control (broth only), respectively. The plate was covered, wrapped with parafilm sheets around the edges to avoid dehydrating, and incubated for 24 hours at 37° C. After the incubation period, the MIC endpoint was determined by a lack of turbidity in the well.

The antibacterial and antifungal activities of the fresh LSE and the lyophilized samples are shown in Table 3 with ciproflaxin and nystatin, where the LSE is shown to have desired activity.

TABLE 3

| Sample | Starvation period (weeks) | Bacterial spp. | | | | | Fungal spp. | |
|---|---|---|---|---|---|---|---|---|
| | | S. aureus | P. auroginosa | Sal. typhi | E. coli | B. cereus | C. albicans | C. neoformance |
| | | Zone of inhibition (mm) | | | | | | |
| Fresh LSE | 16 | — | 0 | 22 | 25 | 0 | — | — |
| | 22 | 0 | 0 | 0 | 0 | 0 | — | — |
| | 26 | 0 | 0 | 0 | 0 | 0 | — | — |
| Lyoph. LSE | $22^a$ | 11 | 0 | 10 | 0 | 0 | 0 | 0 |
| | $26^b$ | 0 | 0 | 0 | 0 | 0 | 0 | 0 |
| Arginine + $NaCl^c$ | — | — | 0 | 0 | 0 | 0 | 0 | 0 |
| Cipro (5 μg)$^d$ | — | 24 | 24 | 35 | 26 | 28 | — | — |
| Nystatin (100 unit)$^e$ | — | — | — | — | — | — | 10 | 9 |

$^a$five folds concentrated,
$^b$ten folds concentrated,
$^c$the phagostimulatory solution as negative control,
$^{d,e}$reference antibiotics,
0: no inhibition,
—: not determined

Example 11

A Method to Test, Solid and Liquid Tumor Cell Types

This example discusses an in vitro assessment of the activity of LSE as applied to cancer and non-cancer cell lines.

In order to test the LSE for it's anticancer efficacy, it can be applied to additional cell lines that include, for example, MCF-7 (breast), PC-3 (prostate), K562 (leukemia), MeWo (skin melanoma), Mia PaCa-2 (pancreatic carcinoma), A549 (lung cancer), U87MG (brain tumor, glioblastoma), MCF10A (normal epithelial cells), HT-29 (colon carcinoma), CaCo-2 (normal intestinal epithelial cells), HEP 3B (human hepatoma liver cancer), ES-2 (ovarian carcinoma), HBEpC (normal human epithelial cells), CCRF-CEM (leukemia), HL-60(TB) (leukemia), MOLT-4 (leukemia), RPMI-8226 (leukemia), SR (leukemia), EKVX (non-small cell lung), HOP-62 (non-small cell lung), HOP-92 (non-small cell lung). NCI-H226 (non-small cell lung), NCI-H23 (non-small cell lung), NCI-H322M (non-small cell lung), NCI-H460 (non-small cell lung), NCI-H522 (non-small cell lung), COLO 205 (colon), HCC-2998 (colon), HCT-116 (colon), HCT-15 (colon), KM12 (colon), SW-620 (colon), SF-268 (CNS), SF-295 (CNS), SF-539 (CNS), SNB-19 (CNS), SNB-75 (CNS), U251 (CNS), LOX IMVI (melanoma), MALME-3M (melanoma), M14 (melanoma), SK-MEL-2 (melanoma), SK-MEL-28 (melanoma), SK-MEL-5 (melanoma), UACC-257 (melanoma), UACC-62 (melanoma), IGR-OV1 (ovarian), OVCAR-3 (ovarian), OVCAR-4 (ovarian), OVCAR-5 (ovarian), OVCAR-8 (ovarian), SK-OV-3 (ovarian), 786-0 (renal), A498 (renal), ACHN (renal), CAKI-1 (renal), RXF-393 (renal), SN12C (renal), TK-10 (renal), UO-31 (renal), DU-145 (prostate), NCI/ADR-RES (breast), MDA-MB-231/ATCC (breast), HS 578T (breast), MDA-MB-435 (breast), MDA-MB-468 (breast), BT-549 (breast), T-47D (breast), Saos-2 (bone cancer).

Materials and Methods a 96 well flat bottom plate; MTT (3-(4,5-dimethylthiazol-2-yl)-2,5-diphenyl tetrazolium bromide) (Sigma catalogue #M2128); reagent reservoirs; a multi-channel pipette; a multichannel repeater pipette; a set of single pipettors, 10 µL, 200 µL, 1000 µL; and various pipette tips.

Growth media, reagents and serum including Dulbecco's Modified Eagle Media (DMEM), high glucose; RPMI-1640 media; Iscove's; Hank's Buffered Salt Solution; L-glutamine; Fetal Bovine Serum; and Trypsin/EDTA.

To perform the MTT cytotoxicity assay, produce a stock solution of 5 mg MTT/ml PBS (phosphate buffered saline); use a sterile filter with 0.22 µM syringe filter; and store at 4° C. in the dark. Produce a working solution of 1 mg/ml dilute MTT stock solution with 1:4 (v/v) in pre-warmed culture medium.

Day 1, plate cells; Day 2, add drugs; Days 3-5, Read plates.

An example of a plate array design is as follows:

|   | 1 | 2 | 3 | 4 | 5 | 6 | 7 | 8 | 9 | 10 | 11 | 12 |
|---|---|---|---|---|---|---|---|---|---|----|----|----|
| A | X | X | X | X | X | X | X | X | X | X | X | X |
| B | X | media | control | 1433 | 717 | 358 | 179 | 90 | 45 | 22 | 11 | X |
| C | X | media | control | 1433 | 717 | 358 | 179 | 90 | 45 | 22 | 11 | X |
| D | X | media | control | 1433 | 717 | 358 | 179 | 90 | 45 | 22 | 11 | X |
| E | X | media | control | 1433 | 717 | 358 | 179 | 90 | 45 | 22 | 11 | X |
| F | X | media | control | 1433 | 717 | 358 | 179 | 90 | 45 | 22 | 11 | X |
| G | X | media | control | 1433 | 717 | 358 | 179 | 90 | 45 | 22 | 11 | X |
| H | X | X | X | X | X | X | X | X | X | X | X | X |

X: H2O; final volume all wells: 200 µL

Day 1: Plating Cells

Two cell lines can be plated on one 96-well plate such that tests are completed in triplicate for each (K562 is non-adherent, for example, and so should be on separate plate). Adherent cell lines must be plated one day prior to adding drugs to allow the cells to adhere to the plate, whereas non-adherent cells (suspension cells) can be plated on the same day (Day 2) prior to adding drugs.

Cells are first counted on the hemocytometer to observe the viability of the cells which should be greater than or equal to 90%. If this is not the case, the live cells should be separated from the dead cells using Ficoll-Paque (3 mL per 4 mL of cells, centrifuge for 25 min at 1500 rpm, wash cells once with culture medium 5 min at 1500 rpm). The number of cells to be plated per well varies with the growth rate of the cell line. The ideal optical density (O.D.) of the control cells should be between 1.00 and 2.00 by the end of the incubation time. Due to increased rate of evaporation along the border of the wells of the plate, it is not used for the assay, but is filled with 200 µl of sterile water.

Column B2-G2 is used as the blank and is filled with 200 µl of medium. Column B3-G3 is the control column with 100 µl of cells only. Drug is added to the cells in triplicate, therefore columns B4-D4, B5-D5, B6-D6 etc. to B11-D11 allows for 8 different concentrations of drug to be tested. This applied to the bottom half of the plate as well.

When adding cells to the plate to make sure that the cells are well suspended so that the same number of cells will be added to each well. Leave the plate in an incubator overnight for adherent cell lines to settle on the plate.

Day 2: Adding Drugs

If there are adherent cells, aspirate the used medium and add 100 µl of fresh medium. Add 100 µl of drug of desired concentration in each well. Since the total volume of the medium per well is 200 µl, dilute the drug accordingly. If you want the final concentration of drug to be 10 µM in the well, for example, you will have to make a 20 µM solution (100 µl of this plus 100 µl of your medium will give you a 10 µmol solution in a total of 200 µl). Add 100 µl of medium to wells in the control column (B3-G3). Return plate to incubator 72 hours.

Reading the Plate

At the end of the incubation period, add 50 µl per well of MTT working solution to all of the wells. Return plate to incubator for 3-4 hours and keep incubation times constant for repeat experiments. Set up your assay template on the plate reader. After 3-4 hours, remove plates from incubator. If the cells are non-adherent, they must be spun down for 10 minutes at 1800 rpm. Tip the 96 well plate on a 45° angle towards yourself. Using a 10-100 µl pipette tip attached to the vacuum, aspirate supernatant from each well. Add 150 µl DMSO per well.

Resuspend cells by placing plate on the plate shaker (5-10 min should be long enough). If needed, resuspend tough cells by hand using the multichannel pipette, being careful not to create bubbles. The best way to get rid of any bubbles in a 96 well plate is to direct a gentle stream of air onto the plate. Place plate into spectrophotometer and read at 570 nm.

Data Collection

The following records will be collected: growth cell optimization for each cell line; cytotoxicity of LSE; and cell viability graphs.

We claim:

1. A method of killing bacteria, comprising
contacting a bacteria in a fluid with a whole, leech saliva extract; the extract having a peptide molecular weight distribution with molecular weights of 3496 Daltons or greater; wherein the extract is produced from a process comprising:
 feeding a phagostimulatory agent to a leech;
 inducing a regurgitation in the leech, the inducing including placing the leech in an environment having a temperature of less than 0° C. or about 0° C.; and,
 collecting an unrefined, whole saliva in the regurgitation of the cooled leech.

2. The method of claim 1, further comprising revitalizing the leech by warming the leech in a water bath having a temperature ranging from about 5° C. to about 40° C.

3. The method of claim 2, wherein the method further comprises creating a refined, whole-saliva extract; the creating including removing solid components from the unrefined, whole saliva.

4. The method of claim 2, wherein the method further comprises lyophilizing separate volumes of the refined, whole saliva extract, the volumes not exceeding about 2 ml each.

5. The method of claim 1, the leech being *Hirudinaria manillensis*.

6. A method of treating a bacterial disease in a subject, comprising administrating an effective amount of a refined, whole leech saliva extract to the subject, the extract having a peptide molecular weight distribution with molecular weights of 3496 Daltons or greater; wherein the whole leech saliva extract functions as an antibacterial agent in the treatment of the bacterial disease, and the extract is produced from a process comprising:
 feeding a phagostimulatory agent to a leech;
 inducing regurgitation in the leech, the inducing including placing the leech in an environment having a temperature ranging from about −5° C. to about 15° C.;
 collecting an unrefined, whole saliva in the regurgitation of the cooled leech;
 removing solid components from the unrefined, whole saliva to create a refined, whole saliva; and,
 lyophilizing separate volumes of the refined, whole saliva extract, the volumes not exceeding about 2 ml each.

7. The method of claim 6, further comprising revitalizing the leech by warming the leech in a water bath having a temperature ranging from about 5° C. to about 40° C.

8. The method of claim 6, the leech being *Hirudinaria manillensis*.

9. The method of claim 6, wherein the bacterial disease is selected from the group consisting of anaplasmosis, anthrax, botulism, brucellosis, campylobacteriosis, chancroid, chlamydia, chlamydia trachomatis, cholera, diphtheria, donovanosis, ehrlichiosis, shiga toxin- and verocytotoxin-producing *Escherichia coli* (STEC/VTEC) infection, *Escherichia coli* O157:H7 infection, encephalitis, gonococcal infection, gonorrhea, hemolytic uremic syndrome, haemophilus influenza, Legionnaire's disease, leprosy, leptospirosis, listeriosis, meningococcal disease, bacterial meningitis, meningococcal septicaemia, methicillin-resistant *Staphylococcus aureus* infection (MRSA), paratyphoid fever, pertussis, bubonic plague, septicemic plague, pneumonic plague, pharyngeal plague, psittacosis, Q fever, relapsing fever, rickettsiosis, scarlet fever, salmonellosis, shigellosis, bacillary dysentery, Streptococcal infection, Pneumococcal infection, syphilis, tetanus, toxic shock syndrome, tuberculosis, tularemia, typhoid fever, typhus, vancomycin intermediate *Staph aureus* (VISA), vancomycin resistant *Staph aureus* (VRSA).

10. The method of claim 6, wherein the bacterial disease includes a gram-positive bacteria.

11. The method of claim 10, wherein the bacterial disease includes *Bacillus cereus* or *Staphylococcus aureus*.

12. The method of claim 6, wherein the bacterial disease includes a gram-negative bacteria.

13. The method of claim 12, wherein the bacterial disease includes *Pseudomonas aeruginosa, Escherichia coli*, or *Salmonella typhi*.

14. The method of claim 6, wherein the bacterial disease includes tuberculosis.

15. The method of claim 6, wherein the bacterial disease includes Pneumonia.

16. The method of claim 6, wherein the bacterial disease includes a foodborne illness from *Shigella*.

17. The method of claim 6, wherein the bacterial disease includes a foodborne illness from *Campylobacter*.

18. The method of claim 6, wherein the bacterial disease includes a foodborne illness from *Salmonella*.

19. The method of claim 6, wherein the collecting of the whole saliva yields a peptide molecular weight distribution that ranges from 4276 Daltons to 44386 Daltons.

20. The method of claim 6, wherein the collecting of the whole saliva yields a peptide molecular weight distribution that ranges from 6289 Daltons to 14244 Daltons.

21. The method of claim 6, wherein the collecting of the whole saliva yields a peptide molecular weight distribution that ranges from 10812 Daltons to 88210 Daltons.

22. The method of claim 6, wherein the collecting of the whole saliva yields a peptide molecular weight distribution that ranges from 3496 Daltons to 88210 Daltons.

* * * * *